United States Patent
Mikoshiba et al.

(10) Patent No.: US 8,853,424 B2
(45) Date of Patent: Oct. 7, 2014

(54) PROTEIN CROSS-LINKING INHIBITOR

(75) Inventors: Katsuhiko Mikoshiba, Saitama (JP);
Nobuyuki Nukina, Saitama (JP);
Shoichiro Ozaki, Saitama (JP); Kouzo Hamada, Saitama (JP); Jun-Ichi Goto, Saitama (JP); Akinobu Suzuki, Saitama (JP); Etsuko Ebisui, Saitama (JP); Akiko Terauchi, Saitama (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 551 days.

(21) Appl. No.: 13/058,647

(22) PCT Filed: Aug. 11, 2009

(86) PCT No.: PCT/JP2009/064206
§ 371 (c)(1),
(2), (4) Date: May 10, 2011

(87) PCT Pub. No.: WO2010/018837
PCT Pub. Date: Feb. 18, 2010

(65) Prior Publication Data
US 2011/0212919 A1 Sep. 1, 2011

(30) Foreign Application Priority Data
Aug. 11, 2008 (JP) ................. 2008-207315

(51) Int. Cl.
*C07D 333/00* (2006.01)
*A61K 31/67* (2006.01)
*C07F 5/02* (2006.01)
*A61K 31/69* (2006.01)

(52) U.S. Cl.
CPC .......... *C07F 5/025* (2013.01); *A61K 31/69* (2013.01)
USPC .................................. 549/4; 514/96

(58) Field of Classification Search
None
See application file for complete search history.

(56) References Cited

U.S. PATENT DOCUMENTS

| 8,017,809 B2 * | 9/2011 | Mikoshiba et al. ............... 568/3 |
| 2004/0259842 A1 | 12/2004 | Mikoshiba et al. |
| 2006/0009422 A1 | 1/2006 | Perry et al. |
| 2006/0014723 A1 | 1/2006 | Bellinger-Kawahara et al. |
| 2006/0019927 A1 | 1/2006 | Bellinger-Kawahara et al. |

FOREIGN PATENT DOCUMENTS

| EP | 1 961 756 A1 | 8/2008 |
| JP | 2008-502694 A | 1/2008 |
| JP | 2008-502702 A | 1/2008 |
| JP | 2009-184988 A | 8/2009 |
| WO | WO 97/40859 A1 | 11/1997 |
| WO | WO 02/44184 A2 | 6/2002 |
| WO | WO 03/033002 A1 | 4/2003 |
| WO | WO 2006/074419 A2 | 7/2006 |
| WO | WO 2007/056341 A1 | 5/2007 |
| WO | WO 2007/061074 A1 | 5/2007 |
| WO | WO 2007/098418 A1 | 8/2007 |
| WO | WO 2007/125351 A1 | 11/2007 |
| WO | WO 2007/146965 A2 | 12/2007 |
| WO | WO 2008/055068 A2 | 5/2008 |

OTHER PUBLICATIONS

CAPLUS 1970:531065.*
Dean, H. et al, J. Biol. Chem. 2008, vol. 283, pp. 16790-16800.*
International Search Report, dated Jan. 12, 2010, issued in PCT/JP2009/064206.

* cited by examiner

*Primary Examiner* — Heidi Reese
(74) *Attorney, Agent, or Firm* — Birch, Stewart, Kolasch & Birch, LLP

(57) ABSTRACT

The present invention provides a protein cross-linking inhibitor containing a compound represented by any of the following formulas (1)-(13), or a pharmaceutically acceptable salt thereof:

$$R_3-[-X-B(ZR_1)-Y-B(ZR_2)-W-]_n-R_4, \quad (1)$$

$$R_3-[-X-B(ZR_1)-Y-]_n-R_4, \quad (2)$$

$$R_3-[-B(ZR_1)-Y-B(ZR_2)-W-]_n-R_4, \quad (3)$$

$$R_3-[-X-B(ZR_1)-]_n-R_4, \quad (4)$$

$$R_3-[-B(ZR_2)-W-]_n-R_4, \quad (5)$$

$$R_3-X-B(ZR_1)-T[B(ZR_2)-W-R_4]_2, \quad (6)$$

$$R_3-B(OH)_2, \quad (7)$$

$$R_3-B(ZR_1)-X-B(ZR_2)-R_4, \quad (8)$$

$$R_3-B(R_1)-O-B(R_2)-R_4, \quad (9)$$

$$R_3-[-X-B(ZR_1)-Y-B(ZR_2)-]_n-R_4, \quad (10)$$

$$R_3-[-X-B(ZR_1)-Y-B(ZR_2)-W-Q-]_n-R_4, \quad (11)$$

$$R_3-[-P-X-B(ZR_1)-Y-B(ZR_2)-W-]_n-R_4, \quad (12)$$

$$[R_3-X-B(ZR_1)-Y]_2B(ZR_2), \quad (13)$$

wherein each symbol is as defined in the DESCRIPTION.

8 Claims, 1 Drawing Sheet

PROTEIN CROSS-LINKING INHIBITOR

TECHNICAL FIELD

The present invention relates to a protein cross-linking inhibitor comprising a boron compound. Furthermore, the present invention relates to a novel boron compound useful for use thereof.

BACKGROUND ART

Calcium ion is essential for the body, and the concentration of intracellular $Ca^{2+}$ constituting the body is as extremely low as $10^{-7}$M, which is 1 to 10,000 relative to the extracellular concentration. When the cell is stimulated, intracellular $Ca^{2+}$ increases to generate $Ca^{2+}$ wave that produces slow intracellular $Ca^{2+}$ oscillation, and induces physiological function.

SOCE (store-operated calcium entry) is also called capacitive calcium entry, which is a mechanism that causes extracellular influx of $Ca^{2+}$ for replenishment of depleted intracellular $Ca^{2+}$ stores, and important for long-term sustainability of intracellular $Ca^{2+}$ signals.

SOCE is measured as Icrac (calcium release-activated calcium-selective current). It has been clarified that SOCE and Icrac channel are defective in the T cells of patients with severe combined immunodeficiency (SCID). Furthermore, it has also been clarified that a protein called STIM (stromal interaction molecule) senses depletion of $Ca^{2+}$ in the endoplasmic reticulum, passes the information to the cellular membrane, and activates CRACM (calcium release-activated calcium modulator) (Orai) located in the cellular membrane and forms Icrac channel pore.

Extracellular stimulus is recognized by a receptor on the cellular membrane, the information thereof activates PLC (phospholipase C) via G protein and hydrolyzes PIP2 (phosphatidylinositol bisphosphate), which is an inositolphospholipid in the cellular membrane, and produces diacylglycerol and IP3 (inositol trisphosphate). Diacylglycerol activates protein kinase C and phosphorylates protein, causing various physiological phenomena. IP3 acts on IP3 receptor to cause release of $Ca^{2+}$. The present inventors have found an IP3 receptor molecule in mutant mouse, and successfully determined all base sequences of the membrane protein (non-patent document 1). In addition, they have clarified that the IP3 receptor localizes in the endoplasmic reticulum, and this is the calcium channel (non-patent documents 1-5). Furthermore, the present inventors have clarified that the IP3 receptor is the molecule involved in development and differentiation, neural plasticity and various signal transduction (non-patent documents 6-11). In addition, they have clarified that the IP3 receptor is also bound to the $Ca^{2+}$ channel on the cell membrane surface (non-patent document 12).

2-Aminoethyl diphenylborinate (2-APB: $C_6H_5B(OCH_2CH_2NH_2)C_6H_5$) has been internationally recognized as an IP3 receptor inhibitor, and is sold from Sigma. It decreases intracellular calcium concentration by inhibiting SOCE. The present inventors have synthesized and found compounds that control intracellular calcium concentration (patent document 1, patent document 2, Japanese patent application No. 2008-028152).

It has been clarified that the causes of intractable diseases such as Alzheimer's disease, Parkinson's disease, Celiac disease, cataract, mad cow disease, congenital lamellar ichthyosis, congenital hemostatic disorder and the like are based on the abnormal cross-linking reaction of proteins (non-patent document 13, non-patent document 14). In addition, it has also been clarified that the cause of Huntington's disease is abnormal aggregation of polyglutamine (non-patent document 15).

Transglutaminase is an enzyme activated by the presence of $Ca^{2+}$, and its involvement in neurological diseases such as Alzheimer's disease, Parkinson's disease, Huntington's disease and the like has recently been known. Therefore, novel inhibitors thereof are considered to be effective as therapeutic drugs for the diseases (non-patent document 16, non-patent document 17). A reaction forming an isopeptide bond by deammoniation of an amide group of glutamine and an amino group of lysine is the main reaction of protein cross-linking. The mechanism by which an inhibitor of enzyme transglutaminase causing the reaction is effective for the aforementioned neurological diseases has been clarified (non-patent document 19). As a basis, while many studies have been made based on the above to develop inhibitors of transglutaminase as therapeutic drugs for intractable diseases such as Alzheimer's disease, Huntington's disease, Parkinson's disease and the like (non-patent documents 17-23), a boron compound having a transglutaminase inhibitory activity has not been reported heretofore.

DOCUMENT LIST

Patent Documents patent document 1: WO03/033002 (U.S. Pat. No. 7,217,701)
patent document 2: WO2007/061074

Non-Patent Documents non-patent document 1: Furuichi, T. et al. Primary structure and functional expression of the inositol 1,4,5-trisphosphate-binding protein P400. Nature. 1989 Nov. 2; 342(6245):32-8.

non-patent document 2: Miyawaki, A. et al. Expressed cerebellar-type inositol 1,4,5-trisphosphate receptor, P400, has calcium release activity in a fibroblast L cell line. Neuron. 1990 July; 5(1):11-8.

non-patent document 3: Maeda, N. et al. Structural and functional characterization of inositol 1,4,5-trisphosphate receptor channel from mouse cerebellum. J Biol. Chem. 1991 Jan. 15; 266(2):1109-16.

non-patent document 4: Kume, S. et al. The Xenopus 1P3 receptor: structure, function, and localization in oocytes and eggs. Cell. 1993 May 7; 73(3):555-70.

non-patent document 5: Yamamoto-Hino, M. et al. Cloning and characterization of human type 2 and type 3 inositol triphosphate receptors. Receptors and Channels. 1994; 2: 9-22.

non-patent document 6: Miyazaki, S. et al. Block of $Ca^{2+}$ wave and $Ca^{2+}$ oscillation by antibody to the inositol 1,4,5-trisphosphate receptor in fertilized hamster eggs. Science. 1992 Jul. 10; 257(5067):251-5.

non-patent document 7: Kume, S. et al. Role of inositol 1,4,5-trisphosphate receptor in ventral signaling in Xenopus embryos. Science. 1997 Dec. 12; 278(5345):1940-3.

non-patent document 8: Takei, K. et al. Regulation of nerve growth mediated by inositol 1,4,5-trisphosphate receptors in growth cones. Science. 1998 Nov. 27; 282(5394):1705-8.

non-patent document 9: Nishiyama, M. et al. Calcium stores regulate the polarity and input specificity of synaptic modification. Nature. 2000 Nov. 30; 408(6812):584-8.

non-patent document 10: Bosanac, I. et al. Structure of the inositol 1,4,5-trisphosphate receptor binding core in complex with its ligand. Nature. 2002 Dec. 12; 420(6916):696-700. Epub 2002 Nov. 17.

non-patent document 11: Matsumoto, M. et al. Ataxia and epileptic seizures in mice lacking type 1 inositol 1,4,5-trisphosphate receptor. Nature. 1996 Jan. 11; 379(6561): 168-71.

non-patent document 12: Boulay, G. et al. Modulation of Ca(2+) entry by polypeptides of the inositol 1,4,5-trisphosphate receptor (IP3R) that bind transient receptor potential (TRP): evidence for roles of TRP and IP3R in store depletion-activated Ca(2+) entry. Proc Natl Acad Sci USA. 1999 Dec. 21; 96(26): 14955-60.

non-patent document 13: Nobuyuki Nukina, Toru Nishikawa Experiment Medicine 25, No 13, (extra edition), page 20-29 (2007)

non-patent document 14: Hartley M Dean et al. Transglutaminase induces protofibril-like amyloid β-protein assemblies that are protease-resistant and inhibit long-term potentiation. J. Biol. Chem. 2008 283: 16790-16800.

non-patent document 15: Thomas M. Jeitner, et al. Increased levels of γ-glutamylamines in Huntingtondisease CSF. J. Neurochemistry 2008 Apr. 1; 106(1):7-44.

non-patent document 16: Kim, S. Y, et al. Transglutaminases in disease. Neurochem Int. 2002 January; 40(1):85-103.

non-patent document 17: Hoffner G, and Djian P. Transglutaminase and diseases of the central nervous system. Front Biosci. 2005 Sep. 1; 10:3078-92.

non-patent document 18: Duval E, et al. Structure-activity relationship study of novel tissue transglutaminase inhibitors. Bioorg Med Chem. Lett. 2005 Apr. 1; 15(7):1885-9.

non-patent document 19: L. Lorand Neurodegenerative diseases and transglutaminase. Proc Natl Acad Sci USA. 1996 Dec. 10; 93(25):14310-3.

non-patent document 20: Mastroberardino P G, et al. 'Tissue' transglutaminase ablation reduces neuronal death and prolongs survival in a mouse model of Huntington's disease. Cell Death Differ. 2002 September; 9(9):873-80.

non-patent document 21: Grierson A J, et al. Three different human tau isoforms and rat neurofilament light, middle and heavy chain proteins are cellular substrates for transglutaminase. Neurosci Lett. 2001 Jan. 26; 298(1): 9-12.

non-patent document 22: Watts R E, et al. Structure-activity relationship analysis of the selective inhibition of transglutaminase 2 by dihydroisoxazoles. J Med. Chem. 2006 Dec. 14; 49(25): 7493-501.

non-patent document 23: Karpuj M V, et al. Prolonged survival and decreased abnormal movements in transgenic model of Huntingtondisease, with administration of the transglutaminase inhibitor cystamine. Nat. Med. 2002 February; 8(2): 143-9.

SUMMARY OF THE INVENTION

Problems to be Solved by the Invention

The present invention aims to develop a prophylaxis and/or therapeutic drug for diseases caused by cross-linking abnormality of protein (Alzheimer's disease, Parkinson's disease, Celiac disease, cataract, mad cow disease, congenital lamellar ichthyosis, congenital hemostatic disorder etc.).

Means of Solving the Problems

The present inventors have conducted intensive studies in an attempt to solve the aforementioned problems and found that a series of boron compounds, particularly the compounds represented by the following formulas (1)-(13) (hereinafter to be also simply referred to as compounds (1)-(13)), inhibit cross-linking of protein, and the compounds can be used as prophylactic and/or therapeutic drugs for diseases caused by abnormal cross-linking of proteins.

Accordingly, the present invention provides the following.

[1] A compound represented by any of the following formulas (1)-(13) or a pharmaceutically acceptable salt thereof;

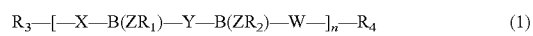  (1)

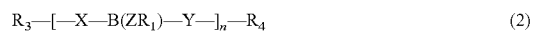  (2)

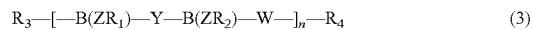  (3)

  (4)

  (5)

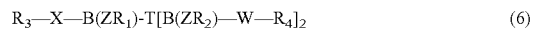  (6)

  (7)

  (8)

  (9)

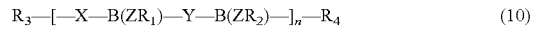  (10)

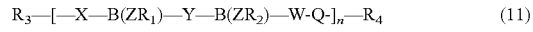  (11)

  (12)

  (13)

wherein B is a boron atom,

Z is O or S, $R_1$ and $R_2$ are independently a group selected from H, $-(CH_2)_m-NR_5R_6$, $-CO-(CH_2)_m-NR_7R_9$, $-COCH(NH_2)-R_9$, $-CH_2CH(NH_2)-R_{10}$, $-CHR_{11}R_{12}$, $-COCH(-NR_{13}R_{14})-R_{15}$, $-COCH(NH_2)-(CH_2)_m-NHCR_{18}NH_2$, $-COCH(NH_2)-(CH_2)_m-COR_{19}$, $-COR_{20}$, $-(CH_2)_m-R_{22}$, $-O(CH_2)_mNH_2$, $-COCH(NH_2)-(CH_2)_m-R_{23}$, $-(CH_2CH_2NH)_2-R_{23}$,

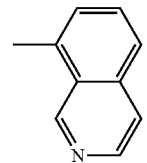

and heterocyclylalkyl, or when $R_1$ and $R_2$ are present in plurality, $R_1$ may be bonded to $R_1$, $R_2$ may be bonded to $R_2$, or $R_1$ may be bonded to $R_2$, $R_5$, $R_6$, $R_7$, $R_8$, $R_9$, $R_{10}$, $R_{11}$, $R_{12}$, $R_{13}$, $R_{14}$, $R_{15}$, $R_{19}$, $R_{20}$ and $R_{22}$ are independently H, or each is a substituted or unsubstituted alkyl, alkenyl, alkynyl, cycloalkyl, cycloalkenyl, aryl, arylalkyl, heterocyclyl, amino, aminoalkylcarbonyl, hydroxy, aromatic group or heterocyclylalkyl, $R_{18}$ is oxo or =NH, Q is a group represented by $-R_{16}-O-R_{17}-$, $-R_{21}-O-$ or $-O-$ (wherein $R_{16}$, $R_{17}$ and $R_{21}$ mean a single bond or lower alkylene), $R_{23}$ is a fluorescence group, m is an integer of 1 to 5, $R_3$ and $R_4$ are H, OH, $CH_2OH$, $CH_2OCH_2OCH_3$, cyano or aryloxy, or each is a substituted or unsubstituted alkyl or aryl, T is a substituted or unsubstituted aryl,
X, Y and W are independently groups containing aromatic series or fatty series, and
n is an integer of 1 to 100.

[2] A compound represented by any of the following formulas (1)-(13) or a pharmaceutically acceptable salt thereof;

$$R_3—[—X—B(ZR_1)—Y—B(ZR_2)—W—]_n—R_4 \quad (1)$$

$$R_3—[—X—B(ZR_1)—Y—]_n—R_4 \quad (2)$$

$$R_3—[—B(ZR_1)—Y—B(ZR_2)—W—]_n—R_4 \quad (3)$$

$$R_3—[—X—B(ZR_1)—]_n—R_4 \quad (4)$$

$$R_3—[—B(ZR_2)—W—]_n—R_4 \quad (5)$$

$$R_3—X—B(ZR_1)\text{-}T[B(ZR_2)—W—R_4]_2 \quad (6)$$

$$R_3—B(OH)_2 \quad (7)$$

$$R_3—B(ZR_1)—X—B(ZR_2)—R_4 \quad (8)$$

$$R_3—B(R_1)—O—B(R_2)—R_4 \quad (9)$$

$$R_3—[—X—B(ZR_1)—Y—B(ZR_2)—]_n—R_4 \quad (10)$$

$$R_3—[—X—B(ZR_1)—Y—B(ZR_2)—W\text{-}Q\text{-}]_n—R_4 \quad (11)$$

$$R_3—[—O—X—B(ZR_1)—Y—B(ZR_2)—W—]_n—R_4 \quad (12)$$

$$[R_3—X—B(ZR_1)—Y]_2B(ZR_2) \quad (13)$$

wherein B is a boron atom,
Z is O or S,
$R_1$ and $R_2$ are independently a group selected from H, —$(CH_2)_m$—$NR_5R_6$, —CO—$(CH_2)_m NR_7R_8$, —COCH($NH_2$)—$R_9$, —$CH_2CH(NH_2)$—$R_{10}$, —$CHR_{11}R_{12}$, —COCH(—$NR_{13}R_{14}$)—$R_{15}$, —COCH($NH_2$)—$(CH_2)_m$ $NHCR_{18}NH_2$, —COCH($NH_2$)—$(CH_2)_m$—$COR_{19}$, —$COR_{20}$, —$(CH_2)_m$—$R_{22}$, —$O(CH_2)_m NH_2$, —COCH($NH_2$)—$(CH_2)_m$—$R_{23}$, —$(CH_2CH_2NH)_2$—$R_{23}$,

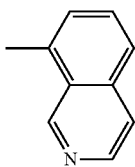

and heterocyclylalkyl, or when $R_1$ and $R_2$ are present in plurality, $R_1$ may be bonded to $R_1$, $R_2$ may be bonded to $R_2$, or $R_1$ may be bonded to $R_2$, $R_5$, $R_6$, $R_7$, $R_8$, $R_9$, $R_{10}$, $R_{11}$, $R_{12}$, $R_{13}$, $R_{14}$, $R_{15}$, $R_{19}$, $R_{20}$ and $R_{22}$ are independently H, or each is a substituted or unsubstituted alkyl, alkenyl, alkynyl, cycloalkyl, cycloalkenyl, aryl, arylalkyl, heterocyclyl, amino, aminoalkylcarbonyl, hydroxy, aromatic group or heterocyclylalkyl, $R_{18}$ is oxo or =NH,
Q is a group represented by —$R_{16}$—O—$R_{11}$—, —$R_{21}$—O—, or —O— (wherein $R_{16}$, $R_{17}$ and $R_{21}$ mean a single bond or lower alkylene),
$R_{23}$ is a fluorescence group,
m is an integer of 1 to 5,
$R_3$ and $R_4$ are H, OH, $CH_2OH$, $CH_2OCH_2OCH_3$, cyano or aryloxy, or each is a substituted or unsubstituted alkyl or aryl,
T is a substituted or unsubstituted aryl,
X, Y and W are independently groups containing aromatic series or fatty series, and
n is an integer of 1 to 100, excluding a compound represented by the following formula (Ia)

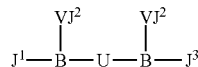

wherein
B is a boron atom,
B is an oxygen or sulfur atom,
$J^1$ and $J^3$ are each independently a monocyclic aromatic group, a polycyclic aromatic group, or a heterocyclic group containing at least one hetero atom selected from an oxygen atom, a nitrogen atom and a sulfur atom,
$J^2$ is a hydrogen atom; —$(CH_2)_D$—$NJ^4J^5$ wherein D is an integer of 1-4,
$J^4$ and $J^5$ are independently a hydrogen atom, or $C_{1-4}$ alkyl substituted or unsubstituted by an amino group, a mono or di-$C_{1-4}$ alkylamino group or a phenyl group, or $J^4$ and $J^5$ form, together with the nitrogen atom bonded thereto, a 5- or 6-membered cyclo ring); —CO—$(CH_2)_D$—$NJ^4J^5$ wherein D, $J^4$ and $J^5$ are as defined above; —COCH($NH_2$)$J^6$ wherein $J^6$ is an amino acid residue, or —$(CH_2)_{D'}NH_2$ wherein D' is an integer of 1 to 3; —$CHJ^7J^8$ wherein $J^7$ and $J^8$ are independently an amino group, $C_{1-4}$ alkyl substituted or unsubstituted by a mono or di($C_{1-4}$ alkyl substituted or unsubstituted by an amino group)amino group or phenyl group, or phenyl substituted by pyridyl or a $C_{1-3}$ alkoxy group; —$CH_2CH(NH_2)$-$J^6$ wherein $J^9$ is phenyl, or $C_{1-4}$ alkyl substituted by phenyl; quinolyl or isoquinolyl substituted by a alkyl group; or $C_{1-4}$ alkyl substituted by a pyridyl group, a piperidino group or a pyrrolidinyl group, and
U is a monocyclic aromatic group, a polycyclic aromatic group or a heterocyclic group, which is the same as or different from $J^1$ and $J^3$, or a bifunctional group having a monocyclic aromatic group, a polycyclic aromatic group or a heterocyclic group bonded to both sides thereof via a group selected from the group consisting of a single bond, O, $CH_2$, S, $SO_2$, $CH_2OCH_2$, $OCH_2$, $OCH_2CH_2OCH_2$, $OCH_2OCH_2CH_2$ and $CH_2OCH_2CH_2$, and a compound represented by the following formula (Ib)

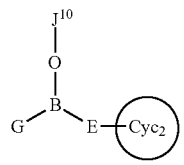

wherein $J^{10}$ is
(1) a hydrogen atom,
(2) —$(CH_2)_{D''}NJ^{11}J^{12}$ wherein D" is an integer of 1 to 3, $J^{11}$ and $J^{12}$ are each independently a hydrogen atom, $C_{1-4}$ alkyl, $C_{5-6}$ monocyclic carbocycle, $C_{1-4}$ alkyl substituted by $C_{5-6}$ monocyclic carbocycle, or 5- or 6-membered monocyclic heterocycle,
the carbon atom in —$(CH_2)_{D''}$— is optionally substituted by 1 or 2 $J^{13}$, and further, said carbocycle and heterocycle are optionally substituted by 1 or 2 $J^{16}$,
$J^{13}$ is (a) $C_{1-8}$ alkyl, (b) carboxyl, (c) $C_{1-4}$ alkoxycarbonyl, (d) keto, (e) $C_{5-6}$ monocyclic carbocycle, (f) guanidino($C_{1-2}$) alkyl, (g) $C_{1-6}$ alkyl substituted by $C_{5-6}$ monocyclic carbocycle, (h) $C_{1-2}$ alkyl substituted by 4-chlorophenoxy, or (i) $C_{1-4}$ alkyl substituted by di($C_{1-4}$ alkylamino, (3) $C_{1-6}$ alkyl or $C_{2-6}$ alkenyl substituted by $C_{5-6}$ monocyclic carbocycle, wherein said carbocycle is optionally substituted by 1 to 5 $J^{16}$, and further, said $C_{1-6}$ alkyl or $C_{2-6}$ alkenyl is optionally substituted by 1 or 2 $J^{19}$, (4) $C_{1-6}$ alkyl or $C_{2-6}$ alkenyl substituted by 5- or 6-membered monocyclic heterocycle, wherein said heterocycle is optionally substituted by 1 to 5 $J^{16}$, and further, said $C_{1-6}$ alkyl or $C_{2-6}$ alkenyl is optionally substituted by 1 or 2 $J^{19}$, and $J^{19}$ is $C_{1-4}$ alkyl or $C_{2-4}$ alkenyl, (5) a —$CHJ^{14}J^{15}$ group wherein $J^{14}$ and $J^{15}$ are each independently (i) $C_{5-6}$ monocyclic carbocycle, (ii) 5- or 6-membered monocyclic heterocycle, (iii) $C_{1-6}$ alkyl or $C_{2-6}$ alkenyl substituted by $C_{5-6}$ monocyclic carbocycle, or (iv) $C_{1-6}$ alkyl or $C_{2-6}$ alkenyl substituted by 5- or 6-membered monocyclic heterocycle, wherein said carbocycle and heterocycle are optionally substituted by 1 to 5 $J^{16}$, or (6) 5,6,7,8-tetrahydroquinolin-8-yl, $J^{16}$ is (a) $C_{1-4}$ alkyl, (b) $C_{1-4}$ alkoxy, (c) a halogen atom, (d) —$CF_3$, (e) nitro, (f) $C_{5-6}$ monocyclic carbocycle, (g) $C_{1-4}$ alkyl substituted by $C_{5-6}$ monocyclic carbocycle, (h) amino, (i) —NHCO($C_{1-4}$ alkyl), or (j) $C_{1-4}$ alkoxycarbonyl, G is $Cyc_1$ or hydroxy, $Cyc_1$ is $C_{5-10}$ monocyclic or bicyclic carbocycle, or 5- to 10-membered monocyclic or bicyclic heterocycle, wherein said carbocycle and heterocycle are optionally substituted by 1 to 5 $J^{17}$, $Cyc_2$ is $C_{5-10}$ monocyclic or bicyclic heterocycle or 5- to 10-membered monocyclic or bicyclic heterocycle, wherein said carbocycle and heterocycle are optionally substituted by 1 to 5 $J^{18}$, $J^{17}$ and $J^{18}$ are each independently (a) $C_{1-4}$ alkyl, (b) $C_{2-4}$ alkenyl, (c) $C_{1-4}$ alkoxy, (d) a halogen atom, (e) —$CF_3$, (f) alkylthio, (g) amino, (h) ($C_{1-4}$ alkyl)amino, (i) di($C_{1-4}$ alkyl)amino, (j) formyl, (k) phenyl, (l) phenoxy, (m) hydroxy($C_{1-2}$)alkyl, (n) ($C_{5-10}$ monocyclic or bicyclic carbocycle)-O—($C_{1-2}$) alkyl, (o) $C_{1-4}$ alkoxycarbonylvinyl, (p) $C_{1-2}$ alkyl substituted by a group selected from —O—($C_{1-2}$ alkylene)-phenyl (said phenyl is optionally substituted by 1 to 3 $C_{1-4}$ alkoxy), —O—CONH-phenyl (said phenyl is optionally substituted by 1 to 3 $C_{1-4}$ alkyl, nitro or $C_{1-4}$ alkoxycarbonyl), or —O—CONH—($C_{1-4}$)alkyl (said alkyl is optionally substituted by 1 to 3 $C_{1-4}$ alkyl, carboxyl or $C_{1-4}$ alkoxycarbonyl), (q) phenylthio, (r) —$CON(C_{1-4}$ alkyl$)_2$, (s) —$SO_2N(C_{1-4}$ alkyl$)_2$, (t) alkoxy($C_{1-2}$)alkyl, (u) $C_{1-4}$ alkoxycarbonyloxy($C_{1-2}$)alkyl,

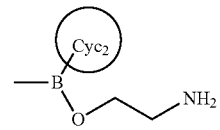
(v)

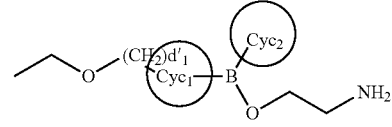
(w)

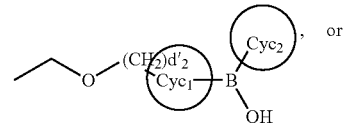
(x) or

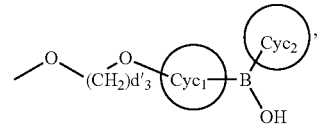
(y)

carbocycle, phenyl, $Cyc_1$ and $Cyc_2$ in $J^{17}$ and $J^{18}$ are optionally substituted by 1 or 2 $J^{18}$, or $J^{17}$ and $J^{18}$ in combination optionally show —O—, and $J^{18}$ and $J^{19}$ in combination optionally show a single bond, $d'_1$ is an integer of 1 to 4, $d'_2$ is an integer of 1 to 4, $d'_3$ is an integer of 1 to 4, and E is a single bond or $C_{1-4}$ alkylene substituted or unsubstituted by $C_{5-6}$ monocyclic carbocycle.

[3] The compound of [2] represented by the following formula (4') or (8')

$$R_3'—[X'—B(ZR_1')—]_n—R_4' \quad (4')$$

$$R_3'—B(ZR_1')—X'—B(ZR_2')—R_4' \quad (8')$$

wherein B is a boron atom,

Z is O or S, $R_1'$ and $R_2'$ are H, —$(CH_2)_m$—$NR_5'R_6'$, —$COCH(NH_2)$—$(CH_2)_m$NHCONH_2$ or —$COCH(NH_2)$—$(CH_2)_m$—$COR_{19}'$, wherein $R_5'$, $R_6'$, $R_{11}'$, $R_{12}'$ and $R_{19}'$ are independently H, or each is a substituted or unsubstituted amino, heterocyclyl or aryloxy, $R_3'$ and $R_4'$ are H, aryl or heterocyclyl, X' is a substituted or unsubstituted aromatic group, m is an integer of 1 to 5, and n is an integer of 1 to 100, or a pharmaceutically acceptable salt thereof.

[4] The compound of [2] or [3], which is any of

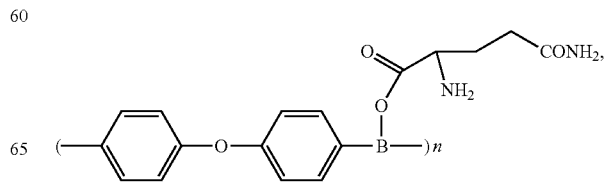

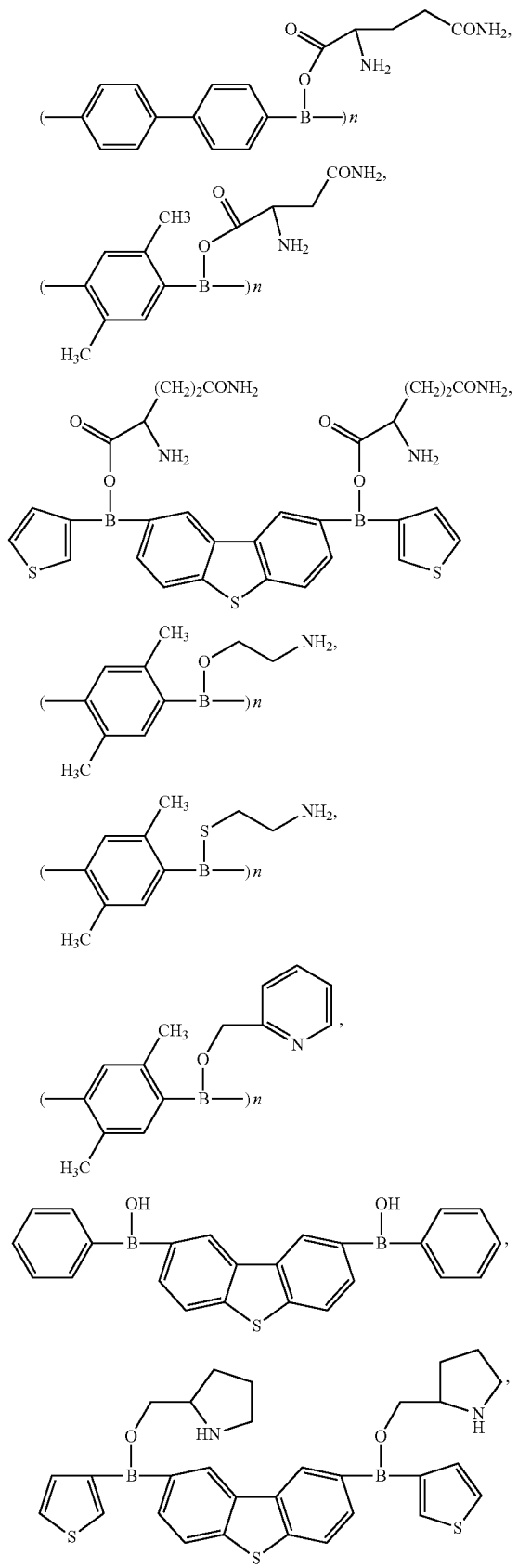
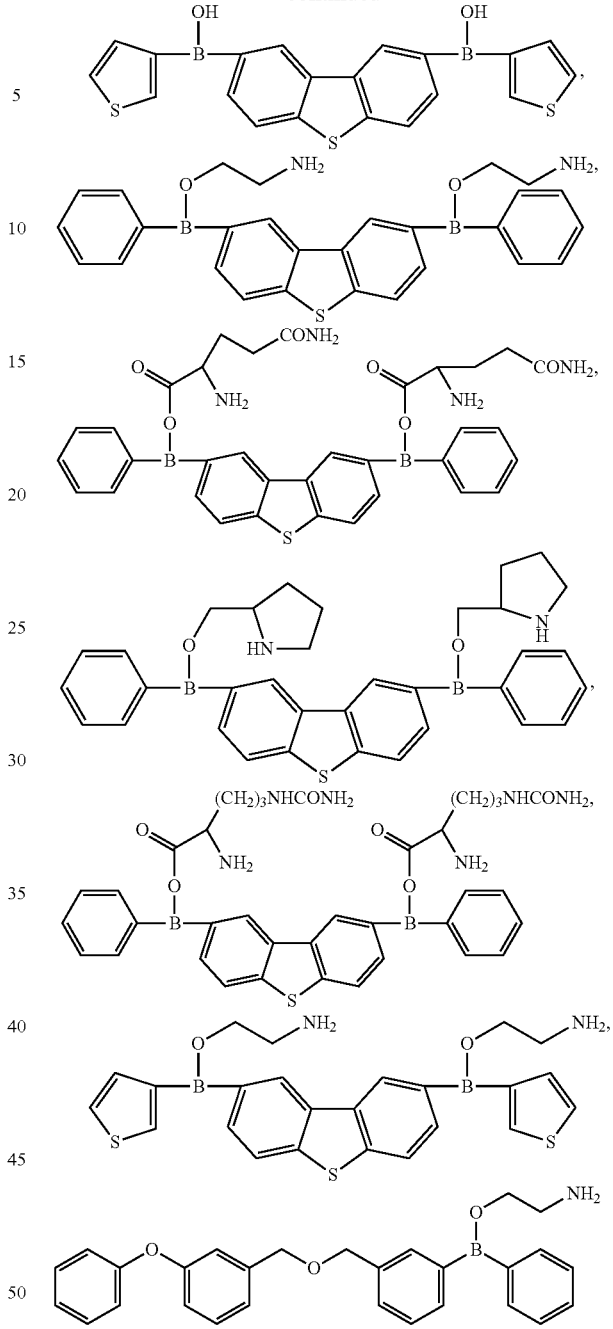

wherein n is an integer of 1 to 100, or a pharmaceutically acceptable salt thereof.

[5] A protein cross-linking inhibitor comprising the compound of [2] to [4] or a pharmaceutically acceptable salt thereof.

[6] The inhibitor of [5], wherein the compound is represented by the formula (1) or (8)

R₃—[—X—B(ZR₁)—Y—B(ZR₂)—W—]ₙ—R₄    (1)

R₃—B(ZR₁)—X—B(ZR₂)—R₄    (8)

wherein each symbol is as defined in [2].

[7] A prophylactic and/or therapeutic drug for a disease caused by cross-linking of protein, comprising the compound of [2] to [4] or a pharmaceutically acceptable salt thereof.

[8] The prophylactic and/or therapeutic drug of [7], wherein the compound is represented by the formula (1) or (8)

$$R_3\text{—}[\text{—}X\text{—}B(ZR_1)\text{—}Y\text{—}B(ZR_2)\text{—}W\text{—}]_n\text{—}R_4 \quad (1)$$

$$R_3\text{—}B(ZR_1)\text{—}X\text{—}B(ZR_2)\text{—}R_4 \quad (8)$$

wherein each symbol is as defined in [2].
[9] The prophylactic and/or therapeutic drug of [7] or [8], wherein the disease caused by cross-linking of protein is selected from Alzheimer's disease, Parkinson's disease, Celiac disease, cataract, mad cow disease, congenital lamellar ichthyosis and congenital hemostatic disorder.
[10] A method of preventing and/or treating a disease caused by cross-linking of protein, comprising administering an effective amount of the compound of [2] to [4] or a pharmaceutically acceptable salt thereof to a subject.
[11] The method of [10], wherein the compound is represented by the formula (1) or (8)

$$R_3\text{—}[\text{—}X\text{—}B(ZR_1)\text{—}Y\text{—}B(ZR_2)\text{—}W\text{—}]_n\text{—}R_4 \quad (1)$$

$$R_3\text{—}B(ZR_1)\text{—}X\text{—}B(ZR_2)\text{—}R_4 \quad (8)$$

wherein each symbol is as defined in [2].
[12] The method of [10] or [11], wherein the disease caused by cross-linking of protein is selected from Alzheimer's disease, Parkinson's disease, Celiac disease, cataract, mad cow disease, congenital lamellar ichthyosis and congenital hemostatic disorder.
[13] The compound of [2] to [4] to be used for the prophylaxis and/or treatment of disease caused by cross-linking of protein, or pharmaceutically acceptable salts thereof.
[14] The compound of [13] which is represented by the formula (1) or (8)

$$R_3\text{—}[\text{—}X\text{—}B(ZR_1)\text{—}Y\text{—}B(ZR_2)\text{—}W\text{—}]_n\text{—}R_4 \quad (1)$$

$$R_3\text{—}B(ZR_1)\text{—}X\text{—}B(ZR_2)\text{—}R_4 \quad (8)$$

wherein each symbol is as defined in [2], or a pharmaceutically acceptable salt thereof.
[15] The compound of [13] or [14], wherein the disease caused by cross-linking of protein is selected from Alzheimer's disease, Parkinson's disease, Celiac disease, cataract, mad cow disease, congenital lamellar ichthyosis and congenital hemostatic disorder, or a pharmaceutically acceptable salt thereof.

Effect of the Invention

The present invention can provide a prophylactic and/or therapeutic drug for the diseases based on an abnormal cross-linking reaction of protein such as Alzheimer's disease, Parkinson's disease, Celiac disease, cataract, mad cow disease, congenital lamellar ichthyosis, congenital hemostatic disorder and the like.

DESCRIPTION OF EMBODIMENTS

Figure 1:
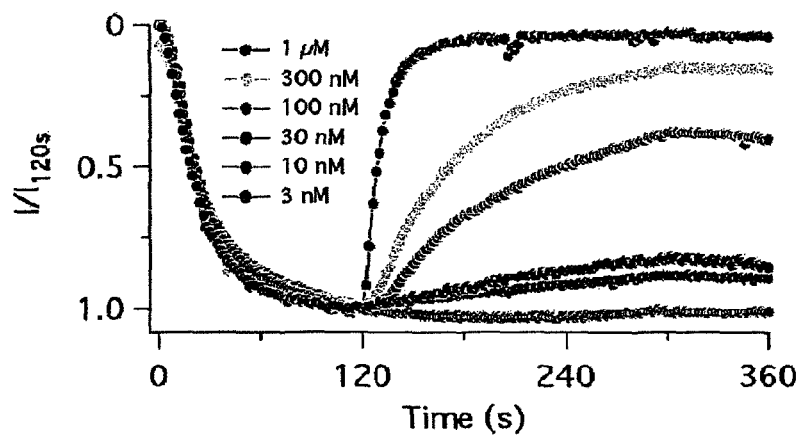
FIG. 1 is a drawing showing an Icrac inhibitory effect of 162AE, wherein the vertical axis shows a relative electric current when the amount of Icrac immediately before acting 162AE (120 sec) is 1, and the horizontal axis shows time (seconds).
Figure 2:
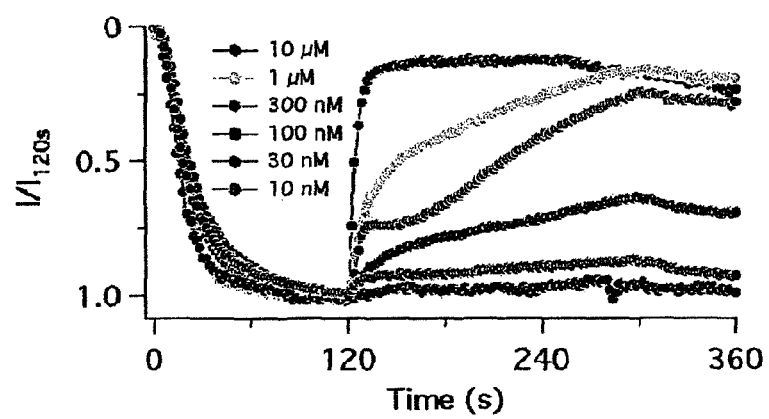
FIG. 2 is a drawing showing an Icrac inhibitory effect of 163AE, and the vertical axis and the horizontal axis show the same as in FIG. 1.
Figure 3:
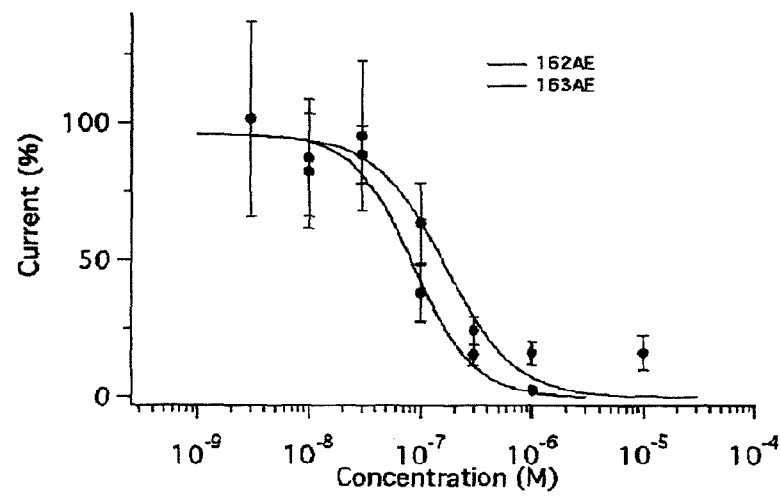
FIG. 3 is a drawing showing a dose inhibition curve relating to the inhibitory effect of 162AE and 163AE on Icrac, wherein the vertical axis shows the amount in percentage of Icrac when the inhibitor was used relative to the amount of Icrac without the inhibitor as 100%, and the horizontal axis shows the concentration (M) of the inhibitor.

In the present invention, the cross-linking of protein means the state where a new bond of protein chain is formed in a molecule or between molecules (covalent bond, ionic bond, coordinate bond, hydrogen bond etc.), and a bridge is built.
In addition, polyglutamine aggregation means formation of assembly of polyglutamine (polymerization and/or specific aggregate).
Abnormal aggregation of polyglutamine is one example of cross-linking abnormalities of protein. An abnormal cross-linking of protein occurs due to abnormal transglutaminase activity that depends on calcium concentration.
The present invention relates to a protein cross-linking inhibitor containing a compound represented by any of the following formulas (1)-(13).

$$R_3\text{—}[\text{—}X\text{—}B(ZR_1)\text{—}Y\text{—}B(ZR_2)\text{—}W\text{—}]_n\text{—}R_4 \quad (1)$$

$$R_3\text{—}[\text{—}X\text{—}B(ZR_1)\text{—}Y\text{—}]_n\text{—}R_4 \quad (2)$$

$$R_3\text{—}[\text{—}B(ZR_1)\text{—}Y\text{—}B(ZR_2)\text{—}W\text{—}]_n\text{—}R_4 \quad (3)$$

$$R_3\text{—}[\text{—}X\text{—}B(ZR_1)\text{—}]_n\text{—}R_4 \quad (4)$$

$$R_3\text{—}[\text{—}B(ZR_2)\text{—}W\text{—}]_n\text{—}R_4 \quad (5)$$

$$R_3\text{—}X\text{—}B(ZR_1)\text{-}T[B(ZR_2)\text{—}W\text{—}R_4]_2 \quad (6)$$

$$R_3\text{—}B(OH)_2 \quad (7)$$

$$R_3\text{—}B(ZR_1)\text{—}X\text{—}B(ZR_2)\text{—}R_4 \quad (8)$$

$$R_3\text{—}B(R_1)\text{—}O\text{—}B(R_2)\text{—}R_4 \quad (9)$$

$$R_3\text{—}[\text{—}X\text{—}B(ZR_1)\text{—}Y\text{—}B(ZR_2)\text{—}]_n\text{—}R_4 \quad (10)$$

$$R_3\text{—}[\text{—}X\text{—}B(ZR_1)\text{—}Y\text{—}B(ZR_2)\text{—}W\text{-}Q\text{-}]_n\text{—}R_4 \quad (11)$$

$$R_3\text{—}[\text{—}O\text{—}X\text{—}B(ZR_1)\text{—}Y\text{—}B(ZR_2)\text{—}W\text{—}]_n\text{—}R_4 \quad (12)$$

$$[R_3\text{—}X\text{—}B(ZR_1)\text{—}Y]_2B(ZR_2) \quad (13)$$

In the formula.
B is a boron atom,
Z is O or S,
$R_1$ and $R_2$ are independently a group selected from H, —$(CH_2)_m$—$NR_5R_6$, —CO—$(CH_2)_m$—$NR_7R_8$, —COCH$(NH_2)$—$R_9$, —CH$_2$CH$(NH_2)$—$R_{10}$, —CHR$_{11}$R$_{12}$, —COCH$(-NR_{13}R_{14})$—$R_{15}$, —COCH$(NH_2)$—$(CH_2)_m$NHCR$_{18}$NH$_2$, —COCH$(NH_2)$—$(CH_2)_m$—COR$_{19}$, —COR$_{20}$, —$(CH_2)_m$—$R_{22}$, —O$(CH_2)_m$NH$_2$, —COCH$(NH_2)$—$(CH_2)_m$—$R_{23}$, —$(CH_2CH_2NH)_2$—$R_{23}$,

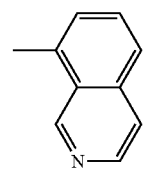

and heterocyclylalkyl, or when $R_1$ and $R_2$ are present in plurality, $R_1$ may be bonded to $R_1$, $R_2$ may be bonded to $R_2$, or $R_1$ may be bonded to $R_2$, $R_5$, $R_6$, $R_7$, $R_8$, $R_9$, $R_{10}$, $R_{11}$, $R_{12}$, $R_{13}$, $R_{14}$, $R_{15}$, $R_{19}$, $R_{20}$ and $R_{22}$ are independently H, or each is a substituted or unsubstituted alkyl, alkenyl, alkynyl, cycloalkyl, cycloalkenyl, aryl, arylalkyl, heterocyclyl, amino, aminoalkylcarbonyl, hydroxy, aromatic group or heterocyclylalkyl, $R_{18}$ is oxo or =NH, Q is a group represented by —$R_{16}$—O—$R_{17}$—, —$R_{21}$—O— or —O— (wherein $R_{16}$, $R_{17}$ and $R_{21}$ mean a single bond or lower alkylene), $R_{23}$ is a fluorescence group, m is an integer of 1 to 5, $R_3$ and $R_4$ are H, OH, $CH_2OH$, $CH_2OCH_2OCH_3$, cyano or aryloxy, or each is a substituted or unsubstituted alkyl or aryl, T is a substituted or unsubstituted aryl, X, Y and W are independently groups containing aromatic series or fatty series, and n is an integer of 1 to 100.

$R_1$ and $R_2$ are preferably independently a group selected from H, —$(CH_2)_m$—$NR_5R_6$, —$CH_2CH(NH_2)$—$R_{10}$, —$CHR_{11}R_{12}$, —$COCH(NH_2)$—$(CH_2)_m$—$COR_{19}$, —$COR_{20}$, —$(CH_2)_m$—$R_{22}$, —$COCH(NH_2)$—$(CH_2)_m$—$R_{23}$ and heterocyclylalkyl.

$R_3$ and $R_4$ are preferably independently H, or a substituted or unsubstituted aryl.

When n is 2 to 100, repeat units may be bonded to each other at both ends, and may be bonded by $R_1$ and $R_2$.

In the present specification, preferable examples of alkyl include methyl, ethyl, propyl, butyl and isomers thereof.

In the present specification, "heterocyclyl" means 5- to 10-membered saturated or unsaturated monocycle containing 1 to 4 hetero atoms (a nitrogen atom, a sulfur atom, an oxygen atom) or a fused ring thereof. For example, pyrrole, imidazole, triazole, tetrazole, pyrazole, pyridine, pyrazine, piperidine, piperazine, pyrrolidine, pyrimidine, pyridazine, furan, pyran, thiophene, thiin, oxazole, isoxazole, thiazole, isothiazole, indole, isoindole, benzofuran, isobenzofuran, benzothiophene, isobenzothiophene, indazole, quinoline, isoquinoline, quinoxaline, quinazoline, cinnoline, benzooxazole, benzothiazole, benzoimidazole, chromene, indoline, isoindoline, dihydrobenzofuran, dihydrobenzothiophene, dihydroindazole, tetrahydroquinoline, tetrahydroisoquinoline, tetrahydroquinoxaline, tetrahydroquinazoline, tetrahydrocinnoline and the like can be mentioned.

Here, heterocyclylalkyl means the aforementioned alkyl moiety substituted by the aforementioned heterocyclyl moiety. Preferable examples of heterocyclylalkyl include 2-pyridylmethyl.

In the present specification, preferable examples of alkenyl include ethenyl, propenyl, butenyl, and isomers thereof and the like.

In the present specification, preferable examples of alkynyl include ethynyl, propynyl, butynyl, and isomers thereof and the like.

In the present specification, "cycloalkyl" means cyclic saturated hydrocarbon. Examples of cycloalkyl include 3- to 10-membered, preferably 5- or 6-membered, cycloalkyl such as cyclopentyl and cyclohexyl.

In the present specification, the "cycloalkenyl" means cyclic unsaturated hydrocarbon having 1 or 2 carbon-carbon double bonds.

Preferable examples of cycloalkenyl include 5- or 6-membered cycloalkenyl, for example, cyclopentenyl, cyclohexenyl and the like.

In the present specification, "aryl" means an atomic group obtained by removing one hydrogen atom from aromatic hydrocarbon. Examples of aryl include a substituted or unsubstituted phenyl, naphthyl, anthryl and the like.

In the present specification, "arylalkyl" means the aforementioned alkyl moiety substituted by 1 or plural aforementioned aryl moieties. Preferable examples of arylalkyl include benzyl and phenylethyl.

In the present specification, aryl of the "aryloxy" is as defined above. Preferable examples of aryloxy include phenoxy.

The aforementioned alkyl, alkenyl, alkynyl, cycloalkyl, cycloalkenyl, aryl, arylalkyl, aryloxy, heterocyclyl and heterocyclylalkyl may have substituent(s) at substitutable position(s). While the number of the substituents is not particularly limited, it is preferably 1 to 3. Specific examples of the substituent include halogen (e.g., fluorine, chlorine), optionally substituted hydroxy (e.g., hydroxy, alkoxy (e.g., methoxy, ethoxy)), optionally substituted methyl (e.g., methyl, trifluoromethyl), optionally substituted amino, carboxyl, optionally substituted phenyl (e.g., phenyl, naphthyl), thiol, optionally substituted amide (e.g., carbonamide), aminoalkylcarbonyl (e.g., aminoethylcarbonyl), thioalkyl (e.g., thiomethyl), and cyano. The optionally substituted amino may have substituent(s) at substitutable position(s). Specific examples of the substituent include aminoalkyl.

In the present specification, "lower alkylene" means straight chain or branched alkylene having a carbon number of 1 to 6, preferably 1 to 4, and preferably includes methylene, ethylene and propylene.

In the present specification, "aminoalkyl" means alkyl having an amino group, preferably aminoethyl.

In the present specification, the "fluorescence group" includes fluorescein such as fluorescein isothiocyanate (FITC) and the like, tetramethylrhodamine (TMeRH), cyanine (Cy2, Cy3, Cy5, Cy7 etc.), fluorescamine and the like. Particularly, FITC and TMeRH are preferable.

In the present specification, the aromatic group is a group derived from aromatic hydrocarbon and heterocycle showing aromatic property, and means a group derived from monocyclic aromatic series (monocyclic aromatic group) and a group derived from polycyclic aromatic series (polycyclic aromatic group). The monocyclic aromatic group means a substituted or unsubstituted phenyl or phenylene group. The phenylene group includes o-, m- and p-phenylene. Examples of the substituent include at least one substituent selected from the group consisting of halogen (e.g., fluorine, chlorine), halogenated $C_1$-$C_4$ alkyl, cyano, hydroxy, hydroxy $C_1$-$C_4$ alkyl, sulfanyl, amino, nitro, mono or di $C_1$-$C_4$ alkylamino, carboxyl, $C_1$-$C_4$ alkylcarbonyl, $C_1$-$C_4$ alkylcarbonyloxy, $C_1$-$C_4$ alkyl, $C_2$-$C_4$ alkenyl, $C_2$-$C_4$ alkynyl, cycloalkyl (as defined above), cycloalkenyl (as defined above), $C_1$-$C_4$ alkylthio, $C_1$-$C_4$ alkoxy, aryl (as defined above), aryloxy (as defined above), amide and $C_1$-$C_4$ alkylamide, thiol and carbamoyl.

In the aforementioned groups, the $C_1$-$C_4$ alkyl moiety means a linear or branched alkyl group having a carbon number of 1 to 4 (e.g., methyl, ethyl, propyl, butyl).

In the aforementioned group, the $C_1$-$C_4$ alkoxy moiety means a linear or branched alkoxy group having a carbon number of 1 to 4 (e.g., methoxy, ethoxy).

In the aforementioned group, the $C_2$-$C_4$ alkenyl moiety means a linear or branched alkenyl group having a carbon number of 1 to 4 (e.g., ethenyl, propenyl, butenyl).

In the aforementioned group, the $C_2$-$C_4$ alkynyl moiety means a linear or branched alkynyl group having a carbon number of 1 to 4 (e.g., ethynyl, propynyl, butynyl).

In the aforementioned group, the aryl moiety is as defined above.

In the aforementioned group, examples of the substituted phenyl include, but are not limited to, mono, di or trifluorophenyl, methoxyphenyl, tolyl, xylyl, o-chlorotolyl, trifluoromethylphenyl, methoxyphenyl, tolyl, xylyl, o-chlorotolyl, trifluoromethylphenyl, 2-methoxy-5-fluorophenyl, hydroxymethylphenyl, phenoxyphenyl and the like. Examples of the substituted phenylene include, but are not limited to, 5-methyl-m-phenylene, 5-methyl-p-phenylene and the like. The polycyclic aromatic group means a fused polycyclic hydrocarbon group comprised of a fused ring of 2 to 6, preferably 2 or 3, of 5-membered and/or 6-membered monocyclic carbocycles. Examples include, but are not limited to, substituted or unsubstituted naphthyl, anthryl, phenanthryl, indenyl, fluorenyl and the like. Here, examples of the substituent include the same substituents as recited above. Examples of the aromatic heterocyclic group include a 5-membered ring containing one hetero atom such as a furanyl group, a thiophenyl group, a pyrrolyl group and the like, a 6-membered ring containing one hetero atom such as a pyridinyl group and the like, a 5-membered ring containing two hetero atoms such as an oxazolyl group, a thiazolyl group and the like, a 6-membered ring containing two hetero atoms such as a pyridazinyl group, a pyrimidinyl group and the like, and a 5- to 7-membered ring containing at least one hetero atom, a bicyclic condensed hetero group containing one hetero atom such as an indolyl group, a quinolinyl group and the like, a bicyclic condensed hetero group containing two hetero atoms such as a quinoxalinyl group and the like, a tricyclic condensed hetero group containing one hetero atom such as an acrydinyl group and the like, a bicyclic condensed hetero group containing two hetero atoms such as an indazolyl group and the like, and a polycyclic condensed hetero group containing at least one hetero atom, and the like.

In the present specification, a group of aliphatic series (aliphatic group) is a group derived from saturated hydrocarbon (alkane) and unsaturated hydrocarbon (alkene, alkyne).

Particularly preferably, X, Y and W are groups containing aromatic series or aliphatic series, monocyclic aromatic groups, such as

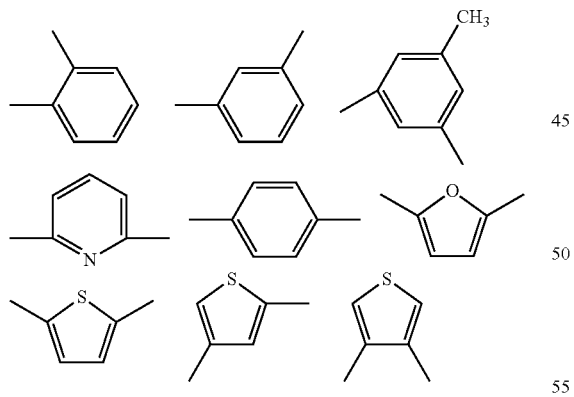

condensed aromatic groups having two or more rings, such as

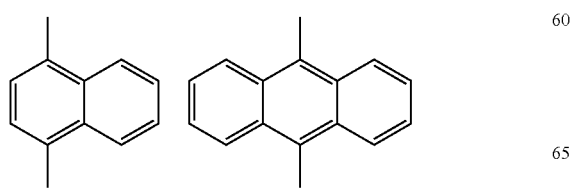

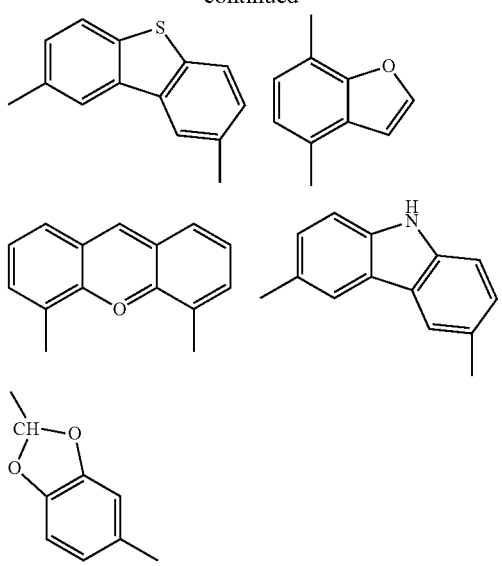

aromatic groups wherein two aromatic groups are directly bonded, such as

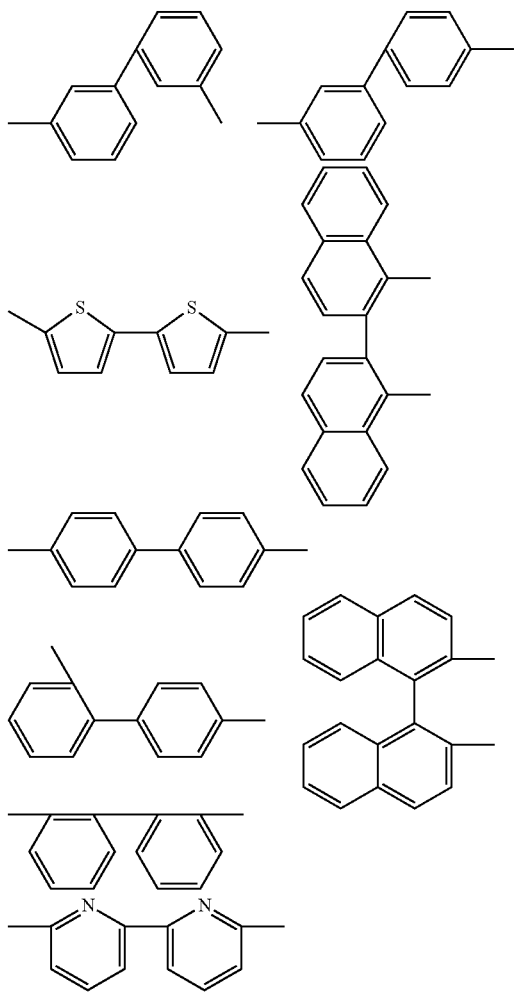

substituted or unsubstituted aromatic groups wherein two aromatic groups are bonded via O, $CH_2$, S, $SO_2$, $CH_2OCH_2$, $OCH_2$, $OCH_2CH_2OCH_2$, $OCH_2OCH_2CH_2$, $CH_2OCH_2CH_2$, $CH_2OCH_2CH_2OCH_2$ and the like, such as

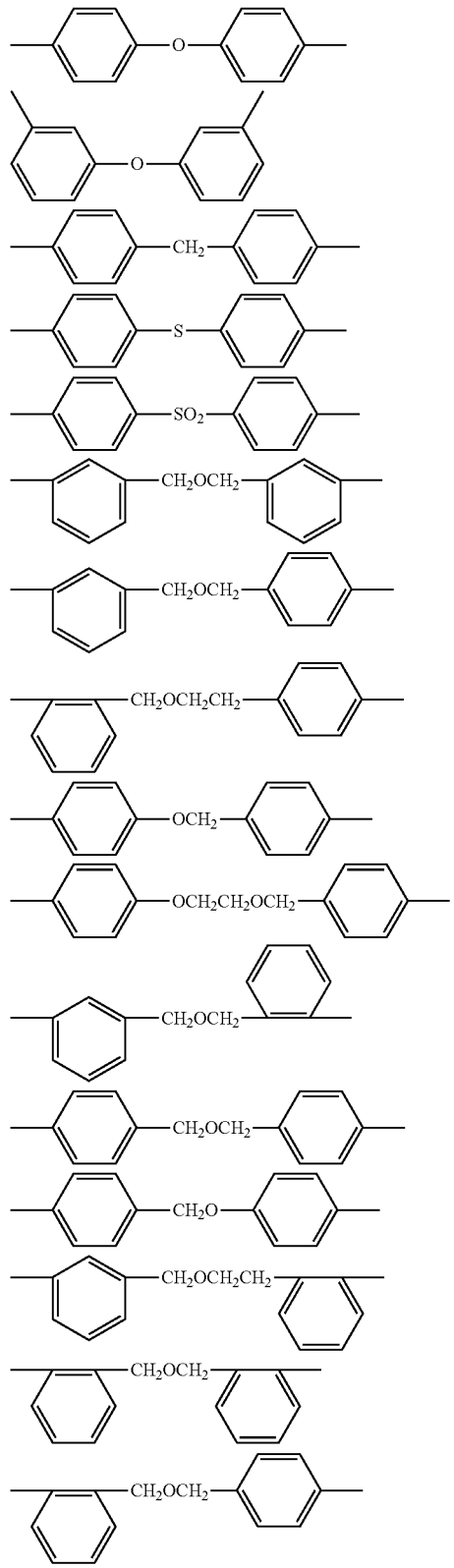

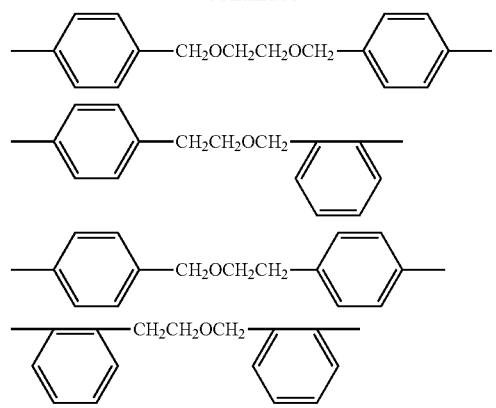

and substituted or unsubstituted aliphatic groups such as $(CH_2)_4$ can be mentioned.

More preferably, as X, Y, W, monocyclic aromatic groups, such as

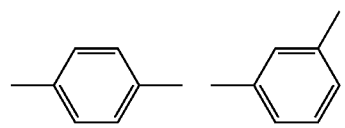

condensed aromatic groups having two or more rings, such as

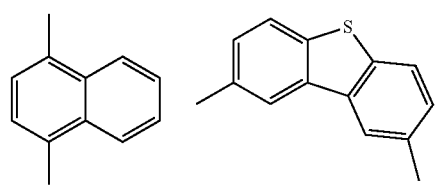

aromatic groups wherein two aromatic groups are directly bonded, such as

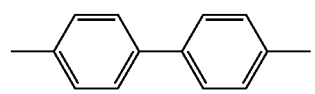

substituted or unsubstituted aromatic groups wherein an aromatic group is bonded via O, $CH_2O$, $CH_2OCH_2$ and the like, such as

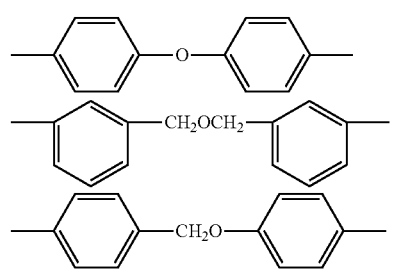

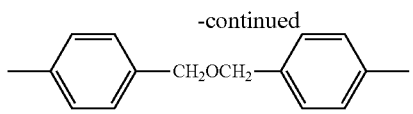

can be mentioned.

However the compound of the present invention excludes a compound represented by the following formula (Ia)

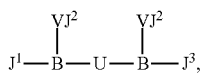

and a compound represented by the following formula (Ib)

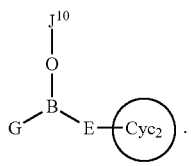

In the formula (Ia), B is a boron atom, and V is an oxygen or sulfur atom. $J^1$ and $J^3$ are each independently a monocyclic aromatic group, a polycyclic aromatic group, or a heterocyclic group containing at least one hetero atom selected from an oxygen atom, a nitrogen atom and a sulfur atom.

$J^2$ is a hydrogen atom; —$(CH_2)_D$—$NJ^4J^5$ wherein D is an integer of 1-4, $J^4$ and $J^5$ are independently a hydrogen atom, or $C_{1-4}$ alkyl substituted or unsubstituted by an amino group, a mono or di-$C_{1-4}$ alkylamino group or a phenyl group, or $J^4$ and $J^5$ form, together with a nitrogen atom bonded thereto, a 5-membered or 6-membered cyclo ring); —CO—$(CH_2)J^5$ wherein D, $J^4$ and $J^5$ are as defined above); —COCH($NH_2$)$J^6$ wherein $J^6$ is an amino acid residue, or —$(CH_2)_{D'}NH_2$ wherein D' is an integer of 1-3; —CH$J^7J^6$ wherein $J^7$ and $J^8$ are independently an amino group, $C_{1-4}$ alkyl substituted or unsubstituted by a mono or di($C_{1-4}$ alkyl substituted or unsubstituted by an amino group)amino group or phenyl group, or phenyl substituted by pyridyl or $C_{1-3}$ alkoxy group; —$CH_2CH(NH_2)$-$J^9$ wherein $J^9$ is $C_{1-4}$ alkyl substituted by phenyl or phenyl); quinolyl or isoquinolyl substituted by a $C_{1-4}$ alkyl group; or $C_{1-4}$ alkyl substituted by a pyridyl group, a piperidino group or a pyrrolidinyl group.

U is a monocyclic aromatic group, a polycyclic aromatic group or a heterocyclic group, which is the same as or different from $J^1$ and $J^3$, or a bifunctional group having a monocyclic aromatic group, a polycyclic aromatic group or a heterocyclic group bonded to both sides thereof via a group selected from the group consisting of a single bond, O, $CH_2$, S, $SO_2$, $CH_2OCH_2$, $OCH_2$, $OCH_2CH_2OCH_2$, $OCH_2OCH_2CH_2$ and $CH_2OCH_2CH_2$.

A compound represented by the formula (Ia) to be excluded from the compound of the present invention corresponds to a compound represented by the formula (I) disclosed in WO2007/061074. Therefore, the definition of each substituent (functional group) in the formula (Ia) follows the definition described in the publication.

In the formula (Ib), $J^{10}$ is any of the following (1)-(6).
(1) a hydrogen atom.
(2) —$(CH_2)_{D''}$—$NJ^{11}J^{12}$.
In the group, D" is an integer of 1-3, $J^{11}$ and $J^{12}$ are each independently a hydrogen atom, $C_{1-4}$ alkyl, $C_{5-6}$ monocyclic carbocycle, $C_{1-4}$ alkyl substituted by $C_{5-6}$ monocyclic carbocycle, or 5- or 6-membered monocyclic heterocycle.

The carbon atom in —$(CH_2)_{D''}$— is optionally substituted by 1 or 2 $J^{13}$, and the carbocycle and heterocycle are optionally substituted by 1 or 2 $J^{16}$. $J^{13}$ is (a) $C_{1-8}$ alkyl, (b) carboxyl, (c) alkoxycarbonyl, (d) keto, (e) $C_{5-6}$ monocyclic carbocycle, (f) guanidino($C_{1-2}$)alkyl, (g) $C_{1-6}$ alkyl substituted by $C_{5-6}$ monocyclic carbocycle, (h) $C_{1-2}$ alkyl substituted by 4-chlorophenoxy, or (i) $C_{1-4}$ alkyl substituted by di($C_{1-4}$ alkylamino.

(3) $C_{1-6}$ alkyl or $C_{2-6}$ alkenyl substituted by $C_{5-6}$ monocyclic carbo cycle.

The carbocycle is optionally substituted by 1 to 5 $J^{16}$, and the $C_{1-6}$ alkyl or $C_{2-6}$ alkenyl is optionally substituted by 1 or 2 $J^{19}$.

(4) $C_{1-6}$ alkyl or $C_{2-6}$ alkenyl substituted by 5- or 6-membered monocyclic heterocycle.

The heterocycle is optionally substituted by 1 to 5 $J^{16}$, and the $C_{1-6}$ alkyl and $C_{2-6}$ alkenyl are optionally substituted by 1 or 2 $J^{19}$. $J^{19}$ is $C_{1-4}$ alkyl or $C_{2-4}$ alkenyl.

(5) —$CHJ^{14}J^{15}$.

In the group, $J^{14}$ and $J^{15}$ are each independently
(i) $C_{5-6}$ monocyclic carbocycle,
(ii) 5- or 6-membered monocyclic heterocycle,
(iii) $C_{1-6}$ alkyl or $C_{2-6}$ alkenyl substituted by $C_{5-6}$ monocyclic carbocycle, or
(iv) $C_{1-6}$ alkyl or $C_{2-6}$ alkenyl substituted by 5- or 6-membered monocyclic heterocycle.

Moreover, the carbocycle and heterocycle are optionally substituted by 1 to 5 $J^{16}$.

(6) 5,6,7,8-tetrahydroquinolin-8-yl.

$J^{16}$ is (a) $C_{1-4}$ alkyl, (b) $C_{1-4}$ alkoxy, (c) a halogen atom, (d) —$CF_3$, (e) nitro, (f) $C_{5-6}$ monocyclic carbocycle, (g) $C_{1-4}$ alkyl substituted by $C_{5-6}$ monocyclic carbocycle, (h) amino, (i) —NHCO($C_{1-4}$ alkyl), or (j) $C_{1-4}$ alkoxycarbonyl.

G is $Cyc_1$ or hydroxy.

$Cyc_1$ is $C_{5-10}$ monocyclic or bicyclic carbocycle, or 5- to 10-membered monocyclic or bicyclic heterocycle, the carbocycle and heterocycle are optionally substituted by 1 to 5 $J^{17}$.

$Cyc_2$ is $C_{5-10}$ monocyclic or bicyclic carbocycle, or 5- to 10-membered monocyclic or bicyclic heterocycle. The carbocycle and heterocycle are optionally substituted by 1 to 5 $J^n$.

$J^{17}$ and $J^{18}$ are each independently
(a) $C_{1-4}$ alkyl,
(b) $C_{2-4}$ alkenyl,
(c) $C_{1-4}$ alkoxy,
(d) a halogen atom,
(e) —$CF_3$,
(f) alkylthio,
(g) amino,
(h) ($C_{1-4}$ alkyl)amino,
(i) di($C_{1-4}$ alkyl)amino,
(j) formyl,
(k) phenyl,
(l) phenoxy,
(m) hydroxy ($C_{1-2}$) alkyl,
(n) ($C_{5-10}$ monocyclic or bicyclic carbocycle)-O—($C_{1-2}$) alkyl,
(o) $C_{1-4}$ alkoxycarbonylvinyl,
(p) $C_{1-2}$ alkyl substituted by group(s) selected from —O—($C_{1-2}$ alkylene)-phenyl (said phenyl is optionally substituted by 1 to 3 $C_{1-4}$ alkoxy), —O—CONH-phenyl (said phenyl is optionally substituted by 1 to 3 $C_{1-4}$ alkyl, nitro or $C_{1-4}$ alkoxycarbonyl), or —O—CONH—($C_{1-4}$)alkyl (said alkyl is optionally substituted by 1 to 3 $C_{1-4}$ alkyl, carboxyl or $C_{1-4}$ alkoxycarbonyl), (q) phenylthio,
(r) —CON(C$_{1-4}$ alkyl)$_2$,
(s) —SO$_2$N(C$_{1-4}$ alkyl)$_2$,
(t) C$_{1-4}$ alkoxy (C$_{1-2}$) alkyl,
(u) C$_{1-4}$ alkoxycarbonyloxy (C$_{1-2}$) alkyl,

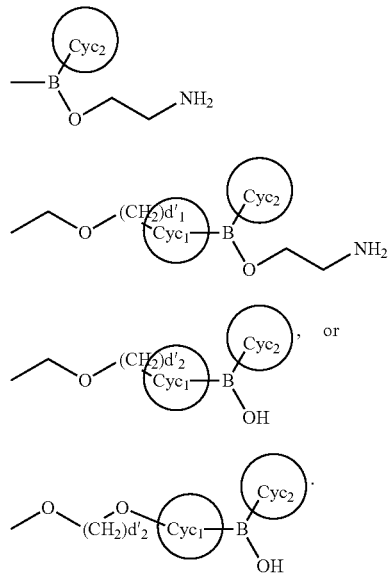

The carbocycle, phenyl, Cyc$_1$ and Cyc$_2$ in J$^{17}$ and J$^{18}$ are optionally substituted by 1 or 2 J$^{16}$, or J$^{17}$ and J$^{18}$ optionally show —O—, and further, J$^{18}$ and J$^{19}$ optionally show a single bond.

d'$_1$ is an integer of 1-4, d'$_2$ is an integer of 1-4, and d'$_3$ is an integer of 1-4. E is a single bond or C$_{1-4}$ alkylene substituted or unsubstituted by C$_{5-6}$ monocyclic carbocycle.

A compound represented by the formula (Ib) to be excluded from the compound of the present invention corresponds to a compound represented by the formula (I) disclosed in WO03/033002. Therefore, the definition of each substituent (functional group) in the formula (Ib) follows the definition described in the publication.

The compounds of the aforementioned (1)-(13) in the present invention specifically include the following.
2-aminoethylthio bis(4-chloro-2-fluorophenyl)borane
(4-(phenylglutamineboryl)phenyl) (4'-(phenylhydroxyboryl)phenyl)ether
bis(4,4'-(phenylhydroxyboryl)phenyl)ether
poly(4,4'-biphenylene N-methylaminoethoxyborane)
bis(4,4'-(phenylaminoethoxyboryl)phenyl)ether
(4-(phenylasparagineboryl)phenyl)(4'-(phenylhydroxyboryl)phenyl)ether
bis(3,3'-(phenylhydroxyboryl)benzyl)ether
bis(3,3'-(phenylaminoethoxyboryl)benzyl)ether
4,4'(phenyl-2-aminoethylthioboryl)diphenyl
4,4'(phenyl-2-aminoethoxyboryl)diphenyl
poly(2,5-dimethoxy-4-phenylborinic acid)
poly(aminoethyl-2,5-dimethoxy-4-phenylborinate)
poly(1,4-phenylenemethyleneoxymethylene 1,4-phenylene hydroxyborane)
poly(1,4-phenylenemethyleneoxymethylene 1,4-phenylene 2-aminoethoxyborane)
poly(4,4'-phenylenemethyleneoxymethylene 4,4'-phenylene-dimethylaminoethoxyborinic acid)
poly(1,4-phenylenemethyleneoxymethylene 1,4-phenylene 2-piperidinomethoxyborane)
poly(1,4-phenyleneoxy-1,4-phenylenehydroxyborane)
poly(aminoethoxyboryldiphenylether)
poly(isopropoxyboryldiphenylether)
poly(4,4'-diphenylether dimethylaminoethoxyborane)
poly(4,4'-diphenylether-2-pyridyl-4-trifluoromethylphenyl-methoxyborane)
poly(4,4'-diphenylether-2-aminoethylthioborane)
poly(phenylenemethyleneoxyphenylenehydroxyborane)
poly(phenylenemethyleneoxyphenyleneaminoethoxyborane)
poly(phenylenemethyleneoxyphenyleneaminoethylthioborane)
poly(phenylenemethyleneoxyphenylenedimethylaminoethoxyborane)
poly(4'-phenylhydroxyboranephenylenemethyleneoxyphenylenehydroxyborane phenylenemethyleneoxymethylene)
poly(phenylenemethyleneoxyphenyleneaminoethoxyboranephenylene-methyleneoxymethylenephenylene aminoethoxyborane)
poly(phenylenemethyleneoxyphenylenemethylaminoethoxyborane-phenylenemethyleneoxymethylenephenylenemethylaminoethoxyborane)
poly(4,4'-biphenylene-hydroxyborane 1,4-phenylenemethyleneoxymethylenephenylenehydroxyborane)
poly(4,4'-biphenylene 2-aminoethoxyborane 1,4-phenylenemethyleneoxymethylene 1,4-phenylene 2-aminoethoxyborane)
di(3-chloro-4-methylphenyl)-2-aminoethylthioborane
poly(2,5-dimethoxy-4-phenylene-hydroxyborane-1,4-phenylenehydroxyborane)
polyaminoethyl(2,5-dimethoxy-4-phenylene)aminoethoxyboryl(1,4-phenylene)borinate
poly(2-pyridylmethyl(2,5-dimethoxy-4-phenylene) 2-pyridylmethoxyborane-(1,4-phenylene)borinate)
poly(4,4'-biphenylene-hydroxyborane 4,4'-diphenylether hydroxyborane)
poly(4,4'-biphenylene-dimethylaminoethoxyborane 4,4'-diphenylether dimethylaminoethoxyborane)
poly(4,4'-biphenylene-aminoethoxyborane-4,4'-diphenylether aminoethoxyborane)
poly(phenyleneaminoethoxyborane diphenylether-aminoethoxyborane)
poly(phenyleneaminoethylthioborane diphenylether-aminoethylthioborane)
poly(phenylene 2-piperazinomethoxyborane diphenylether 2-piperidinomethoxyborane)
poly(methylaminoethoxyborylphenylene methylaminoethoxyboryldiphenylether)
poly(pyrrolidinomethoxyborylphenylene pyrrolidinomethoxyboryldiphenylether)
poly(aminoethylaminoethoxyborylphenylene aminoethylaminoethoxyboryldiphenylether)
poly(metaphenylene-hydroxyborane-4,4'-diphenyletherhydroxyborane)
poly(metaphenylene-2-piperidinemethoxyborane-4,4'-diphenylether-2-piperidinemethoxyborane)
poly(metaphenylene-aminoethoxyborane-4,4'-diphenylether aminoethoxyborane)
poly(mataphenylene-methylaminoethoxyborane-4,4'-diphenylethermethylaminoethoxyborane)
poly(metaphenylene-2-dimethylaminoethoxyborane-4,4'-diphenylether-2-dimethylaminoethoxyborane)

poly(metaphenylene-2-pyridyl-trifluoromethylphenyl-methoxyborane-4,4'-diphenylether-2-pyridyl-trifluoromethylphenylmethoxyborane)
poly(metaphenylene-aminoethylthioborane-4,4'-diphenylether-aminoethylthioborane)
poly(4,4'-diphenyletherhydroxyborane phenylenemethyleneoxyphenylenehydroxyborane)
poly(phenylenemethyleneoxyphenylene-aminoethoxyborane-4,4'-diphenyletheraminoethoxyborane)
poly(phenyleneoxyphenylene-2-pyrrolidinemethoxyboryl-phenylenemethyleneoxyphenylene-2-pyrrolidinemethoxyborane)
poly(phenylenemethyleneoxyphenylene-dimethylaminoethoxyborane-4,4'-diphenylether dimethylaminoethoxyborane)
poly(phenylenemethyleneoxyphenylene-2-pyridylmethoxyborane-4,4'-diphenylether-2-pyridylmethoxyborane)
poly(4,4'-biphenylene-aminoethoxyborane-1,4-phenylenemethyleneoxy-1,4-phenylene-aminoethoxyborane)
poly(4,4'-biphenylene-dimethylaminoethoxyborane-1,4-phenylene-methyleneoxyphenylenedimethylaminoethoxyborane)
poly(4,4'-biphenylene-2-pyridylmethoxyborane-1,4-phenylene-methyleneoxy-1,4-phenylene-2-pyridylmethoxyborane)
poly(4,4'-biphenylene-2-hydroxyethylaminoethoxyborane-1,4-phenylene-methyleneoxy-1,4-phenylene-2-hydroxyethylaminoethoxyborane)
poly(4,4'-phenylene-methyleneoxymethylene-phenylene-hydroxyborane-4,4'-phenyleneoxyphenyleneborinic acid)
poly(phenylene-methyleneoxymethylene-phenylene-aminoethoxyborane-phenyleneoxyphenyleneaminoethoxyborane)
poly(phenylene methyleneoxymethylene phenylene dimethylaminoethoxyborane phenylene oxy phenylene dimethylaminoethoxyborane)
poly(phenylene methyleneoxymethylene phenylene aminoethylthioborane phenylene oxy phenylene aminoethylthioborane)
poly(diphenylene-methylaminoethoxyboryl-1,4-phenylene-methyleneoxymethylenephenylene-methylaminoethoxyborane)
poly(1,4-phenylene-methyleneoxymethylenephenylenemethylaminoethoxyborane-1,4-phenylene-methylaminoethoxyborane)
poly(1,4-phenylene-methyleneoxymethylenephenylene-aminoethylaminoethoxyborane-1,4-phenylene-aminoethylaminoethoxyborane)
polytetramethyleneborinic acid
2-dimethylaminoethyl bis(4-trifluoromethylphenyl)borinate
1,3-dimethylaminopropyl bis(3-chloro-4-methylphenyl)borinate
di(3-chloro-4-methylphenyl)(2,3-diaminopropionate-O,N)borane
di(3-chloro-4-methylphenyl)piperazinoethoxyborane
di(3-chloro-4-methylphenyl)piperidinoethoxyborane
di(3-chloro-4-methylphenyl)-2-piperidinoethoxyborane
bis(4-trifluoromethylphenyl)borinic acid
di(3-fluoro-4-chlorophenyl)borinic acid
2-aminoethyl-bis(3-chloro-4-fluorophenyl)borinate
2-dimethylaminoethyl bis(3-chloro-4-fluorophenyl)borinate
bis(4-chloro-2-fluorophenyl)borinic acid
bis(3,4-difluorophenyl)borinic acid
bis(3,4,5-trifluorophenyl)borinic acid
bis(2,4-difluorophenyl)borinic acid
bis(3-fluoro-4-chlorophenyl)borinic acid
2-aminoethyl bis(4-chloro-2-fluorophenyl)borinate
poly(4,4'-biphenylhydroxyborane)
2-aminoethyl bis(3-chloro-4-fluorophenyl)borinate
2-aminoethyl bis(3,4-difluorophenyl)borinate
2-amino-1-phenylethyl bis(3,4-difluorophenyl)borinate
aminoethyl bis(3,4,5-trifluorophenyl)borinate
2-pyridylmethyl bis(3,4,5-trifluorophenyl)borinate
aminoethyl bis(3,5-difluorophenyl)borinate
dimethylaminoethyl bis(3,5-difluorophenyl)borinate
aminoethyl bis(4-chloro-3-fluorophenyl)borinate
dimethylaminoethyl bis(4-chloro-3-fluorophenyl)borinate
di(3-fluoro-4-chlorophenyl)(2,4-diaminolactonate-O,N)borane
di(3-fluoro-4-chlorophenyl)(glutaminate-O,N)borane
bis(3-chloro-5-fluorophenyl)borinic acid
bis(3-chloro-6-fluorophenyl)borinic acid
aminoethyl bis(3-chloro-5-fluorophenyl)borinate
aminoethyl bis(3-chloro-6-fluorophenyl)borinate
methylaminoethyl bis(3-chloro-6-fluorophenyl)borinate
bis(4-cyanophenyl)borinic acid
aminoethyl bis(4-cyanophenyl)borinate
2-pyridylmethyl bis(4-cyanophenyl)borinate
benzylaminoethyl bis(4-cyanophenyl)borinate
2-aminoethylthio bis(4-cyanophenyl)borane
secondary-butyl phenyl borinic acid
normal-butyl phenyl borinic acid
tertiary-butyl phenyl borinic acid
aminoethyl secondary-butyl phenylborinate
aminoethyl tertiary-butyl phenylborinate
aminoethyl normal-butyl phenylborinate
1,4-bis(hydroxyphenylboryl)butane
4-hydroxybutylphenylborinic acid
bis(4-chlorophenyl)borinic acid
bis(di(3-chloro-4-methylphenyl)boryloxyethyl)piperazine
bis(3-chloro-4-methylphenyl 2-pyridylmethoxyborylphenyl)ether
1,4-bis(phenyl-2-aminoethoxyboryl)benzene
1,3-bis(phenyl-2-aminoethoxyboryl)benzene
1,3-bis(phenylhydroxyboryl)benzene
diphenyl(argininate-O,N)borane
diphenyl(glutaminate-O,N)borane
(2-phenylhydroxyborylbenzyl)(3-(phenylhydroxyboryl)benzyl)ether
bis(3-chloro-4-methylphenyl hydroxyborylbenzyl)ether
bis(phenyl 2-pyridyl-4-methoxyphenylmethoxyborylbenzyl)ether
bis(3-chloro-4-methylphenyl) 2-pyridyl-4-methoxyphenylmethoxyborane
1,4-bis(3-chloro-4-methylphenyl-2-aminoethoxyboryl)benzene
di((phenylglycine-O,N boryl)phenyl)ether
1,3,5-tri(phenylhydroxyboryl)benzene
bis((4,4'-phenylaminoethoxyboryl)benzyl)ether
1,3,5-tri(2-pyridyl-4-trifluoromethylphenylmethoxyphenylboryl)benzene
(2-pyridyl-phenylmethoxyphenylboryl 2-benzyl)ether
(2-pyridyl-4-trifluoromethylphenylmethoxyphenylboryl 2-benzyl)ether
1,4-bis(phenylhydroxyboryl)naphthalene diphenyl(asparaginate-O,N)borane
bis((4,4'-phenylhydroxyboryl)benzyl)ether
bis(2-pyridyl-4-trifluoromethylphenylmethoxyphenylboryl 4-benzyl)ether
bis(4-chloro-3-methylphenylhydroxyboryl 4-benzyl)ether
4,4'-phenylhydroxyboryl 4-biphenyl
bis(4,4'-(1-naphthylhydroxyboryl)benzyl)ether
bis(4-fluorophenylhydroxyboryl 4-benzyl)ether
bis(4-trifluoromethylphenylhydroxyboryl 4-benzyl)ether bis(3-chloro-4-methylphenylhydroxyboryl 4-benzyl)ether
(3-chloro-4-fluorophenyl)boronic acid
1,4-bis(phenyl-2-aminoethoxyboryl) 2-methylbenzene 1,2-bis(phenylhydroxyboryl)benzene
bis(2,2'-(phenyl-2-aminoethoxyboryl)benzyl)ether
diphenyl-2-aminophenylthioborane
2-aminoethylthiodiphenylborane
di(4,4'-phenyldimethylaminoethoxyboryl)benzylether
poly(4,4'-biphenylene-2-pyridyl-4-trifluoromethylphenyl-methoxyborane
4,4'-diphenylether 2-pyridyl-4-trifluoromethoxyborane)
diphenyl 2-aminoethylaminoethyl borinate
di(trifluoromethylphenyl) 2-pyridinomethylborinate
di(3-chloro-6-methyl-phenyl)(argininate-O,N)borane
poly(phenylenemethyleneoxyphenyle-neaminoethoxyborane)
poly(phenylenemethyleneoxyphenyle-neaminoethylthioborane)
dibutyl(alanine-O,N)borane
di(3-chloro-6-methyl-phenyl)(citrullinate-O,N)borane
FITC aminoethylaminoethyl diphenylborinate
tetramethylrhodamine aminoethylaminoethyl diphenylborinate
di(3-chloro-4-methylphenyl)N-methylpiperidinomethyl-borinate
di(3-chloro-6-methylphenyl)benzylaminoethylborinate
poly(4,4'-biphenylene-methylaminoethoxyborane 1,4-phenylene methyleneoxymethylenephenylene-methylaminoethoxyborane)
(4-(phenyl-dimethylaminoethoxyboryl)phenyl)-(4'-(methoxymethoxymethylphenyl-dimethylaminoethoxyboryl) phenyl)ether
(4-(phenyl-N-methylaminoethoxyboryl)phenyl)-(4'-(methoxymethoxymethylphenyl-N-methylaminoethoxyboryl) phenyl)ether
di((phenylglycine-O,N boryl)phenyl)ether
diphenyl(glycylglutamine-O,N)borane
di(3-chloro-6-methylphenyl)borinic acid
bis(3,3'(phenyldimethylaminoethoxyboryl)benzyl)ether
(3,3'-(phenylpiperazino-O,O-ethoxyboryl)benzyl)ether
diphenyl(2,3-diaminopropionate-O,N)borane
diphenyl(tetramethylrhodamine 2,3-diaminopropionate-O, N)borane
diphenyl(tetramethylrhodamine 2,6-diaminocapronate-O,N) borane
diphenyl(FITC-2,6-diaminocapronate-O,N)borane
diphenyl(2,3-diaminobutyrate-O,N)borane
diphenyl(2,5-diaminopentanate-O,N)borane
di(3-chloro-4-methylphenyl)(anthranate-O,N)borane
di(trifluoromethylphenyl) 2-aminoethylborinate
di(3-chloro-4-methylphenyl)(glutaminate-O,N)borane
dibutyl(asparagine-O,N)borane
di(4-(phenyl-2-pyridylmethoxyboryl)benzyl)ether
di(1-(pyridin-2-yl)-1-(4-methoxyphenyl)methyl-phenyl-borylbenzyl)ether
bis((4,4'-phenylhydroxyboryl)benzyloxybenzyl)hydroxyborane
di(trifluoromethylphenyl) 2-propylaminoethylborinate
bis((4,4'-phenylaminoethoxyboryl)benzyloxybenzyl)aminoethoxyborane
bis((4,4'-phenyl methylaminoethoxyboryl)benzyloxybenzyl)methylaminoethoxyborane
bis((4,4'-phenyldimethylaminoethoxyboryl)benzyloxybenzyl)dimethylaminoethoxyborane
bis((4,4'-phenyl 2-pyridyl-4-trifluoromethylphenylmethoxyboryl)benzyloxybenzyl) 2-pyridyl-4-trifluoromethyl phenylmethoxyborane
diphenyl(2-piperazine-3-carboxyamide-carboxy)borane
diphenyl(methionate-O,N)borane
phenyl 3-piperidinooxyboryl phenylether
4,4'-(phenyl piperazino-O,O-ethoxyboryl)phenylether
4,4'-(phenyl piperazino-O,O-ethoxyboryl)benzylether
bis(4,4'-(phenyldimethylaminoethoxyboryl)phenyl)ether
bis(3,3'-(phenylbenzylaminoethoxyboryl)phenyl)ether
di(3-chloro-2-methylphenyl)borinic acid
4,4'-di((3-chloro-4-methylphenyl 2-hydroxyboryl)phenyl) ether
phenyl naphthyl 2-pyridylmethylborinate
phenyl naphthyl dimethylaminoethylborinate
phenyl naphthyl benzylaminoethylborinate
bis(4,4'-(phenyl 2-amino-2-benzylethoxyboryl)benzyl)ether
bis(3,3'-(phenyldimethylaminoethoxyboryl)benzyl)ether
di(3-chloro-4-methylphenyl)dimethylaminoethylborinate
di(3-chloro-4-methylphenyl)-2-benzyl-2-aminoethylborinate
di(3-chloro-4-methylphenyl)1-phenyl 2-aminoethylborinate
di(3-chloro-4-methylphenyl)butylaminoethyl borinate
di(3-chloro-4-methylphenyl)benzylaminoethyl borinate
diphenyl(R) 2-benzyl-2-aminoethyl borinate
diphenyl(S) 2-benzyl-2-aminoethyl borinate
di(3-chloro-4-methylphenyl) 1-phenylaminoethylborinate
di(3-chloro-4-methylphenyl)pyridylmethylborinate
di(3-chloro-4-methylphenyl)borinic acid anhydride
diphenylborinic acid anhydride
diphenyl(picolinate-O,N)borane
diphenyl(2-aminophenyl carboxylate-O,N)borane
di(3-chloro-4-methylphenyl) 2-aminophenylborinate
di(3-chloro-4-methylphenyl)(2-pyridine carboxylate-O,N) borane
poly(4,4'-diphenylether glutamine-O,N)borane
poly(4,4'-diphenyl glutamine-O,N borane)
diphenyl 1-(2-aminobenzyl) 1-phenylmethylborinate
di(3-chloro-4-methylphenyl) 1-(2-aminobenzyl) 1-phenylmethylborinate
diphenyl(2-aminohexanecarboxylate-O,N)borane
di(3-chloro-4-methylphenyl)(norloysinate-O,N)borane
diphenyl 2-aminobutylborinate
di(3-chloro-4-methylphenyl) 2-aminobutylborinate
di(trifluoromethylphenyl)borinic acid
di(3-chloro-4-methylphenyl)borinic acid
di(trifluoromethylphenyl) 2-aminoethylborinate
di(trifluoromethylphenyl) 2-dimethylaminoethylborinate
di(4-chloro-3-fluoro-phenyl) 2-aminoethylborinate
di(4-chloro-2-fluorophenyl) 2,3-diamino-2-propyl-borinate
di(4-chloro-3-fluorophenyl) 2-amino-2-methyl-propyl-borinate
di(4-chloro-3-fluorophenyl) 2-phenylaminoethyl borinate
di(4-chloro-3-fluorophenyl) 2-amino-3-hydroxybutyl borinate
bis(diphenyl piperazino-O,O-ethoxyborane)
4-((2-aminoethoxy)phenylboryl)benzyl-4'-((2-aminoethoxy)phenylboryl)phenethylether
di(3-chlorophenyl)borinic acid
di(5-chloro-2-methylphenyl) 2-piperidinomethylborinate
di((5-chloro-2-methylphenyl)hydroxyborylphenyl)ether
di(5-chloro-2-methylphenyl) 2-aminoethylborinate
diphenyl(ornithine-O,N)borane
di(5-chloro-2-methylphenyl) 2-butylaminoethylborinate
di(3-chloro-4-methylphenyl) 2-piperidinomethylborinate
di(3-chloro-4-methylphenyl) 2-piperidinoethylborinate
4,4'-((2-aminoethoxy)(3-chloro-4-methylphenyl)boryl) diphenylether
bis(4,4'-(phenyldimethylaminoethoxyboryl)phenyl)ether
bis(3-chloro-4-methylphenyl hydroxyborylphenyl)ether 1,4-bis(phenylhydroxyboryl)benzene
di(2-thiophene)borinic acid
diphenyl(glycinate-O,N)borane
diphenyl(serinate-O,N)borane
diphenyl(glutaminate-O,N)borane
diphenyl(asparaginate-O,N)borane
diphenyl(alaninate-O,N)borane
diphenyl(phenylalaninate-O,N)borane
diphenyl(tryptophanate-O,N)borane
diphenyl(leucinate-O,N)borane
diphenyl(isoleucinate-O,N)borane
diphenyl(2,4-diaminolactonate-O,N)borane
diphenyl(tyrosinate-O,N)borane
diphenyl(threoninate-O,N)borane
diphenyl(cysteinate-O,N)borane
diphenyl(histidinate-O,N)borane
diphenyl(hydroxyprolinate-O,N)borane
diphenyl(glutaminate-O,N)borane
diphenyl(asparaginate-O,N)borane
diphenyl(lysinate-O,N)borane
diphenyl(2,3-diaminopropionate-O,N)borane
bis(4,4'-(phenyl-glutamineboryl)phenyl)ether
bis(4,4'-(phenylasparagineboryl)phenyl)ether
(4-(phenyl-glutamic acid boryl)phenyl)-(4'-(hydroxymethylphenyl-glutamic acid boryl)phenyl)ether
diphenyl(glutaminate-O,N)borane
diphenyl(prolinate-O,N)borane
(3-phenoxybenzyl)-(3'-(phenyl-2-aminoethoxyboryl)benzyl)ether
diphenyl(2-piperazinecarboxy)borane
diphenyl(2,4-diaminolacetic acid)borane
di(3-chloro-4-methylphenyl)-(picolinate-O,N)borane
di(3-chloro-4-methylphenyl)(asparaginate-O,N)borane
di(3-chloro-4-methylphenyl) 2-aminophenylthioborane
di(4-trifluoromethylphenyl)(picolinate-O,N)borane
di(4-trifluoromethylphenyl) 2-aminoethylthioborane
di(3-chloro-4-methylphenyl)(2,6-diaminopimelinate-O,N)borane
di(3-chloro-4-methylphenyl)(citrullinate-O,N)borane
di(3-chloro-4-methylphenyl)(glycylglutaminate-O,N)borane
di(4-trifluoromethylphenyl)(1,3-propylenediaminediacetate-O,N)borane
di(4-trifluoromethylphenyl)(glycylglycinate-O,N)borane
di(3-chloro-4-methylphenyl)(allothreoninate-O,N)borane
di(3-chloro-4-methylphenyl)(norloysinate-O,N)borane
di(3-chloro-4-methylphenyl)(2,4-diaminobutyrate-O,N)boranediphenyl dimethylaminoethylthioborane
di(3-chloro-4-methylphenyl)dimethylaminoethylthioborane
(4-(2-thiophenehydroxyboryl)phenoxyethyl)(4'-(2-thiophenehydroxyboryl)benzyl)ether
1,2-di(phenylhydroxyboryl)benzene
1,2-di(phenylaminoethoxyboryl)benzene
poly(2,5-dimethylphenyl asparagine-O,N borane)
poly(phenylene 2-aminoethylaminoethoxy borane)
poly(phenylene 2-pyridylmethoxy borane)
poly(1,4-phenylenehydroxyboryl-1,3-phenyleneborinic acid)
poly(1,4-phenylene aminoethoxyboryl-1,3-phenyleneaminoethoxyborane)
2,8-di(3-thiophenylglutamine-O,N boryl)dibenzothiophene
4,4'-(dicyano-phenyl)borinic acid
3,3'-(dicyano-phenyl)borinic acid
diphenyl(citrullinate-O,N)borane
diphenyl(ornithinate-O,N)borane
poly(1,2-phenylene-hydroxyborane)
poly(2,5-dimethyl-1,4-phenylene-hydroxyborane)
poly(2-methyl-1,3-phenylene-hydroxyborane)
poly(2,8-dibenzothiophenylene-hydroxyborane)
poly(2,2'-biphenylene-hydroxyborane)
poly(1,4-naphthalene-hydroxyborane)
poly(9,10-anthracene-hydroxyborane)
poly(3,6-carbazole-hydroxyborane)
poly(5-methyl-1,3-phenylene-hydroxyborane)
poly(5,5'-bithiophene-hydroxyborane)
poly(2,2'-binaphthyl-hydroxyborane)
poly(4,4'-biphenylene aminoethoxyborane)
poly(4,4'-biphenylene N-hydroxyethylaminoethoxyborane)
bis(4,4'-(3-chloro-4-methylphenylhydroxyboryl)benzyl)ether
poly(4-phenylborinic acid)
naphthaleneboronic acid
bis(4-(4-trifluoromethylphenylhydroxyboryl)benzyl)ether
poly(2,5-dimethylphenyl aminopropoxyborane)
poly(2,5-dimethylphenyl aminopropylthioborane)
bis(3-(4-methoxyphenylhydroxyboryl)benzyl)ether
(3-(phenylhydroxyboryl)benzyl) (4-(phenylhydroxyboryl)benzyl)ether
(2-(phenylhydroxyboryl)benzyl) (3-(phenylhydroxyboryl)benzyl)ether
(2-(phenylhydroxyboryl)benzyl) (4-(phenylhydroxyboryl)benzyl)ether
(3-(phenylaminoethoxyboryl)benzyl) (4-(phenylaminoethoxyboryl)benzyl)ether
bis(3-(3-chloro-4-methylphenylhydroxyboryl)benzyl)ether
(2-(phenylaminoethoxyboryl)benzyl) (3-(phenylaminoethoxyboryl)benzyl)ether
(2-(phenylaminoethoxyboryl)benzyl) (4-(phenylaminoethoxyboryl)benzyl)ether
bis(3-(4-fluorophenylhydroxyboryl)benzyl)ether
bis(3-(4-fluorophenylaminoethoxyboryl)benzyl)ether
bis(4-(4-chloro-3-methyl-phenyl)hydroxyborylbenzyl)ether
bis(4-(4-chloro-3-methyl-phenylaminoethoxyborylbenzyl)ether
bis(3-(3',4'-methylenedioxy-phenylhydroxyboryl)benzyl)ether
(3-(3-chloro-4-methylphenylhydroxyboryl)benzyl) (4-(3-chloro-4-methylphenylhydroxyboryl)benzyl)ether
(3-(3',4',5'-trifluorophenylhydroxyboryl)benzyl)(4-(3',4',5'-trifluorophenylhydroxyboryl)benzyl)ether
bis(3-(4-methoxyphenylaminoethoxyboryl)benzyl)ether
(3-(4-chloro-3-methylphenylhydroxyboryl)benzyl)(2-(4-chloro-3-methylphenylhydroxyboryl)benzyl)ether
bis(3-(4-cyanophenylhydroxyboryl)benzyl)ether
bis(3-(2'-thiophenylhydroxyboryl)benzyl)ether
bis(3-(1'-naphthylhydroxyboryl)benzyl)ether
bis(4-(2-methoxy-5-fluorophenylhydroxyboryl)benzyl)ether
bis(4-(2-methoxy-5-fluorophenylaminoethoxyboryl)benzyl)ether
(3-(4-chloro-3-methyl-phenylaminoethoxyboryl)benzyl)(2-(4-chloro-3-methyl-phenylaminoethoxyboryl)benzyl)ether
bis(4-(3,4-difluorophenylhydroxyboryl)benzyl)ether
bis(4-(3,4-difluorophenylaminoethoxyboryl)benzyl)ether
(3-(3',4',5'-trifluorophenylaminoethoxyboryl)benzyl)(4-(3',4',5'-trifluorophenylaminoethoxyboryl)benzyl)ether
5,5'-(phenylhydroxyboryl)-2,2'-dithiophene
5,5'-(phenylaminoethoxyboryl)-2,2'-dithiophene
3,5-di(phenylaminoethoxyboryl)toluene
2,5-di(phenylhydroxyboryl)toluene
2,2'di(phenylhydroxyboryl)-1,1'-binaphthyl
2,2'-di(phenylaminoethoxyboryl)-1,1'-binaphthyl
bis(4-(4-methylphenylhydroxyboryl)benzyl)ether bis(4-(4-methylphenylaminoethoxyboryl)benzyl)ether
4,4'-(4-methylphenylhydroxyboryl)diphenyl
4,4'-(4-methylphenylaminoethoxyboryl)diphenyl
4,4'-(4-methylphenylhydroxyboryl)diphenylether
poly(2,5-dimethylphenyl 2-pyridylmethoxyborane)
4,4'-bis(3-chloro-4-methyl-phenylhydroxyboryl)diphenylether
(2-(phenylhydroxyboryl)phenethyl)((2-phenylhydroxyboryl)benzyl)ether
(2-(phenylaminoethoxyboryl)phenethyl)((2-phenylaminoethoxyboryl)benzyl)ether
(4-phenylhydroxyborylphenyl)(4'-phenylhydroxyborylbenzyl)ether
(4-phenylaminoethoxyborylphenyl)(4'-phenylaminoethoxyborylbenzyl)ether
(4-trifluoromethylphenylhydroxyborylphenyl)(4'-trifluoromethylphenylhydroxyborylbenzyl)ether
(4-trifluoromethylphenylaminoethoxyborylphenyl)(4'-trifluoromethylphenylaminoethoxyborylbenzyl)ether
9,10-bis-(trifluoromethylphenylhydroxyboryl)anthracene
9,10-bis-(trifluoromethylphenylaminoethoxyboryl)anthracene
bis(3-(1-naphthylaminoethoxyboryl)benzyl)ether
4,5-di(phenylhydroxyboryl)-2,7-di-tert-butyl-9,9-dimethylxanthrene
4,5-di(phenylaminoethoxyboryl)-2,7-di-tert-butyl-9,9-dimethylxanthrene
(4-(phenylhydroxyboryl)phenoxyethyl)(4-(phenylhydroxyboryl)benzyl)ether
(4-(phenylaminoethoxyboryl)phenoxyethyl)(4-(phenylaminoethoxyboryl)benzyl)ether
6,6'-(phenylhydroxyboryl)-2,2'-dipyridyl
6,6'-(phenylaminoethoxyboryl)-2,2'-dipyridyl
bis(2,5-(phenylhydroxyboryl))furan
bis(2,5-(phenylaminoethoxyboryl))furan
bis(4,4'-(phenyl-N,N-dimethylaminoethoxyboryl)phenyl)ether
bis(4,4'-(phenyl-N-methylaminoethoxyboryl)phenyl)ether
2,8-di(phenylhydroxyboryl)dibenzothiophene
bis(4,4'-(phenyl-glutamineboryl)phenyl)ether
2,8-di(3-thiophenyl-2-pyrrolidinomethoxyboryl)dibenzothiophene
bis(4,4'-(phenyl-asparagineboryl)phenyl)ether
(4-(phenyl-N-methylaminoethoxyboryl)phenyl)(4'-(hydroxymethylphenyl-N-methylaminoethoxyboryl)phenyl)ether
(4-(phenyl-N,N-dimethylaminoethoxyboryl)phenyl)(4'-(hydroxymethylphenyl-N,N-dimethylaminoethoxyboryl)phenyl)ether
(4-(phenyl-glutamic acid boryl)phenyl)(4'-(hydroxymethylphenyl-glutamic acid boryl)phenyl)ether
(4-(phenyl-glutamineboryl)phenyl)(4'-(hydroxymethylphenyl-glutamineboryl)phenyl)ether
bis(4,4'-(phenyl-N,N-dimethylaminoethoxyboryl)phenyl)ether
bis(4,4'-(phenyl-N-aminoethyl-aminoethoxyboryl)phenyl)ether
(4-(phenyl-cysteineboryl)phenyl)(4'-(hydroxymethylphenyl-cysteineboryl)phenyl)ether
bis(4,4'-(phenoxyphenyl-aminoethoxyboryl)phenyl)ether
bis(4,4'-(phenyl-N-aminoethyl-aminoethoxyboryl)benzyl)ether
bis(4,4'-(phenyl-N-methylaminoethoxyboryl)benzyl)ether
(4'-trifluoromethylphenyl-N,N-dimethylaminoethoxyboryl)-4-phenyl(4'-trifluoromethylphenyl-N,N-dimethylaminoethoxyborylbenzyl)ether
(4'-trifluoromethylphenyl-N-methylaminoethoxyboryl)-4-phenyl (4'-trifluoromethylphenyl-N-methylaminoethoxyboryl-4-benzyl)ether
bis(3,3'-(phenyl-N,N-dimethylaminoethoxyboryl)benzyl) ether
bis(3,3'-(phenyl-asparagineboryl)benzyl)ether
bis(3,3'-(phenyl-aminoethylthioboryl)benzyl)ether
2,8-di(3-thiophenylhydroxyboryl)dibenzothiophene
bis(4,4'-(p-trifluoromethylphenyl-hydroxyboryl)benzyl) ether
2,8-di(phenylaminoethoxyboryl)dibenzothiophene
bis(4,4'-(phenyl-lysineboryl)benzyl)ether
bis(4,4'-(p-methoxy-phenyl-hydroxyboryl)benzyl)ether
bis(4,4'-(3,4-difluorophenyl-hydroxyboryl)benzyl)ether
bis(4,4'-(p-methoxyphenyl-aminoethoxyboryl)benzyl)ether
bis(4,4'-(p-methoxyphenyl-N-methylaminoethoxyboryl)benzyl)ether
bis(4,4'-(p-methoxyphenyl-N,N-dimethylaminoethoxyboryl)benzyl)ether
bis(4,4'-(p-methoxyphenyl-2,4-diaminobutyric acid boryl)benzyl)ether
bis(4,4'-(3,4-difluorophenyl-aminoethoxyboryl)benzyl) ether
bis(4,4'-(3,4-difluorophenyl-N-methylaminoethoxyboryl)benzyl)ether
bis(4,4'-(3,4-difluorophenyl-N,N-dimethylaminoethoxyboryl)benzyl)ether
bis(4,4'-(3,4-difluorophenyl-N-aminoethylaminoethoxyboryl)benzyl)ether
bis(4,4'-(3-chloro-4-methylphenyl-aminoethoxyboryl)benzyl)ether
bis(4,4'-(3-chloro-4-methylphenyl-N-methylaminoethoxyboryl)benzyl)ether
bis(4,4'-(3-chloro-4-methylphenyl-N,N-dimethylaminoethoxyboryl)benzyl)ether
bis(4,4'-(3-chloro-4-methylphenyl-2-piperidylmethoxyboryl)benzyl)ether
bis(4,4'-(p-trifluoromethylphenyl-N,N-dimethylaminoethoxyboryl)benzyl)ether
bis(4,4'-(p-trifluoromethylphenyl-asparagineboryl)benzyl) ether
bis(4,4'-(p-trifluoromethylphenyl-aminoethoxyboryl)benzyl)ether
(4-phenyl-N-methylaminoethoxyborylphenyl)(4'-phenyl-N-methylaminoethoxyborylbenzyl)ether
(4-phenyl-N,N-dimethylaminoethoxyborylphenyl) (4'-phenyl-N,N-dimethylaminoethoxyborylbenzyl)ether
(4-phenyl-2-pyridylmethoxyborylphenyl)(4'-phenyl-2-pyridylmethoxyborylbenzyl)ether
4-(phenyl-p-methoxyphenyl-2-pyridylmethoxyboryl)-phenyl 4'-(phenyl-p-methoxyphenyl-2-pyridylmethoxyboryl)benzylether
bis(4,4'-(phenyl-3-piperidyloxyboryl)phenyl)ether
bis(4,4'-(phenyl-2-pyridylmethoxyboryl)phenyl)ether
bis(4,4'-(phenyl-aminoethylthioboryl)phenyl)ether
bis(4,4'-(phenyl-2-amino-1-phenylethoxyboryl)phenyl) ether
bis(4,4'-(phenyl-ornithineboryl)phenyl)ether
bis(4,4'-(phenyl-2,3-diaminopropionic acid boryl)phenyl) ether
bis(4,4'-(phenyl-lysineboryl)phenyl)ether
bis(4,4'-(phenyl-2-pyrrolidinemethoxyboryl)phenyl)ether
bis(4,4'-(naphthylhydroxyboryl)phenyl)ether
bis(4,4'-(tolylhydroxyboryl)phenyl)ether
bis(4,4'-(naphthyl-aminoethoxyboryl)phenyl)ether
bis(4,4'-(naphthyldimethylaminoethoxyboryl)phenyl)ether
bis(4,4'-(naphthyl-2-pyridylmethoxyboryl)phenyl)ether bis(4,4'-(naphthylglutamineboryl)phenyl)ether
bis(4,4'-(naphthyl 2,4-diaminopropionic acid boryl)phenyl)ether
bis(4,4'-(tolyldimethylaminoethoxyboryl)phenyl)ether
bis(4,4'-(tolylpiperadylethoxyboryl)phenyl)ether
bis(4,4'-(tolylasparagineboryl)benzyl)ether
bis(4,4'-(tolyllysineboryl)phenyl)ether
bis(4,4'-(phenyl-aminoethylthioboryl)benzyl)ether
bis(4,4'-(phenyl-2-pyrrolidinemethoxyboryl)benzyl)ether
bis(4,4'-(phenyl-2,4-diaminobutyric acid boryl)benzyl)ether
bis(4,4'-(phenyl-butylaminoethoxyboryl)benzyl)ether
bis(4,4'-(phenyl-phenylaminoethoxyboryl)benzyl)ether
bis(4,4'-(phenyl-benzylaminoethoxyboryl)benzyl)ether
bis(4,4'-(phenyl-N-methylpiperidine-methoxyboryl)benzyl)ether
bis(4,4'-(phenyl-1-methyl-2-aminoethoxyboryl)benzyl)ether
bis(4,4'-(phenyl-1-piperidylethoxyboryl)benzyl)ether
bis(3,3'-(phenyl-2-pyrrolidinomethoxyboryl)benzyl)ether
bis(3,3'-(phenyl-2-phenyl-2-aminoethoxyboryl)benzyl)ether
bis(3,3'-(phenyl-2-piperidylmethoxyboryl)benzyl)ether
bis(3,3'-(phenyl-dimethylaminoethoxyboryl)benzyl)ether
bis(3,3'-(phenyl-1-methyl-2-aminoethoxyboryl)benzyl)ether
bis(3,3'-(phenyl-1-piperidylethoxyboryl)benzyl)ether
bis(3,3'-(phenyl-2-pyridylmethoxyboryl)benzyl)ether
bis(3,3'-(phenyl-2-amino-1-phenylethoxyboryl)benzyl)ether
bis(3,3'-(phenyl-N-methylaminoethoxyboryl)benzyl)ether
bis(3,3'-(phenyl-N-aminoethyl-1-methyl-2-aminoethoxyboryl)benzyl)ether
bis(3,3'-(phenyl-glutamineboryl)benzyl)ether
bis(3,3'-(phenyl-2,4-diaminobutyric acid boryl)benzyl)ether
bis(3,3'-(phenyl-N-butylaminoethoxyboryl)benzyl)ether
bis(3,3'-(phenyl-asparagineboryl)benzyl)ether
bis(3,3'-(phenyl-lysineboryl)benzyl)ether
bis(3,3'-(phenyl-ornithineboryl)benzyl)ether
bis(4,4'-(phenyl-2-methyl-8-quinolinooxyboryl)phenyl)ether
bis(4,4'-(phenyl-2-benzyl-2-amino-ethoxyboryl)benzyl)ether
bis(4,4'-(phenyl-2-benzyl-2-amino-ethoxyboryl)phenyl)ether
bis(3,3'-(phenyl-2-benzyl-2-amino-ethoxyboryl)benzyl)ether
2,8-di(phenylglutamine-O,N borane)dibenzothiophene
2,8-di(phenyl 2-pyrrolidinomethoxyboryl)dibenzothiophene
2,8-di(phenylarginine-O,N borane)dibenzothiophene
2,8-di(3-thiophenylaminoethoxyboryl)dibenzothiophene
bis(2,2'-(phenylhydroxyboryl)benzyl)ether
2-aminoethyl diphenylborinate
diphenylborinic acid
poly(4,4'-biphenylene aminoethylthioborane)
poly(4-phenylborinic acid)
poly(dimethylaminoethoxyphenyleneborane)
1,3,5-tri(phenyl 2-aminoethoxyboryl)benzene
dibutyl(phenylalanine-O,N)borane
4,4'-di(phenyl 1-(pyridin-2-yl)-1-trifluoromethylphenyl-methoxyboryl)benzylether
di(3-chloro-6-methylphenyl)aminoethylborinate
bis(4,4'-(p-trifluoromethylphenyl-asparagineboryl)benzyl)ether
di(3-chloro-4-methyl)phenyl(methionate-O,N)borane
poly(1,4-phenylene 2-pyridylmethoxyborane)
poly(diphenyletherhydroxyborane)
4,4'-di(phenyl 1-(pyridin-2-yl)-1-trifluoromethylphenyl-methoxyborylbenzyl)ether The present invention also relates to the compounds represented by the following formula (4') or (8') or a pharmaceutically acceptable salt thereof.

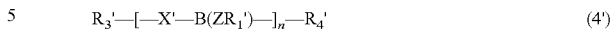

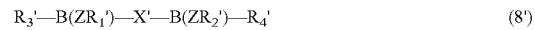

In the formulas, B is a boron atom, Z is O or S, $R_1'$ and $R_2'$ are H, —$(CH_2)_m$—$NR_5'R_6'$, —$CHR_{11}'R_{12}'$, —COCH$(NH_2)$—$(CH_2)_m$NHCONH$_2$ or —COCH$(NH_2)$—$(CH_2)_m$—$COR_{19}'$. Here, $R_5'$, $R_6'$, $R_{11}'$, $R_{12}'$ and $R_{19}'$ are independently H, or amino or heterocyclyl, each of which is substituted or unsubstituted. $R_3'$ and $R_4'$ are H, aryl or heterocyclyl, X' is substituted or unsubstituted aromatic group, m is an integer of 1-5, and n is an integer of 1-100.

The "amino", "heterocyclyl", "aryl" and "aromatic group" are as defined above.

Specifically, the following compound can be mentioned:

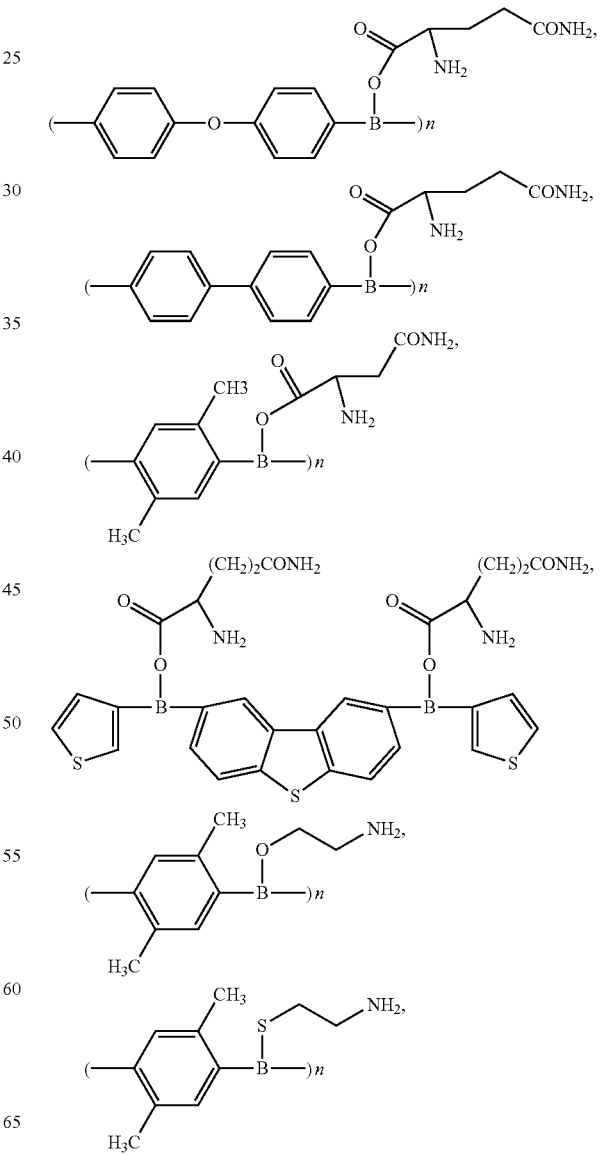

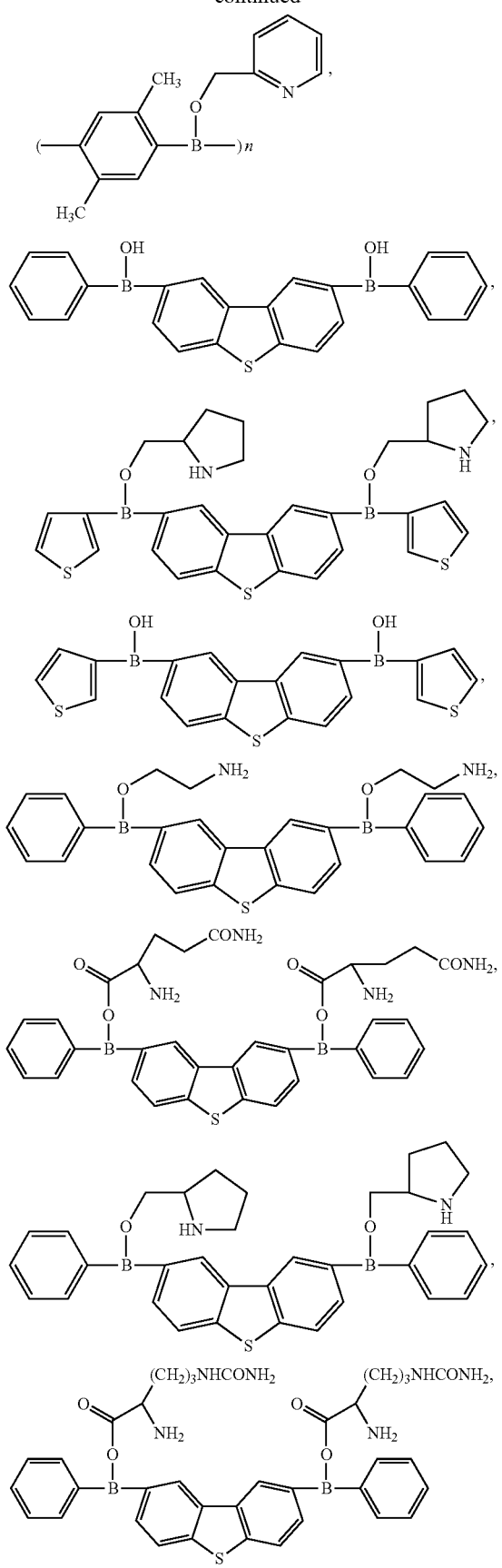

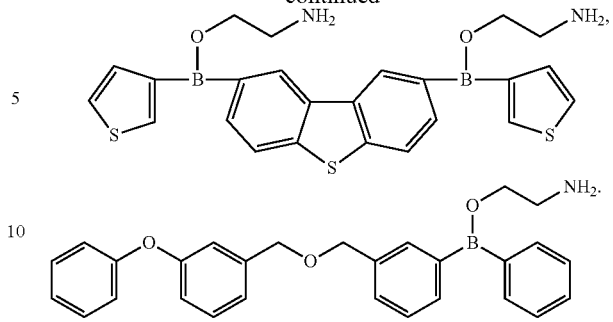

The compounds (1)-(13) in the present invention can be converted to pharmaceutically acceptable non-toxic salts by a known method. The non-toxic salts include, for example, alkali metal salts, alkaline earth metal salts, amine salts, acid addition salts, solvates (including hydrates) and the like. In general, water-soluble ones are preferable.

Suitable non-toxic salts are salts with alkali metal such as potassium, sodium and the like; salts with alkaline earth metal such as calcium, magnesium and the like; and salts with organic amine such as triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like, preferably, alkali metal salts.

Moreover, as suitable acid addition salts, inorganic acid salts such as hydrochloride, hydrobromide, sulfate, phosphate, nitrate, and organic acid salts such as acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate and gluconate can be mentioned.

The compound of the present invention also includes solvates. Solvate is a conjugate, particularly in a crystal form, of the aforementioned compound of the present invention and a pharmaceutically acceptable solvent (for example, water, organic solvent) at a stoichiometrical or non-stoichiometrical ratio.

The present invention relates to a prophylactic and/or therapeutic drug for a disease caused by protein cross-linking, which contains the aforementioned protein cross-linking inhibitor.

As the disease caused by abnormal protein cross-linking, for example, Alzheimer's disease, Huntington's disease, Parkinson's disease, Celiac disease, cataract, mad cow disease, congenital lamellar ichthyosis and congenital hemostatic disorder can be mentioned. Particularly, it is desirably used as prophylactic and/or therapeutic drug for Alzheimer's disease.

The compound of the present invention can be synthesized by the methods described in WO03/033002 and WO2007/061074 or a method analogous thereto. In addition, the compound of the present invention can be synthesized by the following method or a method analogous thereto.

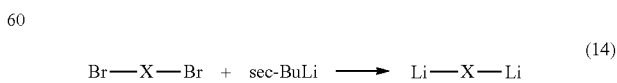

(14)

(15)

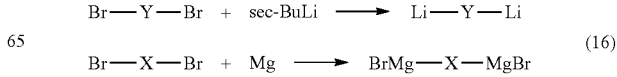

(16)

-continued

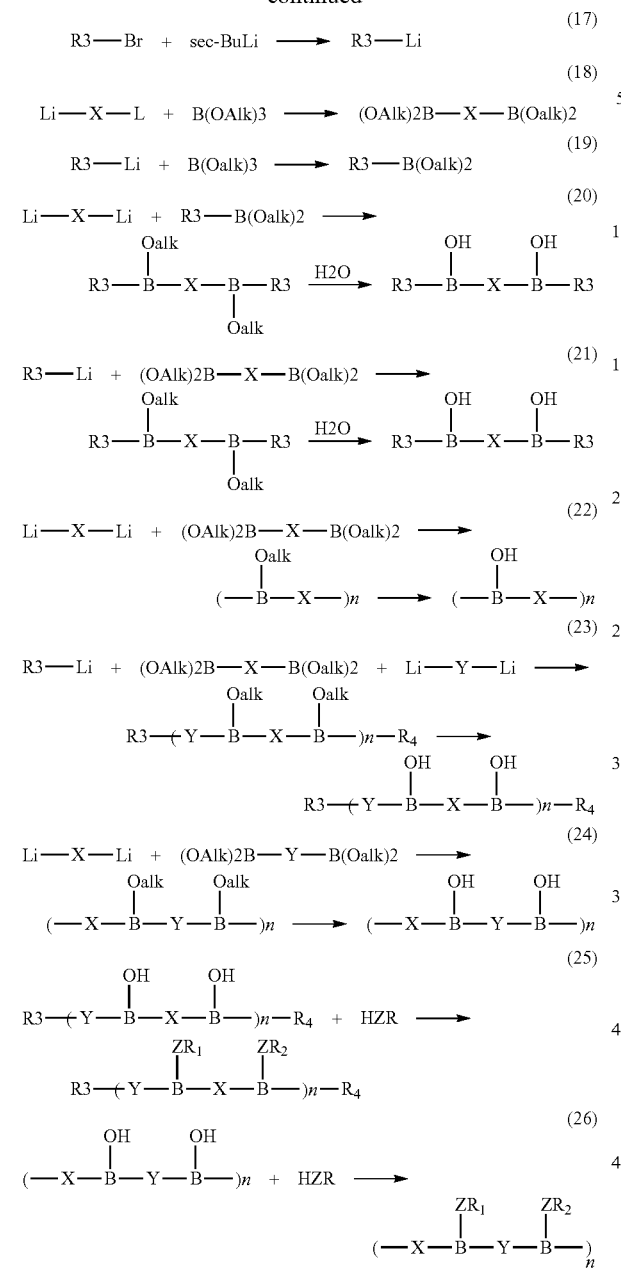

The main starting materials for the production of the compound of the present invention are monobromo compound, dibromo compound and alkoxyborane. A bromo compound is reacted with alkyl lithium to give a lithium compound R$_3$—Li (formula (17)). A dibromo compound (Br—X—Br or Br—Y—Br) is reacted with alkyl lithium to give a dilithium compound (Li—X—Li or Li—Y—Li) (formula (14) and formula (15)). Alternatively, magnesium is reacted to give a Grignard reagent (formula (16)). These metal compounds are reacted with trialkoxyborane to give dialkoxyborane R$_3$—B(OAlk)$_2$ (formula (19)). R$_3$—B(OAlk)$_2$ is reacted with Li—X—Li to give R$_3$—B(OAlk)-X—B—(OAlk)-R$_3$ (formula (20)) (Alk is an alkyl group having 1 to 4 carbon atoms). A dilithium compound (Li—X—Li) is reacted with R$_3$—B(OAlk)-X—B—(OAlk)-R$_3$ to give (—B(OAlk)-X—)$_n$. The resultant product is treated with acidic water to give (—B(OH)—X—), (formula (22)). R$_3$—Li, R$_4$—Li, (OAlk)$_2$B— X—B(OAlk)$_2$ and Li—Y—Li are reacted to give R$_3$—(—Y—B(OAlk)-X—B(OAlk)-)$_n$—R$_4$ and this is treated with acidic water to give R$_3$—(—Y—B(OH)—X—B(OH)—)$_n$—R$_4$ (formula (23)). Li—X—Li is reacted with (OAlk)$_2$B—Y—B(OAlk)$_2$ to give (—X—B(OAlk)-Y—B(OAlk)-)$_n$, which is treated with acidic water to give (—X—B(OH)—Y—B(OH)—)$_n$ (formula (24)). These two bifunctional compounds are reacted to give various borinic acids. Borinic acid is reacted with desired HZR wherein R is R$_1$ or R$_2$ used in the formulas (1)-(13)) to give the object compound (formulas (25) and (26)).

By a reaction with diphenylborinic acid using amino acid and β aminothiol instead of β amino alcohol, a dehydrating reaction occurs and a desired compound can be obtained (formula (27), formula (28)).

$$C_6H_5B(OH)C_6H_5 + HOOC_6CHRNH_2 \rightarrow C_6H_5B(OCO\text{-}CHRNH_2)C_6H_5 \quad (27)$$

$$C_6H_5B(OH)C_6H_5 + HSCH_2CH_2NH_2 \rightarrow C_6H_5B(SCH_2CH_2NH_2)C_6H_5 \quad (28)$$

As for a part of the compounds (1)-(13) of the present invention, according to the aforementioned schemes (14)-(26), borinic acid is synthesized from a bromine compound and bromobenzene by a similar method, which is reacted with amino alcohol, amino acid or aminothiol to synthesize a desired compound.

In addition, a compound represented by the formula (4') or (8') can be synthesized according to the formulas (20), (29), (30) and (31).

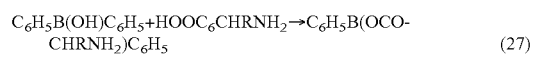

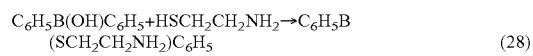

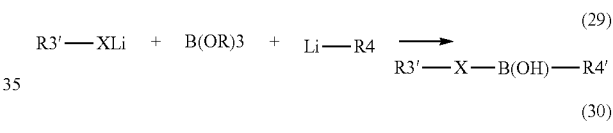

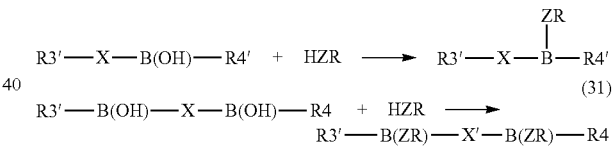

In the following, the compounds represented by the formulas (1)-(13) (including compounds represented by the formulas (4') and (8')) are also referred to as the compound of the present invention.

In the present invention, the enzyme (transglutaminase (TGase)) inhibitory action is determined by measuring the enzyme activity by an appropriately-modified method based on Lorand et al. (Lorand, L. et al. (1971), Anal Biochem. 1971 November; 44(1):221-31.). For example, the method described in the Example can be performed.

In the present invention, the polyglutamine aggregation inhibitory activity (x-Fold) can be measured, for example, by the method described in the Example.

The SOC (store operated calcium channel)-suppressive action can be measured by the method described in the Example and using, for example, FDSS 3000.

The compound of the present invention (i.e., active substance or active ingredient) is administered systemically or topically in an oral or parenteral dosage form to a test subject (mammal inclusive of human, preferably human). The parenteral administration includes intravenous administration, intraarterial administration, intramuscular administration, subcutaneous administration, intradermal administration, intraperitoneal administration, intrarectal administration, intradural administration, vaginal administration, transmucosal administration and the like.

While the dose varies depending on the kind of the compound to be administered, age, body weight and symptom of the subject of administration, treatment effect, administration method and the like, generally, for example, 10 μg-1000 mg is orally administered to one adult (body weight about 60 kg) once to several times per day or, for example, 1 μg-100 mg is parenterally administered to one adult (body weight about 60 kg) once to several times per day.

The administration preparation of the compound of the present invention includes, but are not limited to, tablet, pill, suspension, solution, capsule, syrup, elixir, granule, powder and the like for oral administration, injection, external preparation, suppository, external liquid, ointment, embrocation, inhalant, spray, pessary for vaginal administration and the like for parenteral administration.

The aforementioned preparation can contain a pharmacologically acceptable carrier (excipient, diluent and the like) or an additive in combination with the compound of the present invention as an active ingredient.

As the aforementioned excipient and additive, those conventionally used in the field of medicaments can be used. For example, the agents and formulation methods described in Remington: The Science and Practice of Pharmacy $9^{th}$ ed. (1995) MACK PUBLISHING COMPANY (US) can be referred to.

Examples of the excipient include lactose, mannitol, glucose, microcrystalline cellulose, starch and the like.

Examples of the additive include binders (hydroxypropylcellulose, polyvinylpyrrolidone, magnesium alumino metasilicate etc.), disintegrants (calcium cellulose glycolate etc.), lubricants (magnesium stearate etc.), stabilizers, solubilizing agents (glutamic acid, aspartic acid etc.) and the like.

The preparation of the present invention may be coated with a coating agent (sucrose, gelatin, hydroxypropylcellulose, hydroxypropylmethylcellulosephthalate etc.), or may be coated with two or more layers. By applying such coating, the forms of control release preparation, enteric preparation and the like can be provided. Further, a capsule of absorbable substances such as gelatin is also encompassed.

In a liquid for oral administration, one or more of the activity substances are dissolved, suspended or emulsified in a generally-used diluent (purified water, ethanol, buffer, or a mixed solution thereof etc.). Further, the liquid may contain a wetting agent, a suspending agent, an emulsifier, a stabilizer, a sweetening agent, a flavoring agent, an aromatic, a preservative, a buffering agent and the like.

The injection for parenteral administration includes a solution, a suspension, an emulsion and an injection obtained by dissolving or suspending in a solvent when in use. An injection can be obtained by dissolving, suspending or emulsifying one or more active substances in a solvent. As the solvent, for example, distilled water for injection, saline, vegetable oil, alcohols such as propylene glycol, polyethylene glycol and ethanol and a combination thereof are used. Furthermore, the injection may contain a stabilizer (amino acid such as lysine, methionine and the like, sugar such as trehalose and the like), a solubilizing agent (glutamic acid, aspartic acid, polysorbate 80 (registered trademark) etc.), a suspending agent, an emulsifier, a soothing agent, a buffering agent, a preservative and the like. These injections are sterilized in the final step or produced and prepared by an aseptic operation method. In addition, an aseptic solid agent, for example, a freeze-dried product may be produced, and dissolved in sterilized or aseptic distilled water for injection or other solvent and used.

A spray may contain, besides a generally-used diluent, a stabilizer such as sodium bisulfite and a buffering agent that achieves isotonicity, for example, an isotonic agent such as sodium chloride, sodium citrate and citric acid.

In the present specification, when the terminal group is a hydroxyl group, a chemical formula omitting a hydroxyl group is sometimes described. The number after the compound name is the compound No.

EXAMPLE

Experimental Example 1

Measurement of TG

The compound of the present invention (10 mM, 1 μL) was taken in a 96-well plate (Nunc, 96 Well Black Plate with Clear Bottom), an enzyme reaction solution (100 mM HEPES-NaOH, pH 7.5, 1 mM $CaCl_2$, 20 μM monodansyl cadaverine, 0.05 mg/mL N,N-dimethylcasein, 5 μg/mL TGase) (0.1 ml) was added and the mixture was sufficiently mixed without making foams. The mixture was set on a fluorescence drug screening system FDSS 3000 (Hamamatsu Photonics K.K.), and changes in the fluorescence wavelength per unit time at 340 nm were measured, based on which the TGase inhibitory activity of the compound of the present invention was calculated. As a control, change in the fluorescence when 1 μL of DMSO (dimethyl sulfoxide) was added instead of the compound of the present invention was taken as 100, and TG50 was when the activity decreased to half due to the compound of the present invention. The results are shown in the following.

Experimental Example 2

Measurement of x-Fold

Truncated N-terminal huntington 150 Q-EGFP-Neuron 2a cells (prepared according to Wang, G. H., Nukina, N et al, Neuroreport, 10, 2435-2438 (1999)) were cultured for one day in a 96-well plate, 1 μM ponasterone A (2 μL) and 5 μM dibutyl cyclic AMP (2 μL) were added such that the concentration of the compound of the present invention became 20 μM, and the mixture was cultured for 20 hr. The cells were fixed with 4% para-formaldehyde and, 30 min later, the cells were washed with PBS and stained with Hoechst 33342. The number of the aggregated cells, and the total number of cells were counted by Array Scan V T1 (manufactured by Cellomics, Pittuburg, USA), and the ratio of the aggregated cells to the total number of cells was determined (x-Fold). Without the compound of the present invention, the respective numbers of cells were almost the same, and the number of the aggregated cells to the total number of cells was almost 1. A smaller value shows a stronger polyglutamine aggregation inhibitory activity. The results are shown in the following.

Experimental Example 3

Measurement of SOC IC50

CHO cell culture medium was replaced with a BSS solution which is an extracellular fluidfree of calcium, the compound of the present invention was added 1 min later, and 1 μM thapsigargin was allowed to act thereon 2 min later to deplete intracellular calcium store. After 9 min, to the extracellular fluid was added calcium chloride at the final concentration of 2 mM, and an influence of each compound on the degree of increase in the intracellular calcium concentration after addition was estimated, based on which SOC suppressive action (IC50) was determined. The results are shown in the following.

Example 1

2-aminoethylthio bis(4-chloro-2-fluorophenyl)borane (6014)

TG 28, x-Fold 0.95

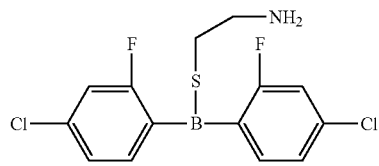 [SMILES: NCCSB(c1ccc(Cl)cc1F)c1ccc(Cl)cc1F]

Example 2

(4-(phenylglutamineboryl)phenyl)(4'-(phenylhydroxyboryl)phenyl)ether (7111)

TG 28, x-Fold 0.82, SOC IC50 0.2 µM

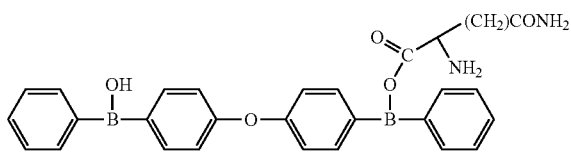

Example 3 bis(4,4'-(phenylhydroxyboryl)phenyl)ether (536)

TG −20, x-Fold 0.49, SOC IC50 0.5 µM

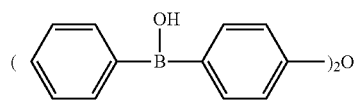

Example 4 poly(4,4'-biphenylene N-methylaminoethoxyborane) (1130)

TG 109, x-Fold 0.80, SOC IC50 5 µM

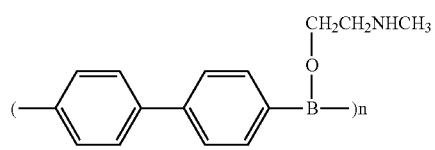

Example 5 bis(4,4'-(phenylaminoethoxyboryl)phenyl)ether (1022)

TG −4, x-Fold 0.60, SOC IC50 0.15 µM

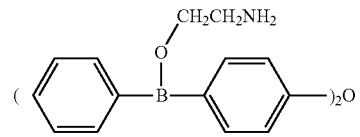

Example 6

(4-(phenylasparagineboryl)phenyl)(4'-(phenylhydroxyboryl)phenyl)ether (7132)

TG 23, x-Fold 1.01, SOC IC50 0.2 µM

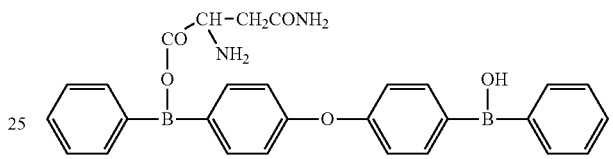

Example 7 bis(3,3'-(phenylhydroxyboryl)benzyl)ether (162OH)

TG 14, x-Fold 1.03, SOC IC50 0.2 µM

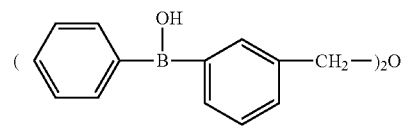

Example 8 bis(3,3'-(phenylaminoethoxyboryl)benzyl)ether (162AE)

TG 24, x-Fold 1.1, SOC IC50 0.2 µM

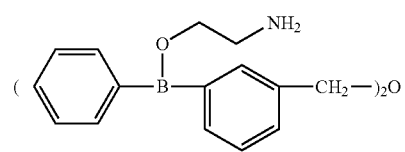

Example 9

4,4'(phenyl-2-aminoethylthioboryl)diphenyl (6077)

TG 12, x-Fold 0.87, SOC IC50 0.5 µM

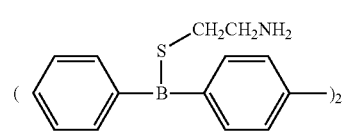

Example 10

4,4'(phenyl-2-aminoethoxyboryl)diphenyl (6076)

TG 7, x-Fold 0.92, SOC IC50 0.5 μM

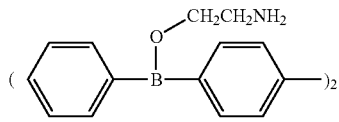

Example 11 poly(2,5-dimethoxy-4-phenylborinic acid) (6047)

TG 36, x-Fold 0.99

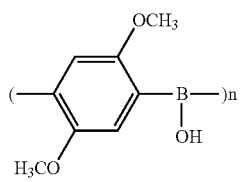

Example 12 poly(aminoethyl-2,5-dimethoxy-4-phenylborinate) (6050)

TG 91, x-Fold 1.04

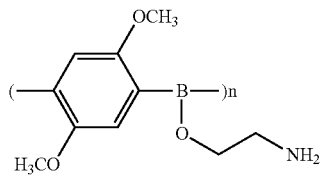

Example 13 poly(1,4-phenylenemethyleneoxymethylene 1,4-phenylene hydroxyborane) (1122)

TG 100, x-Fold 1.11

4,4'-p-brombenzyl ether (90 mg) was dissolved in ether (4 ml), and the mixture was cooled to −78° C. 1N sec-Butyllithium (0.75 mL) was added and the mixture was stirred for 60 min (SOLUTION A). 4,4'-parabromophenyl ether (90 mg) was dissolved in ether (4 ml), and the mixture was cooled to −78° C. Thereto was added 1N sec-butyllithium (0.7 mL) and the mixture was stirred for 30 min. Triisopropoxyborane (188 mg) was added and the mixture was stirred to −65° C. (SOLUTION B). SOLUTION A and SOLUTION B were mixed, and the mixture was gradually warmed and stirred at room temperature for 15 hr. The mixture was acidified with 1N hydrochloric acid, and the organic layer was washed with water, dried, and concentrated to give the title compound (154 mg).

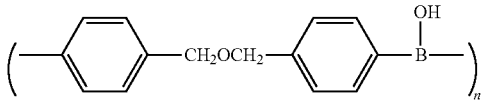

Example 14 poly(1,4-phenylenemethyleneoxymethylene 1,4-phenylene 2-aminoethoxyborane) (1132)

TG 85, x-Fold 1.03

Poly(1,4-phenylenemethyleneoxymethylene 1,4-phenylene hydroxyborane) (34 mg) obtained in Example 13 was dissolved in a mixture of ethanol (0.5 mL) and ether (0.5 mL) and the mixture was stirred at 50° C. for 1 hr. After concentration, ether (1 mL) was added to produce the title compound (15 mg) as a white precipitate.

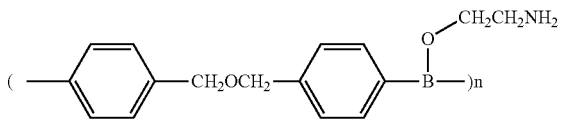

Example 15 poly(4,4'-phenylenemethyleneoxymethylene 4,4'-phenylene-dimethylaminoethoxyborinic acid) (1133)

TG 91, x-Fold 0.90

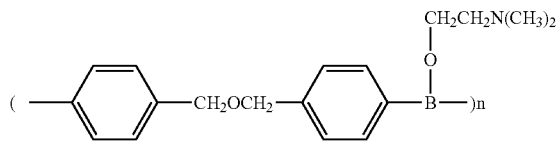

Example 16 poly(1,4-phenylenemethyleneoxymethylene 1,4-phenylene 2-piperidinomethoxyborane) (1134)

TG 86, x-Fold 0.95

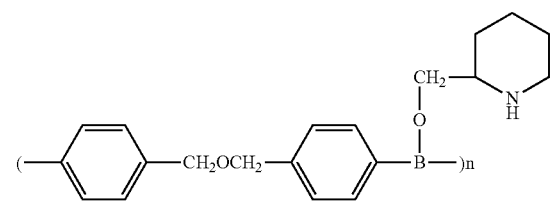

Example 17 poly(1,4-phenyleneoxy-1,4-phenylenehydroxyborane) (503)

TG 111, x-Fold 0.65

4,4'-Dibromodiphenylether (328 mg) was dissolved in ether (10 ml), sec-butyllithium (2 ml) was added at −95° C. and the mixture was warmed to −78° C. 30 min later. Thereto was added triisopropoxyborane (188 mg) and the mixture was stirred for 1 hr. The mixture was gradually warmed and stirred at room temperature for 15 hr. The mixture was acidified with 1N hydrochloric acid, and the organic layer was washed with water, dried, concentrated, and subjected to silica gel column chromatography to give the title compound (112 mg).

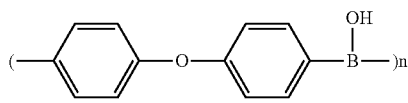

Example 18 poly(aminoethoxyboryldiphenylether) (1042D)

TG −17, x-Fold 0.84, SOC IC50 1.5 μM

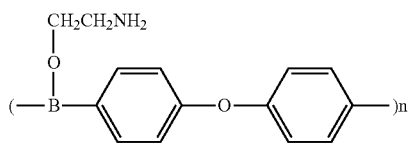

Example 19 poly(isopropoxyboryldiphenylether) (1042E)

TG 47, x-Fold 0.86

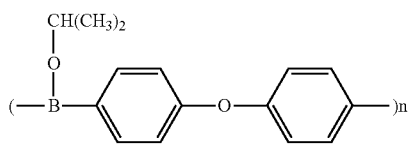

Example 20 poly(4,4'-diphenylether dimethylaminoethoxyborane) (1056)

TG 54, x-Fold 0.63, SOC IC50 4 μM

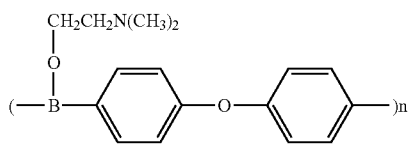

Example 21 poly(4,4'-diphenylether-2-pyridyl-4-trifluoromethylphenylmethoxyborane) (1120)

TG 111, x-Fold 0.72

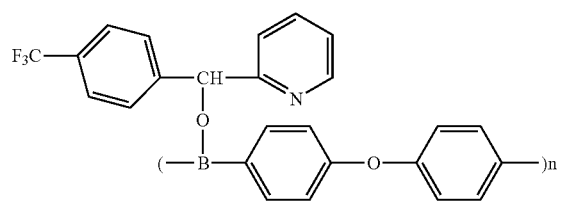

Example 22 poly(4,4'-diphenylether-2-aminoethylthioborane) (1121)

TG 30, x-Fold 0.62

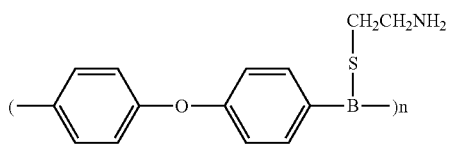

Example 23 poly(phenylenemethyleneoxyphenylenehydroxyborane) (1107)

TG 114, x-Fold 0.62

4,4'-p-bromophenyl p-brombenzyl ether (171 mg) was dissolved in ether (8 ml), and the mixture was cooled to −100° C. Thereto was added 1N sec-butyllithium (1 mL) and the mixture was stirred for 30 min to −78° C. (SOLUTION A). p-bromophenyl p-brombenzyl ether (171 mg) was dissolved in ether (10 ml), and the mixture was cooled to −78° C. Thereto was added 1N sec-butyllithium (1 ml) and the mixture was stirred for 30 min. Triisopropoxyborane (188 mg) was added and the mixture was stirred to −65° C. (SOLUTION B). SOLUTION A and SOLUTION B were mixed, and the mixture was gradually warmed and stirred at room temperature for 15 hr. The mixture was acidified with 1N hydrochloric acid, and the organic layer was washed with water, dried, and concentrated to give the title compound (161 mg).

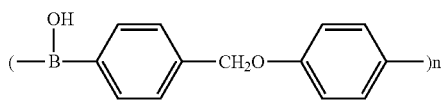

Example 24 poly(phenylenemethyleneoxyphenyleneaminoethoxyborane) (1116)

TG 96, x-Fold 0.78

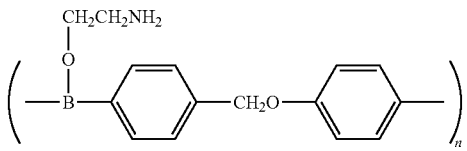

Example 25 poly(phenylenemethyleneoxyphenyleneaminoethylthioborane) (1117)

TG 12, x-Fold 0.69

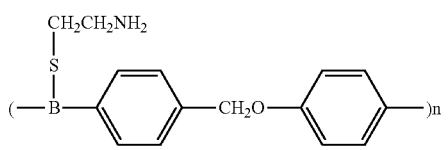

Example 26 poly(phenylenemethyleneoxyphe-
nylenedimethylaminoethoxyborane) (1109)

TG 116, x-Fold 0.78

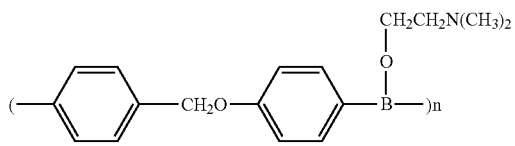

Example 27 poly(4'-phenylhydroxyboranephenylen-
emethyleneoxyphenylenehydroxyborane phenylen-
emethyleneoxymethylene) (1108-3)

TG 45, x-Fold 0.86, SOC IC50 5 μM
The title compound (189 mg) was obtained from bis(4-bromobenzyl)ether (178 mg) and parabromophenyl parabrombenzyl ether (171 mg).

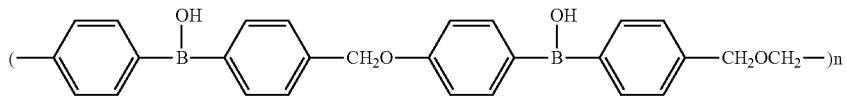

Example 28 poly(phenylenemethyleneoxyphenyle-
neaminoethoxyboranephenylene-methyleneoxymeth-
ylenephenylene aminoethoxyborane) (1114)

TG 94, x-Fold 0.72

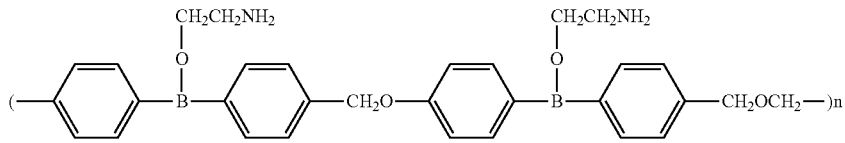

Example 29 poly(phenylenemethyleneoxyphenyle-
nemethylaminoethoxyborane-phenylenemethyl-
eneoxymethylenephenylenem-
ethylaminoethoxyborane) (1115)

TG 52, x-Fold 0.83

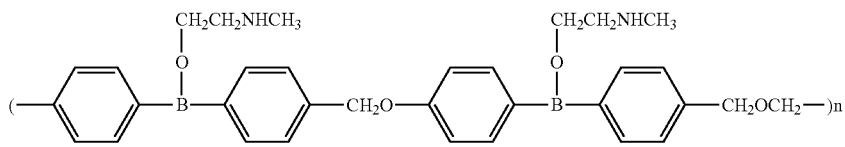

Example 30 poly(4,4'-biphenylene-hydroxyborane 1,4-phenylen-
emethyleneoxymethylenephenylenehydroxyborane)
(1141c)

TG 107, x-Fold 1.02

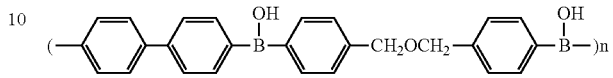

Example 31 poly(4,4'-biphenylene 2-aminoethoxyborane 1,4-
phenylene-methyleneoxymethylene 1,4-phenylene
2-aminoethoxyborane) (1146)

TG 127, x-Fold 0.95

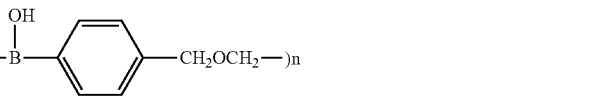

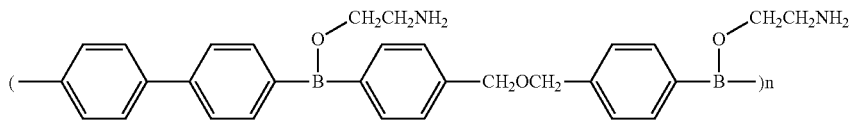

Example 32 di(3-chloro-4-methylphenyl)-2-aminoethylthioborane (3115)

TG 12, x-Fold 1.02, SOC IC50 1 μM di(3-Chloro-4-methylphenyl)borinic acid (44 mg) and 2-aminoethanethiol (35 mg) were reacted in ethanol (1 mL) to give the title compound (52 mg).

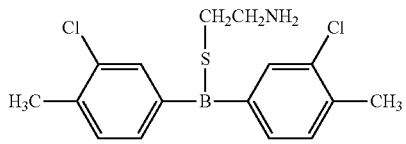

Example 33 poly(2,5-dimethoxy-4-phenylene-hydroxyborane-1,4-phenylenehydroxyborane) (6048)

TG 51, x-Fold 0.92

Paradibromobenzene (353.85 mg) was dissolved in ether (10 mL), and sec-butyllithium (3 mL) was added at −95° C. 30 min later, triisoproxyborane (552 μL) was added at −78° C. and the mixture was stirred for 1 hr (SOLUTION A). 2,5-Dimethoxy-1,4-dibromobenzene (443.35 mg) was dissolved in ether (10 μL), sec-butyllithium (3 ml) was added at −95° C. and the mixture was stirred for 30 min (SOLUTION B). SOLUTION A and SOLUTION B were mixed at −78° C., and the mixture was gradually warmed to room temperature and stirred overnight. Thereto was added hydrochloric acid solution to give the title compound (4.9 mg).

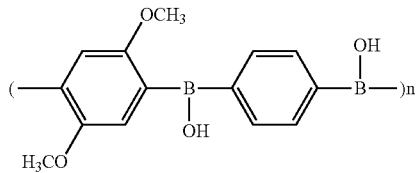

Example 34 poly(aminoethyl(2,5-dimethoxy-4-phenylene)aminoethoxyboryl(1,4-phenylene)borinate) (6051)

TG 39, x-Fold 1.01

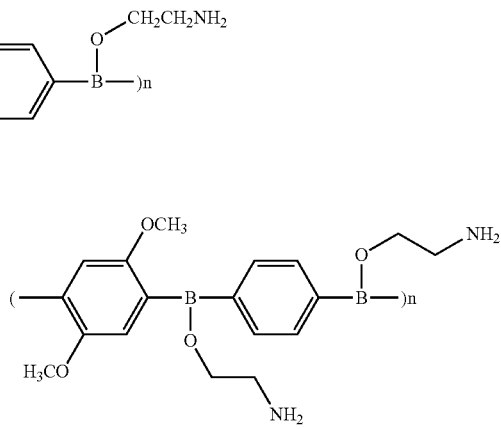

Example 35 poly(2-pyridylmethyl(2,5-dimethoxy-4-phenylene) 2-pyridylmethoxyborane-(1,4-phenylene)borinate) (6053)

TG 14, x-Fold 0.98

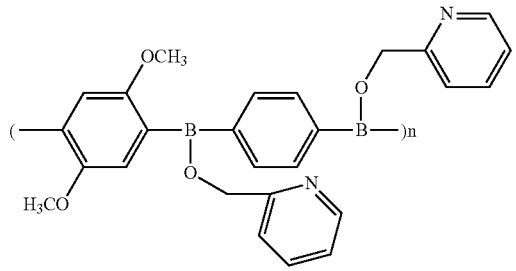

Example 36 poly(4,4'-biphenylene-hydroxyborane 4,4'-diphenylether hydroxyborane) (1068)

TG 6, x-Fold 0.65, SOC IC50 3 4M 4,4'-Dibromobiphenyl (312 mg) was dissolved in ether (10 mL), and the mixture was cooled to −100° C. Thereto was added 1N sec-butyllithium (2.1 mL) and the mixture was stirred for 30 min to −78° C. (SOLUTION A). 4,4'-Dibromodiphenylether (328 mg) was dissolved in ether (10 ml), and the mixture was cooled to −78° C. Thereto was added 1N sec-butyllithium (2.1 ml) and the mixture was stirred for 30 min. Triisopropoxyborane (376 mg) was added and the mixture was stirred to −65° C. (SOLUTION B). SOLUTION A and SOLUTION B were mixed, and the mixture was gradually warmed and stirred at room temperature for 15 hr. The mixture was acidified with 1N hydrochloric acid, and the organic layer was washed with water, dried, and concentrated to give the title compound (114 mg).

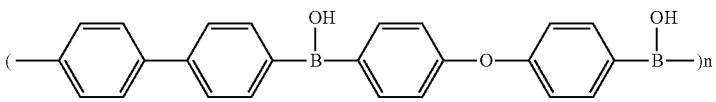

Example 37 poly(4,4'-biphenylene-dimethylaminoethoxyborane 4,4'-diphenyletherdimethylaminoethoxyborane) (1074)

TG −22, x-Fold 0.73

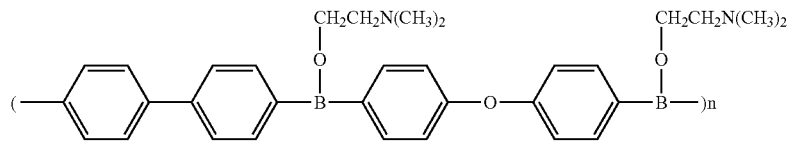

Example 38 poly(4,4'-biphenylene-aminoethoxyborane-4,4'-diphenylether aminoethoxyborane) (1077)

TG 79, x-Fold 0.71

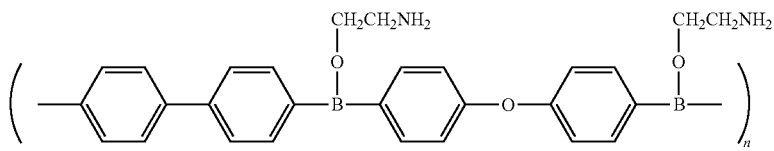

Example 39 poly(phenyleneaminoethoxyborane diphenylether-aminoethoxyborane) (1060)

TG 99, x-Fold 1.04

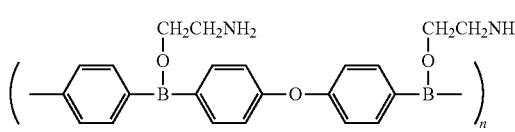

Example 40 poly(phenyleneaminoethylthioborane diphenylether-aminoethylthioborane) (1062)

TG 26, x-Fold 0.52

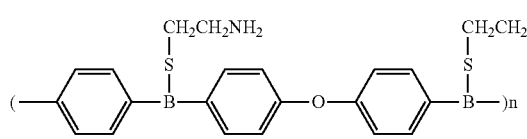

Example 41 poly(phenylene 2-piperazinomethoxyborane diphenylether 2-piperidinomethoxyborane) (1063)

TG 54, x-Fold 0.63, SOC IC50 2 μM

Example 42

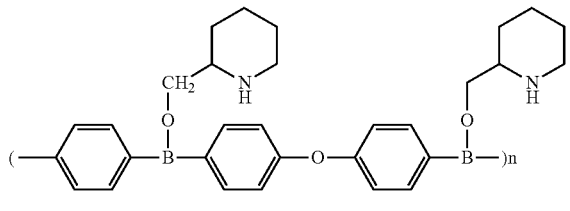

poly(methylaminoethoxyborylphenylene methylaminoethoxyboryldiphenylether) (1064)

TG 8, x-Fold 0.53, SOC IC50 2 μM

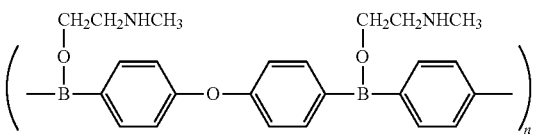

Example 43 poly(pyrrolidinomethoxyborylphenylene pyrrolidinomethoxyboryldiphenylether) (1065)

TG 13, x-Fold 0.73, SOC IC50 3 μM

Example 44 poly(aminoethylaminoethoxyborylphenylene aminoethylaminoethoxyboryldiphenylether) (1066)

TG 12, x-Fold 0.54, SOC IC50 4 μM

Example 45 poly(metaphenylene-hydroxyborane-4,4'-diphenyletherhydroxyborane) (1097)

TG 99, x-Fold 0.52

Example 46 poly(metaphenylene-2-piperidinemethoxyborane-4,4'-diphenylether-2-piperidinemethoxyborane) (1102)

TG 93, x-Fold 0.50

Example 47 poly(metaphenylene-aminoethoxyborane-4,4'-diphenylether aminoethoxyborane) (1103)

TG 106, x-Fold 0.58

Example 48 poly(metaphenylene-methylaminoethoxyborane-4,4'-diphenylethermethylaminoethoxyborane) (1104)

TG 102, x-Fold 0.59

Example 49 poly(metaphenylene-2-dimethylaminoethoxyborane-4,4'-diphenylether-2-dimethylaminoethoxyborane) (2102)

TG 89, x-Fold 0.96

Example 50 poly(metaphenylene-2-pyridyl-trifluoromethylphenylmethoxyborane-4,4'-diphenylether-2-pyridyl-trifluoromethylphenylmethoxyborane) (1105)

TG 112, x-Fold 0.59

Example 51 poly(metaphenylene-aminoethylthioborane-4,4'-diphenylether-aminoethylthioborane) (1106)

TG 13, x-Fold 0.43

Example 52 poly(4,4'-diphenyletherhydroxyborane phenylenemethyleneoxyphenylenehydroxyborane) (1069)

TG 73, x-Fold 0.69

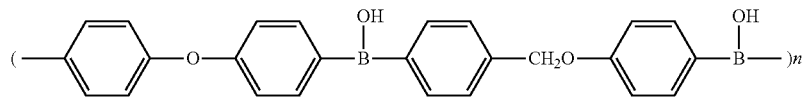

Example 53 poly(phenylenemethyleneoxyphenylene-aminoethoxyborane-4,4'-diphenyletheraminoethoxyborane) (1075)

TG 113, x-Fold 0.74

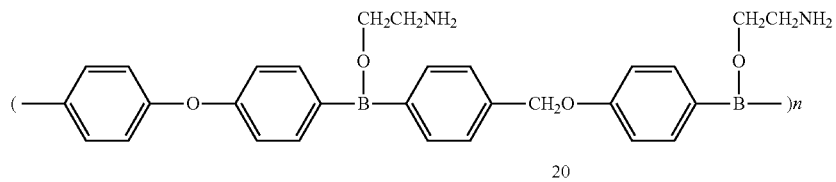

Example 54 poly(phenyleneoxyphenylene-2-pyrrolidinemethoxyboryl-phenylenemethyleneoxyphenylene-2-pyrrolidinemethoxyborane) (1080)

TG 112, x-Fold 0.67

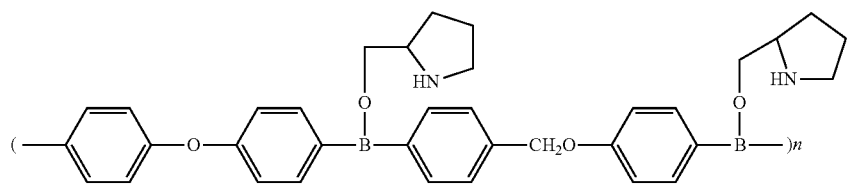

Example 55 poly(phenylenemethyleneoxyphenylene-dimethylaminoethoxyborane-4,4'-diphenylether dimethylaminoethoxyborane) (1081)

TG 151, x-Fold 0.71

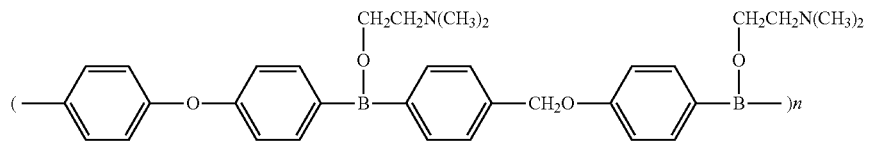

Example 56 poly(phenylenemethyleneoxyphenylene-2-pyridylmethoxyborane-4,4'-diphenylether-2-pyridylmethoxyborane) (1082)

TG 74, x-Fold 0.71

Example 57 poly(4,4'-biphenylene-aminoethoxyborane-1,4-phenylene-methyleneoxy-1,4-phenylene-aminoethoxyborane) (1125)

TG 5.98, x-Fold 0.67, SOC IC50 μM

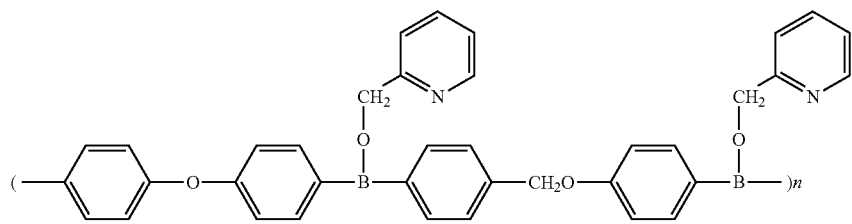

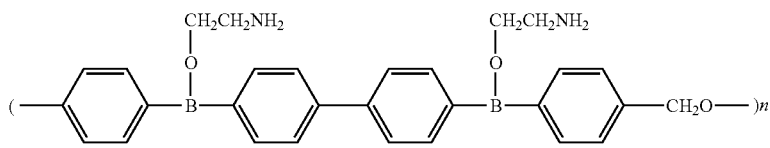

Example 58 poly(4,4'-biphenylene-dimethylaminoethoxyborane-1,4-phenylene-methyleneoxyphenylenedimethylaminoethoxyborane) (1124)

TG 45, x-Fold 0.62

4,4'-Dibromodibenzyl ether (96 mg) was dissolved in ether (6 ml), 1M sec-butyllithium (0.7 mL) was added and the mixture was stirred for 30 min. Triisoproxyborane (240 μL) was added at −78° C. and the mixture was stirred for 1 hr (SOLUTION A). 4,4'-Dibromodiphenyl ether (82.7 mg) was dissolved in ether (5 ml), 1N sec-butyllithium (0.7 mL) was added at −78° C. and the mixture was stirred (SOLUTION B). SOLUTION A and SOLUTION B were mixed at −78° C., and the mixture was gradually warmed to room temperature and stirred overnight. 1N Hydrochloric acid was added, and the ether layer was washed with saturated brine, dried, and concentrated to give the title compound (150 mg).

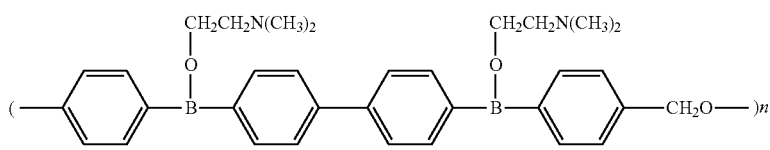

Example 59 poly(4,4'-biphenylene-2-pyridylmethoxyborane-1,4-phenylene-methyleneoxy-1,4-phenylene-2-pyridyl-methoxyborane) (1126)

TG 107, x-Fold 0.72

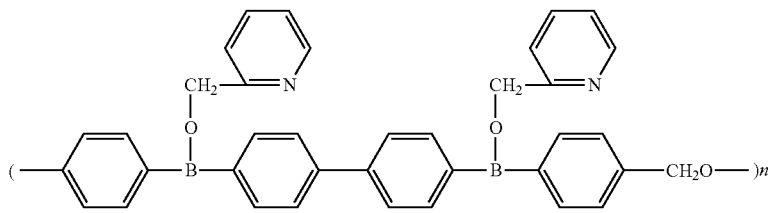

Example 60 poly(4,4'-biphenylene-2-hydroxyethylaminoethoxyborane-1,4-phenylene-methyleneoxy-1,4-phenylene-2-hydroxyethylaminoethoxyborane) (1127)

TG 24, x-Fold 0.73

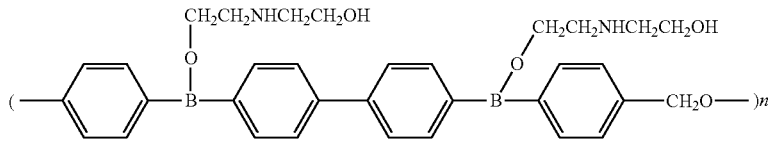

Example 61 poly(4,4'-phenylene-methyleneoxymethylene-phenylene-hydroxyborane-4,4'-phenyleneoxyphenyleneborinic acid) (1123)

TG 100, x-Fold 0.99

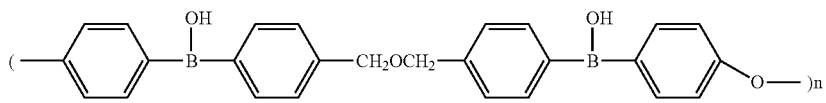

Example 62 poly(phenylene-methyleneoxymethylene-phenylene-aminoethoxyborane-phenyleneoxyphenyleneaminoethoxyborane) (1135)

TG 94, x-Fold 0.95

Example 66 poly(1,4-phenylene-methyleneoxymethylenephenylenemethylaminoethoxyborane-1,4-phenylene-methylaminoethoxyborane) (1144)

TG 120, x-Fold 1.18, SOC IC50 >20 μM

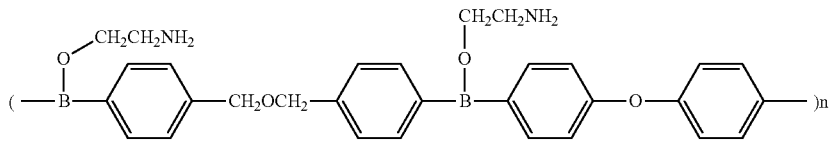

Example 63 poly(phenylene methyleneoxymethylene phenylene dimethylaminoethoxyborane phenylene oxy phenylene dimethylaminoethoxyborane) (1136)

TG 63, x-Fold 1.04

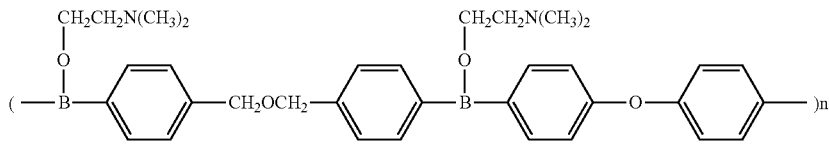

Example 64 poly(phenylene methyleneoxymethylene phenylene aminoethylthioborane phenylene oxy phenylene aminoethylthioborane) (1137)

TG 11, x-Fold 0.95

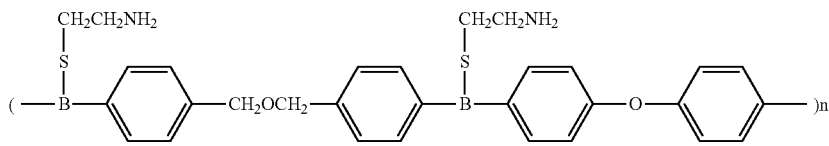

Example 65 poly(diphenylene-methylaminoethoxyboryl-1,4-phenylene-methyleneoxymethylenephenylene-methylaminoethoxyborane) (1142)

TG 115, x-Fold 1.02, SOC IC50 7 μM

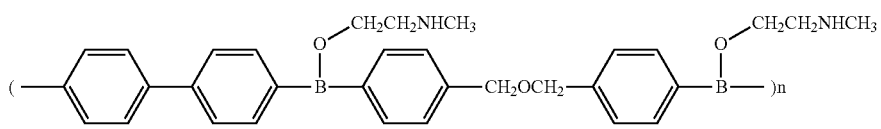

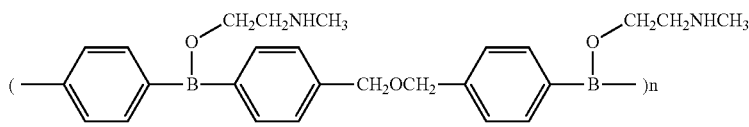

Example 67 poly(1,4-phenylene-methyleneoxymethylenephenylene-aminoethylaminoethoxyborane-1,4-phenylene-aminoethylaminoethoxyborane) (1145)

TG 122, x-Fold 0.87

4,4'-Parabrombenzyl ether (180 mg) was dissolved in ether (10 mL), and the mixture was cooled to −78° C. 1.57N tert-Butyllithium (0.7 mL) was added and the mixture was stirred for 60 min (SOLUTION A). 1,4-Dibromobenzene (118 mg) was dissolved in ether (10 mL), and the mixture was cooled to −78° C. 1.57N tert-Butyllithium (0.7 mL) was added and the mixture was stirred for 30 min. Triisopropoxyborane (188 mg) was added and the mixture was stirred to −65° C. (SOLUTION B). SOLUTION A and SOLUTION B were mixed, and the mixture was gradually warmed to room temperature and stirred for 15 hr. The mixture was acidified with 1N hydrochloric acid, and the organic layer was washed with water, dried, and concentrated to give the title compound (184 mg).

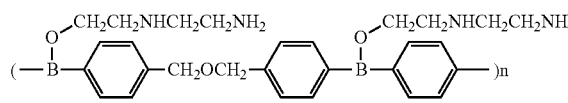

Example 68 polytetramethyleneborinic acid (6060)

TG 119, x-Fold 1.04

1,4-Tetramethylenedibromide (262 mg) was dissolved in ether (10 ml), and reacted with magnesium (Mg) (58 mg). Trimethoxyboroxin (60 μL) was added and the mixture was stirred overnight. Hydrochloric acid was added and the ether layer was concentrated to give the title compound (43.8 mg).

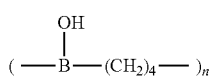

Example 69

2-dimethylaminoethyl bis(4-trifluoromethylphenyl)borinate (5034)

TG 76, x-Fold 1.02

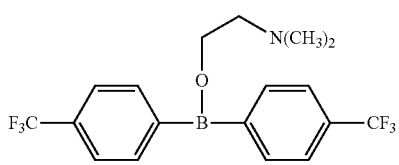 [SMILES: CN(C)CCOB(c1ccc(C(F)(F)F)cc1)c1ccc(C(F)(F)F)cc1]

Example 70

1,3-dimethylaminopropyl bis(3-chloro-4-methylphenyl)borinate (5141)

TG 13, x-Fold 0.73, SOC IC50 0.3 μM

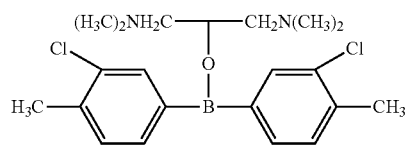

Example 71 di(3-chloro-4-methylphenyl)(2,3-diaminopropionate-O,N)borane (5142)

TG 51, x-Fold 0.97, SOC IC50 1 μM

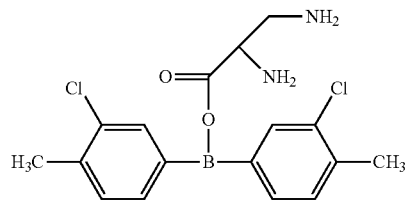

Example 72 di(3-chloro-4-methylphenyl)piperazinoethoxyborane (5143)

TG 41, x-Fold 1.02, SOC IC50 0.5 μM

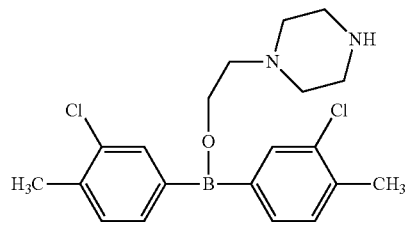

Example 73 di(3-chloro-4-methylphenyl)piperidinoethoxyborane (5144)

TG 35, x-Fold 0.85, SOC IC50 1.2 μM

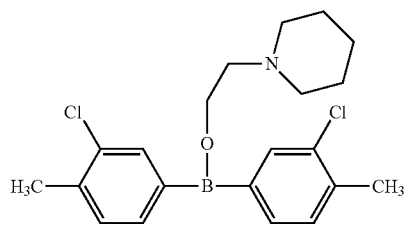

Example 74 di(3-chloro-4-methylphenyl)-2-piperidinoethoxyborane (5145)

TG 41, x-Fold 0.95, SOC IC50 1 µM

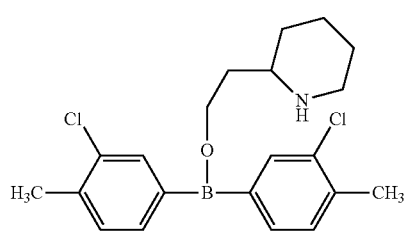

Example 75 bis(4-trifluoromethylphenyl)borinic acid (6001)

TG 97, x-Fold 0.88

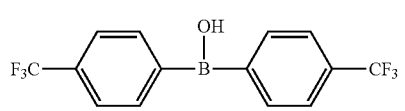 [SMILES: OB(c1ccc(C(F)(F)F)cc1)c1ccc(C(F)(F)F)cc1]

Example 76 bis(3-chloro-4-fluorophenyl)borinic acid (6004)

TG 117, x-Fold 0.78

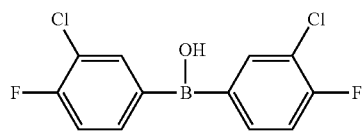 [SMILES: OB(c1ccc(F)c(Cl)c1)c1ccc(F)c(Cl)c1]

Example 77

2-aminoethyl-bis(3-chloro-4-fluorophenyl)borinate (6006)

TG 98, x-Fold 0.91

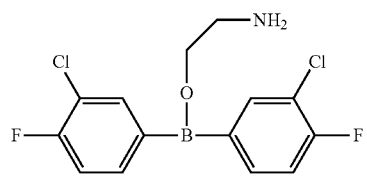 [SMILES: NCCOB(c1ccc(F)c(Cl)c1)c1ccc(F)c(Cl)c1]

Example 78

2-dimethylaminoethyl bis(3-chloro-4-fluorophenyl)borinate (6007)

TG 104, x-Fold 1.02

Example 79 bis(4-chloro-2-fluorophenyl)borinic acid (6008)

TG 97, x-Fold 0.88

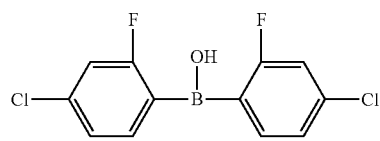 [SMILES: OB(c1ccc(Cl)cc1F)c1ccc(Cl)cc1F]

Example 80 bis(3,4-difluorophenyl)borinic acid (6009)

TG 93, x-Fold 0.90

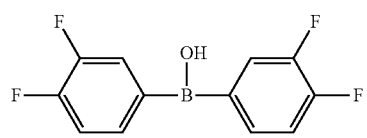

Example 81 bis(3,4,5-trifluorophenyl)borinic acid (6010)

TG 97, x-Fold 0.92

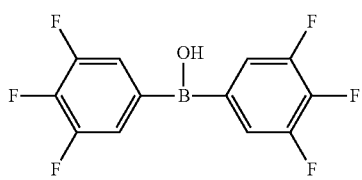 [SMILES: OB(c1cc(F)c(F)c(F)c1)c1cc(F)c(F)c(F)c1]

Example 82 bis(2,4-difluorophenyl)borinic acid (6011)

TG 103, x-Fold 0.95

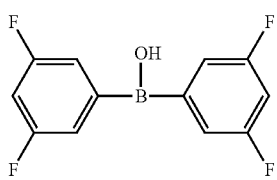 [SMILES: OB(c1cc(F)cc(F)c1)c1cc(F)cc(F)c1]

Example 83 bis(3-fluoro-4-chlorophenyl)borinic acid (6012)

TG 101, x-Fold 0.92

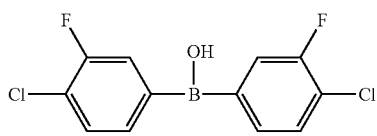 [SMILES: OB(c1ccc(Cl)c(F)c1)c1ccc(Cl)c(F)c1]

Example 84

2-aminoethyl bis(4-chloro-2-fluorophenyl)borinate (6013)

TG 91, x-Fold 0.92

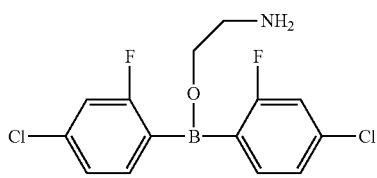 [SMILES: NCCOB(c1ccc(Cl)cc1F)c1ccc(Cl)cc1F]

Example 85 poly(4,4'-biphenylhydroxyborane) (504)

TG 128, x-Fold 0.79

4,4'-Dibromodiphenyl (234 mg) was dissolved in ether (10 ml), and 1.5N tert-butyllithium (1.3 mL) was added at −95° C. 30 min later, triisoproxyborane (345 µL) was added at −78° C. and the mixture was stirred for 1 hr (SOLUTION A). 4,4'-Dibromodiphenyl (234 mg) was dissolved in ether (10 mL), 1.5N tert-butyllithium (1.3 mL) was added at −95° C. and the mixture was stirred (SOLUTION B). SOLUTION A and SOLUTION B were mixed at −78° C., and the mixture was gradually warmed to room temperature and stirred overnight. 1N Hydrochloric acid solution was added and the ether layer was with washed with saturated brine and dried and concentrated to give the title compound (155 mg).

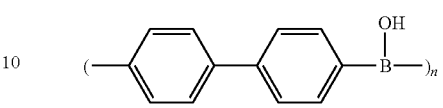

Example 86

2-aminoethyl bis(3-chloro-4-fluorophenyl)borinate (6015)

TG 103, x-Fold 0.99

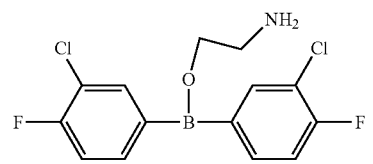 [SMILES: NCCOB(c1ccc(F)c(Cl)c1)c1ccc(F)c(Cl)c1]

Example 87

2-aminoethyl bis(3,4-difluorophenyl)borinate (6016)

TG 91, x-Fold 1.02

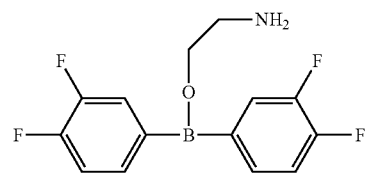 [SMILES: NCCOB(c1ccc(F)c(F)c1)c1ccc(F)c(F)c1]

Example 88

2-amino-1-phenylethyl bis(3,4-difluorophenyl)borinate (6017)

TG 82, x-Fold 0.83

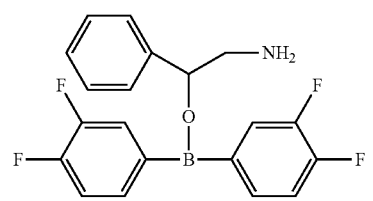 [SMILES: NCC(OB(c1ccc(F)c(F)c1)c1ccc(F)c(F)c1)c1ccccc1]

Example 89 aminoethyl bis(3,4,5-trifluorophenyl)borinate (6018)

TG 80, x-Fold 0.94

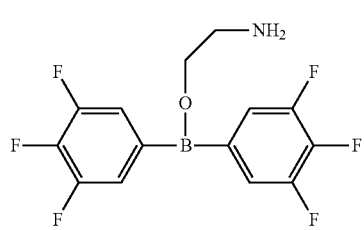 [SMILES: NCCOB(c1cc(F)c(F)c(F)c1)c1cc(F)c(F)c(F)c1]

Example 90

2-pyridylmethyl bis(3,4,5-trifluorophenyl)borinate (6019)

TG 93, x-Fold 0.81

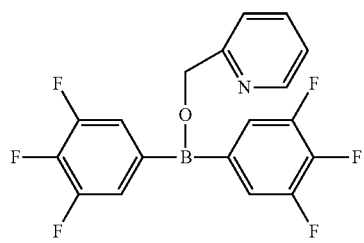 [SMILES: Fc1cc(B(OCc2ccccn2)c2cc(F)c(F)c(F)c2)cc(F)c1F]

Example 91 aminoethyl bis(3,5-difluorophenyl)borinate (6020)

TG 107, x-Fold 0.99

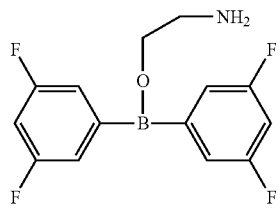 [SMILES: NCCOB(c1cc(F)cc(F)c1)c1cc(F)cc(F)c1]

Example 92 dimethylaminoethyl bis(3,5-difluorophenyl)borinate (6021)

TG 106, x-Fold 1.00

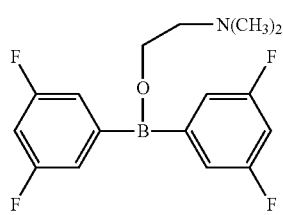

Example 93 aminoethyl bis(4-chloro-3-fluorophenyl)borinate (6023)

TG 117, x-Fold 0.93

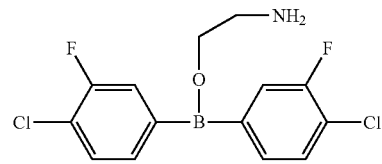

Example 94 dimethylaminoethyl bis(4-chloro-3-fluorophenyl)borinate (6024)

TG 114, x-Fold 0.95

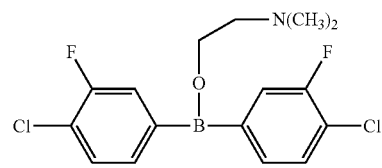 [SMILES: CN(C)CCOB(c1ccc(Cl)c(F)c1)c1ccc(Cl)c(F)c1]

Example 95 di(3-fluoro-4-chlorophenyl)(2,4-diaminolactonate-O,N)borane (6025)

TG 114, x-Fold 0.88

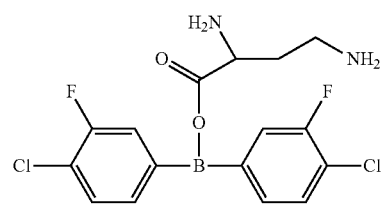 [SMILES: NCCC(N)C(=O)OB(c1ccc(Cl)c(F)c1)c1ccc(Cl)c(F)c1]

Example 96 di(3-fluoro-4-chlorophenyl)(glutaminate-O,N)borane (6026)

TG 124, x-Fold 0.86

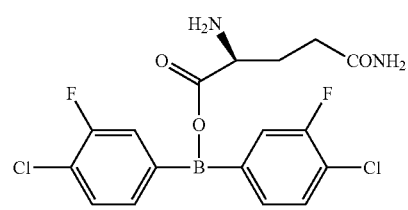 [SMILES: NC(=O)CC[C@H](N)C(=O)OB(c1ccc(Cl)c(F)c1)c1ccc(Cl)c(F)c1]

Example 97 bis(3-chloro-5-fluorophenyl)borinic acid (6027)

TG 122, x-Fold 0.72

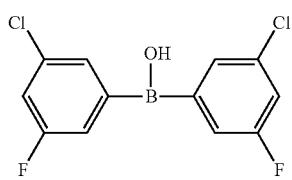 [SMILES: OB(c1cc(F)cc(Cl)c1)c1cc(F)cc(Cl)c1]

Example 98 bis(3-chloro-6-fluorophenyl)borinic acid (6029)

TG 111, x-Fold 0.95

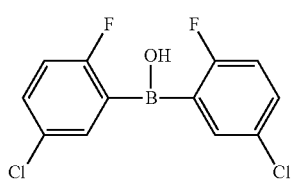

Example 99 aminoethyl bis(3-chloro-5-fluorophenyl)borinate (6030)

TG 109, x-Fold 0.73

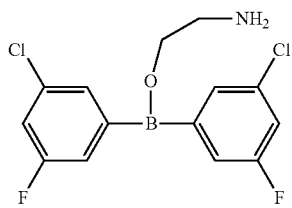 [SMILES: NCCOB(c1cc(F)cc(Cl)c1)c1cc(F)cc(Cl)c1]

Example 100 aminoethyl bis(3-chloro-6-fluorophenyl)borinate (6032)

TG 119, x-Fold 0.97

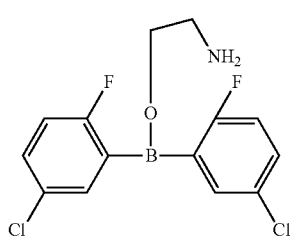 [SMILES: NCCOB(c1cc(Cl)ccc1F)c1cc(Cl)ccc1F]

Example 101 methylaminoethyl bis(3-chloro-6-fluorophenyl)borinate (6033)

TG 122, x-Fold 1.02

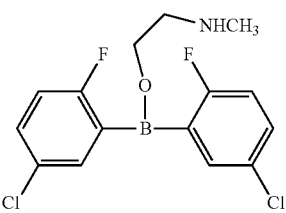 [SMILES: CNCCOB(c1cc(Cl)ccc1F)c1cc(Cl)ccc1F]

Example 102 bis(4-cyanophenyl)borinic acid (5009)

TG 72, x-Fold 1.10

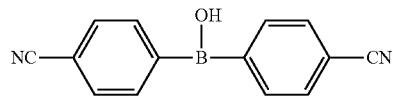 [SMILES: N#Cc1ccc(B(O)c2ccc(C#N)cc2)cc1]

Example 103 aminoethyl bis(4-cyanophenyl)borinate (6034)

TG 114, x-Fold 0.89

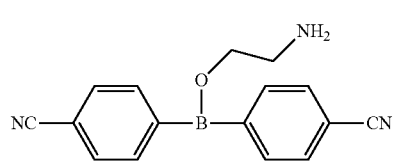 [SMILES: N#Cc1ccc(B(OCCN)c2ccc(C#N)cc2)cc1]

Example 104

2-pyridylmethyl bis(4-cyanophenyl)borinate (6037)

TG 94, x-Fold 1.16

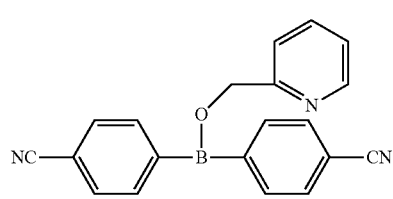 [SMILES: N#Cc1ccc(B(OCc2ccccn2)c2ccc(C#N)cc2)cc1]

Example 105 benzylaminoethyl bis(4-cyanophenyl)borinate (6038)

TG 92, x-Fold 1.05

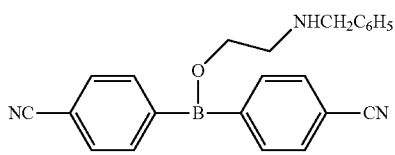

Example 106

2-aminoethylthio bis(4-cyanophenyl)borane (6039)

TG 23, x-Fold 0.92

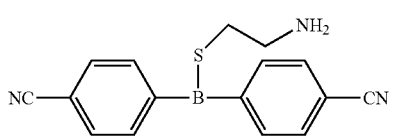 [SMILES: N#Cc1ccc(B(SCCN)c2ccc(C#N)cc2)cc1]

Example 107 secondary-butyl phenyl borinic acid (6040)

TG 111, x-Fold 0.98

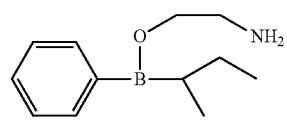

Example 111 aminoethyl tertiary-butyl phenylborinate (6044)

TG 121, x-Fold 1.02

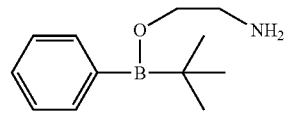

Example 112 aminoethyl normal-butyl phenylborinate (6046)

TG 123, x-Fold 0.99

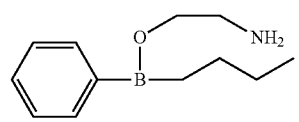

Example 113

1,4-bis(hydroxyphenylboryl)butane (6059)

TG 112, x-Fold 0.99

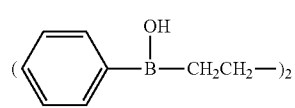

Example 114

4-hydroxybutylphenylborinic acid (6059-9)

TG 120, x-Fold 0.99, SOC IC50 2 µM

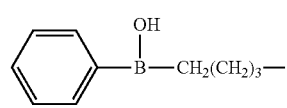

Example 108 normal-butyl phenyl borinic acid (6041)

TG 111, x-Fold 1.00

Example 109 tertiary-butyl phenyl borinic acid (6042)

TG 108, x-Fold 1.02, SOC IC50 >10 µM

Example 110 aminoethyl secondary-butyl phenylborinate (6043)

TG 115, x-Fold 1.02, SOC IC50 >10 µM

Example 115 bis(4-chlorophenyl)borinic acid (385)

TG 101, x-Fold 1.07

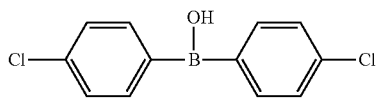

Example 116 bis(di(3-chloro-4-methylphenyl)boryloxyethyl)piperazine (419)

TG 108, x-Fold 1.02

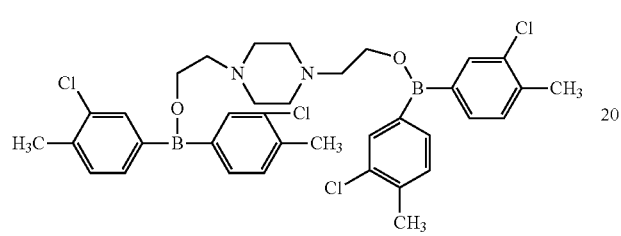

Example 117 bis(3-chloro-4-methylphenyl 2-pyridylmethoxyborylphenyl)ether (434)

TG 108, x-Fold 0.06, SOC IC50 1.5 µM

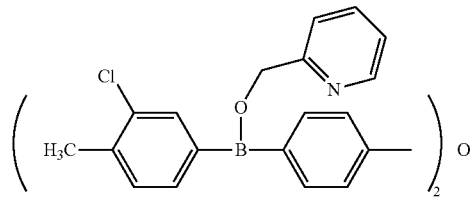

Example 118

1,4-bis(phenyl-2-aminoethoxyboryl)benzene (544)

TG 93, x-Fold 0.97, SOC IC50 2 µM

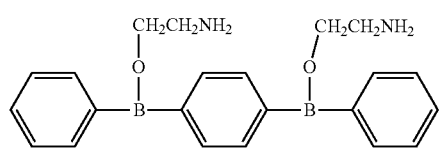

Example 119

1,3-bis(phenylhydroxyboryl)benzene (554)

TG 101, x-Fold 0.84, SOC IC50 >20 µM

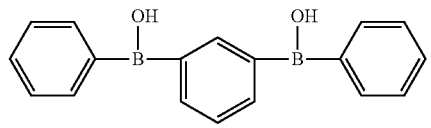 [SMILES: OB(c1ccccc1)c1cccc(B(O)c2ccccc2)c1]

Example 120

1,3-bis(phenyl-2-aminoethoxyboryl)benzene (805)

TG 88, x-Fold 1.08

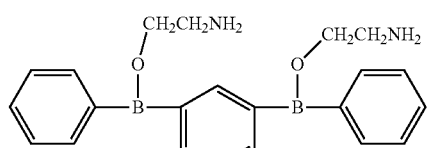

Example 121

1,2-bis(phenylhydroxyboryl)benzene (583)

TG 121, x-Fold 0.94

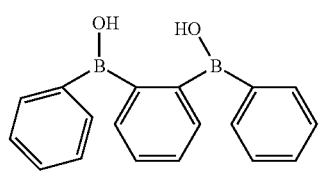 [SMILES: OB(c1ccccc1)c1ccccc1B(O)c1ccccc1]

Example 122 diphenyl(argininate-O,N)borane (880)

TG 93, x-Fold 0.98, SOC IC50 7 µM

Arginine (82 mg) and 2-aminoethyldiphenylborinate (112 mg) were stirred in ethanol (0.4 ml), water (1.5 ml) and acetic acid (0.9 ml) at 110° C. for 3 hr to give the title compound (17 mg).

The present compound were also obtained by heating arginine hydrochloride (211 mg) and sodium tetraphenylborate (342 mg) in water (5 mL) at 100° C. for 3 hr.

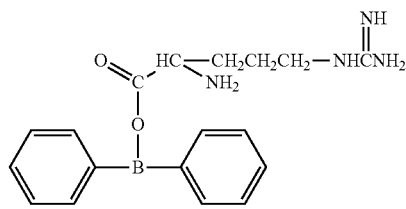

Example 123 diphenyl(glutaminate-O,N)borane (870)

TG 98, x-Fold 0.84, SOC IC50 1 µM

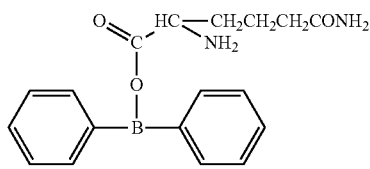

Example 124

(2-phenylhydroxyborylbenzyl)(3-(phenylhydroxybo-ryl)benzyl)ether (656)

TG 90, x-Fold 0.96

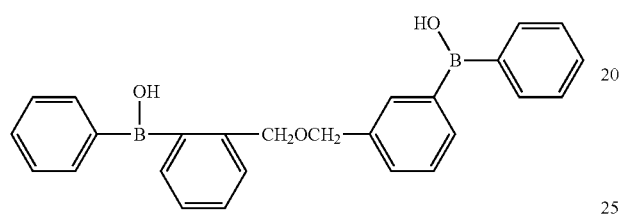

Example 125 bis(3-chloro-4-methylphenyl hydroxyborylbenzyl)ether (595)

TG 113, SOC IC50 10 μM

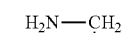
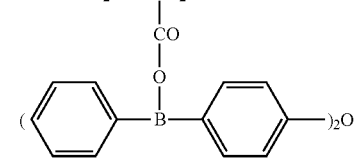

Example 126 bis(phenyl 2-pyridyl-4-methoxyphenylmethoxyborylbenzyl)ether (601)

TG 81, x-Fold 1.04

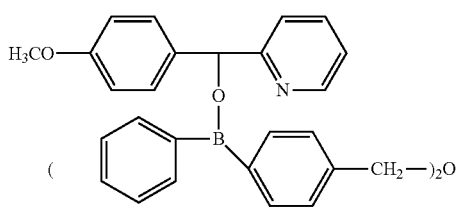

Example 127 bis(3-chloro-4-methylphenyl) 2-pyridyl-4-methoxyphenylmethoxyborane (592)

TG 109, x-Fold 0.70

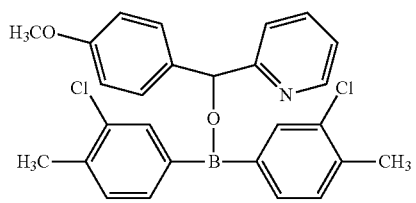

Example 128

1,4-bis(3-chloro-4-methylphenyl-2-aminoethoxybo-ryl)benzene (573)

TG 143, x-Fold 0.93

Example 129 di((phenylglycine-O,N boryl)phenyl)ether (1016)

TG 101, x-Fold 0.78

Example 130

1,3,5-tri(phenylhydroxyboryl)benzene (563)

TG 116, x-Fold 0.85

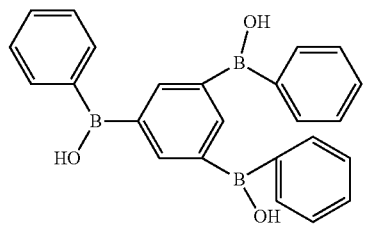 [SMILES: OB(c1ccccc1)c1cc(B(O)c2ccccc2)cc(B(O)c2ccccc2)c1]

Example 131 bis((4,4'-phenylaminoethoxyboryl)benzyl)ether (163AE)

TG 16, x-Fold 1.1, SOC IC50 0.3 μM

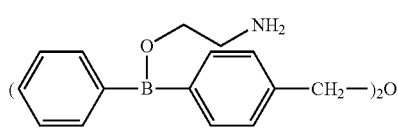

Example 132

1,3,5-tri(2-pyridyl-4-trifluoromethylphenylmethoxyphenylboryl)benzene (567)

TG 88, x-Fold 0.95

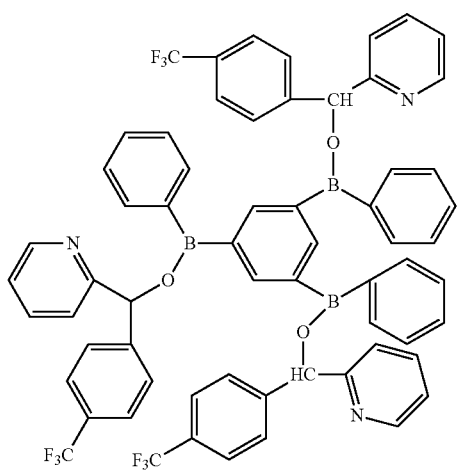 [SMILES: FC(F)(F)c1ccc(C(OB(c2ccccc2)c2cc(B(OC(c3ccc(C(F)(F)F)cc3)c3ccccn3)c3ccccc3)cc(B(OC(c3ccc(C(F)(F)F)cc3)c3ccccn3)c3ccccc3)c2)c2ccccn2)cc1]

Example 133

(2-pyridyl-phenylmethoxyphenylboryl 2-benzyl)ether (566)

TG 106, x-Fold 1.00

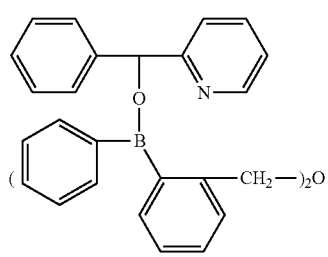

Example 134

(2-pyridyl-4-trifluoromethylphenylmethoxyphenylboryl 2-benzyl)ether (558)

TG 94, x-Fold 0.92

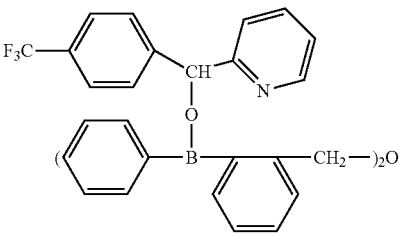

Example 135

1,4-bis(phenylhydroxyboryl)naphthalene (602)

TG 99, x-Fold 1.03

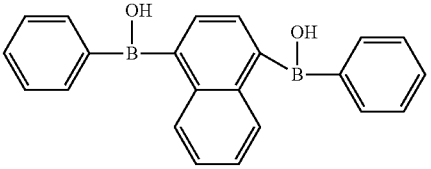 [SMILES: OB(c1ccccc1)c1ccc(B(O)c2ccccc2)c2ccccc12]

Example 136 diphenyl(asparaginate-O,N)borane (871)

TG 96, x-Fold 0.98

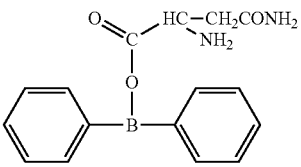

Example 137 bis((4,4'-phenylhydroxyboryl)benzyl)ether (163OH)

TG 14, x-Fold 0.99, SOC IC50 0.3 µM

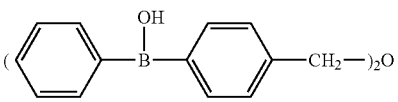

Example 138 bis(2-pyridyl-4-trifluoromethylphenylmethoxyphenylboryl 4-benzyl)ether (607)

TG 96, x-Fold 0.99

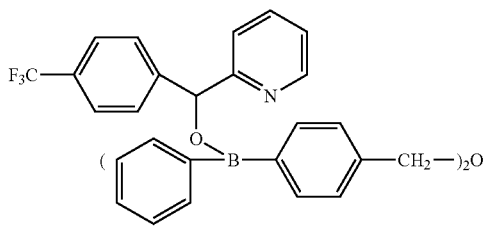

Example 139 bis(4-chloro-3-methylphenylhydroxyboryl 4-benzyl)ether (611)

TG 122, x-Fold 0.88

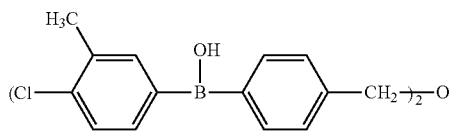

Example 140

4,4'-phenylhydroxyboryl 4-biphenyl (548)

TG −72, x-Fold 0.85

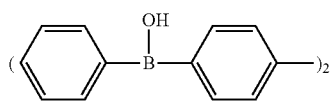

Example 141 bis(4,4'-(1-naphthylhydroxyboryl)benzyl)ether (620)

TG 97, x-Fold 0.92

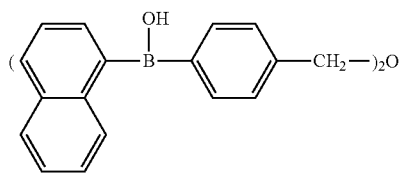

Example 142 bis(4-fluorophenylhydroxyboryl 4-benzyl)ether (621)

TG 88, x-Fold 0.24

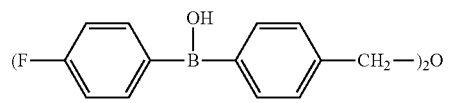

Example 143 bis(4-trifluoromethylphenylhydroxyboryl 4-benzyl)ether (618)

TG 118, x-Fold 0.90

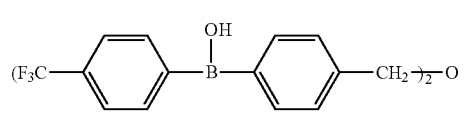

Example 144 bis(3-chloro-4-methylphenylhydroxyboryl 4-benzyl)ether (612)

TG 99, x-Fold 0.87

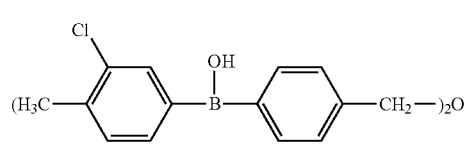

Example 145

(3-chloro-4-fluorophenyl)boronic acid (6005)

TG 97, x-Fold 0.91

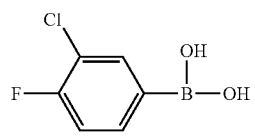

Example 146

1,4-bis(phenyl-2-aminoethoxyboryl) 2-methylbenzene (803)

TG 91, x-Fold 1.02

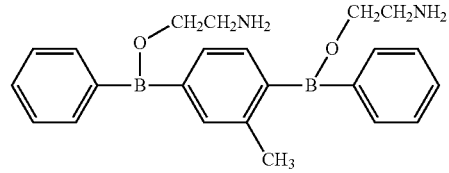

Example 147

1,3-bis(phenylhydroxyboryl)benzene (554)

TG 101, x-Fold 0.87, SOC IC50 20 μM

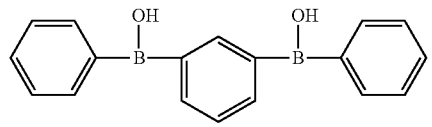 [SMILES: OB(c1ccccc1)c1cccc(B(O)c2ccccc2)c1]

Example 148 bis(2,2'-(phenyl-2-aminoethoxyboryl)benzyl)ether (557)

TG 68, x-Fold 1.00

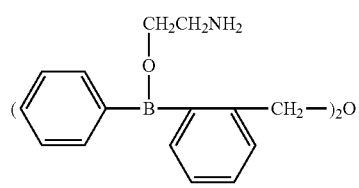

Example 149

4,4'-di((phenyl 1-(pyridin-2-yl)-1-trifluoromethylphenylmethoxyboryl)benzyl)ether (607)

TG 96, x-Fold 0.99

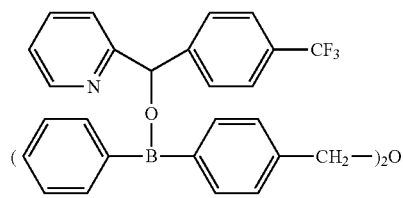

Example 150 diphenyl-2-aminophenylthioborane (4122)

TG 2, x-Fold 0

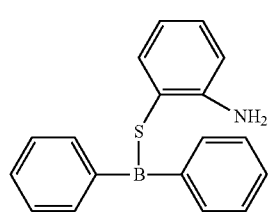 [SMILES: Nc1ccccc1SB(c1ccccc1)c1ccccc1]

Example 151

2-aminoethylthiodiphenylborane (1031)

TG 33, x-Fold 0.87

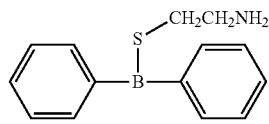

Example 152 di(4,4'-phenyldimethylaminoethoxyboryl)benzylether (1073)

TG54, x-Fold 1.07

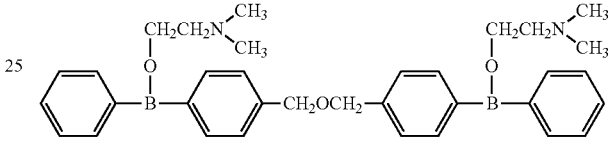

Example 153 poly(4,4'-biphenylene-2-pyridyl-4-trifluoromethylphenylmethoxyborane 4,4'-diphenylether 2-pyridyl-4-trifluoromethoxyborane) (1079)

TG 65, x-Fold 0.79

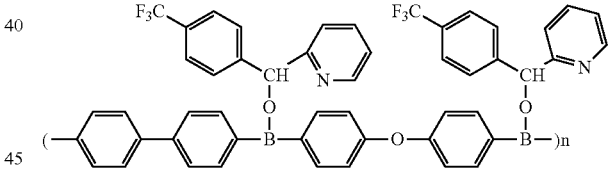

Example 154 diphenyl 2-aminoethylaminoethyl borinate (1089)

TG 105, x-Fold 0.96-

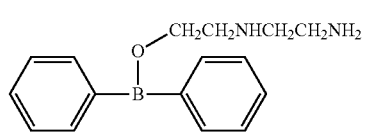

Example 155 di(trifluoromethylphenyl) 2-pyridinomethylborinate (427)

TG 100, x-Fold 1.02

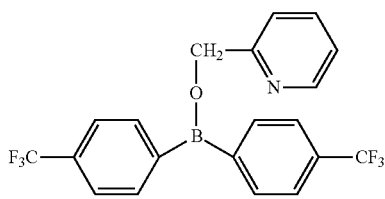 [SMILES: FC(F)(F)c1ccc(B(OCc2ccccn2)c2ccc(C(F)(F)F)cc2)cc1]

Example 156 di(3-chloro-6-methyl-phenyl)(argininate-O,N)borane (7138)

TG 91, x-Fold 1.08

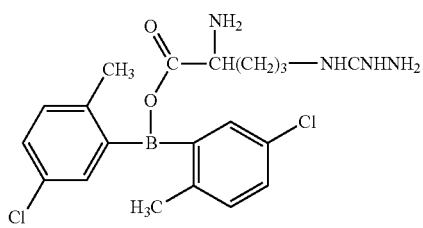

Example 157 poly(phenylenemethyleneoxyphenyleneaminoethoxyborane) (1116)

TG 96, x-Fold 0.73

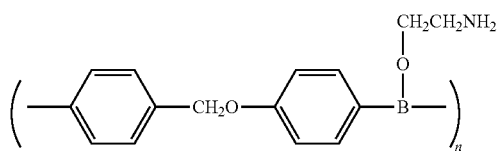

Example 158 poly(phenylenemethyleneoxyphenyleneaminoethylthioborane) (1117)

TG 12, x-Fold 0.69

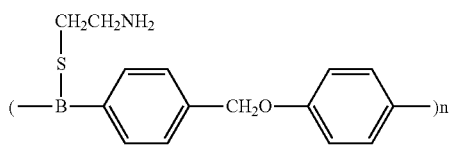

Example 159 dibutyl(alanine-O,N)borane (926)

TG 102, x-Fold 0.96

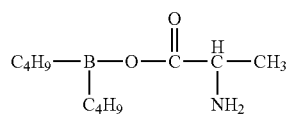

Example 160 di(3-chloro-6-methyl-phenyl)(citrullinate-O,N)borane (7139)

TG 88, x-Fold 1.02

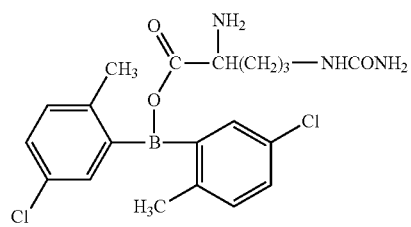

Example 161

FITC aminoethylaminoethyl diphenylborinate (1098)

TG 6, x-Fold 0.99

NHS-Florescein (Pierce: catalog No. 46100) (4.73 mg) was dissolved in DMF (100 μL), TEAB (pH 7.5) (100 μL) and diphenyl 2-aminoethylaminoethoxyborane (2.68 mg) were added, and the mixture was stirred at room temperature for 3 hr and applied to DEAE cellulose column for purification, whereby the title compound (8.1 mg) was obtained.

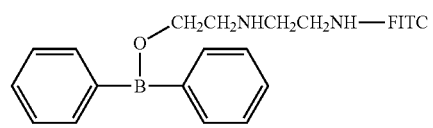

Example 162 tetramethylrhodamine aminoethylaminoethyl diphenylborinate (1099)

TG −2, x-Fold 0.85

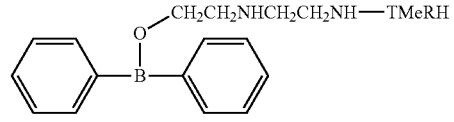

Example 163 di(3-chloro-4-methylphenyl)N-methylpiperidinomethylborinate (347)

TG 109, x-Fold 1.00

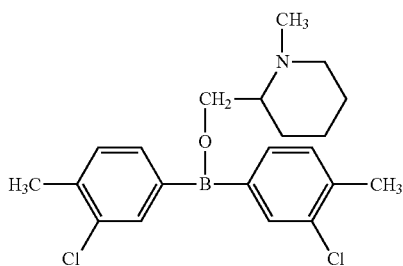

Example 164 di(3-chloro-6-methylphenyl)benzylaminoethylborinate (376)

TG 94, x-Fold 0.67

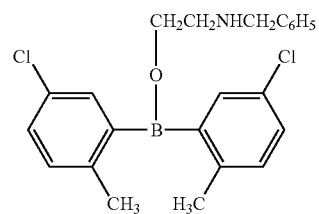

Example 165 poly(4,4'-biphenylene-methylaminoethoxyborane 1,4-phenylene methyleneoxymethylenephenylene-methylaminoethoxyborane) (1143)

TG 120, x-Fold 0.99

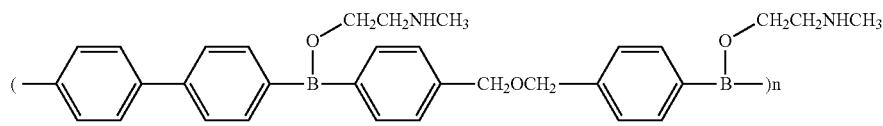

Example 166 di(3-chloro-6-methylphenyl)aminoethylborinate (372)

TG 74, x-Fold 0.70

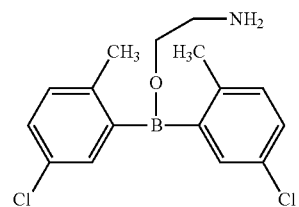 [SMILES: Cc1ccc(Cl)cc1B(OCCN)c1cc(Cl)ccc1C]

Example 167

(4-(phenyl-dimethylaminoethoxyboryl)phenyl)-(4'-(methoxymethoxymethylphenyl-dimethylaminoethoxyboryl)phenyl)ether (2006)

TG 21, x-Fold 0.71

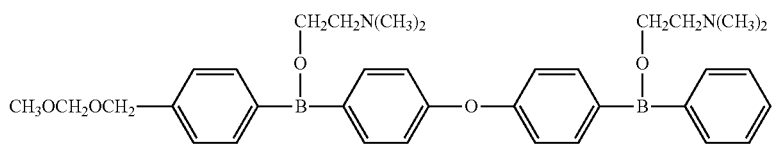

Example 168

(4-(phenyl-N-methylaminoethoxyboryl)phenyl)-(4'-(methoxymethoxymethylphenyl-N-methylaminoethoxyboryl)phenyl)ether (2007)

TG 35, x-Fold 0.72

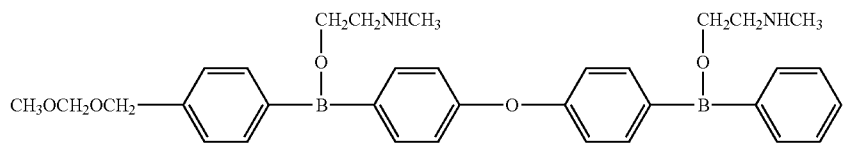

Example 169 di((phenylglycine-O,N boryl)phenyl)ether (1016)

TG 101, x-Fold 0.78

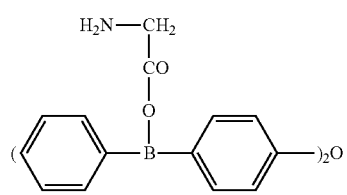

Example 170 diphenyl(glycylglutamine-O,N)borane (907)

TG 96, x-Fold 0.96

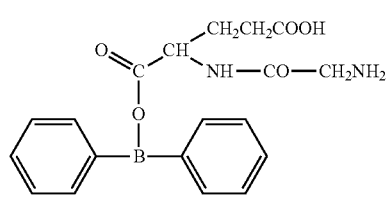

Example 171 di(3-chloro-6-methylphenyl)borinic acid (370)

TG 98, x-Fold 0.71

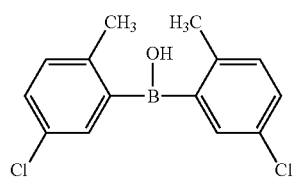

Example 172 bis(3,3'(phenyldimethylaminoethoxyboryl)benzyl)ether (2024)

TG 69, x-Fold 1.22

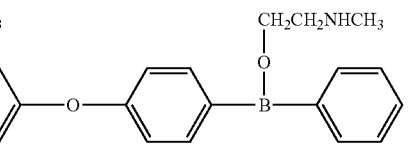

Example 173

(3,3'-(phenylpiperazino-O,O-ethoxyboryl)benzyl)ether (2026)

TG 122, x-Fold 1.06

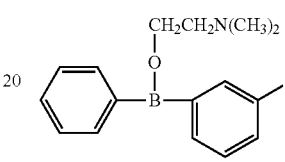

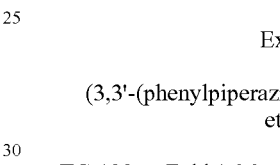

Example 174 diphenyl(2,3-diaminopropionate-O,N)borane (2031-4)

TG 103, x-Fold 0.99

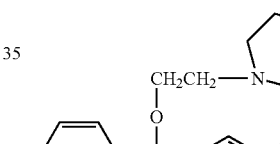
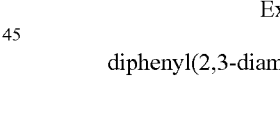
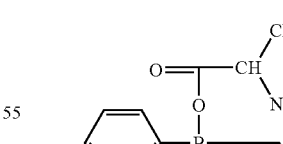

Example 175 diphenyl(tetramethylrhodamine 2,3-diaminopropionate-O,N)borane (2033)

TG 5, x-Fold 0.89

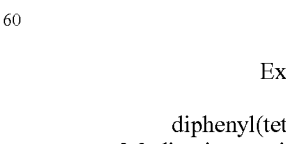

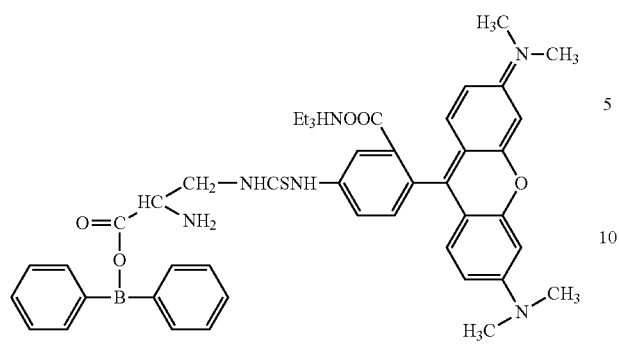

Example 176 diphenyl(tetramethylrhodamine 2,6-diaminocapronate-O,N)borane (2035)

TG 47, x-Fold 1.06

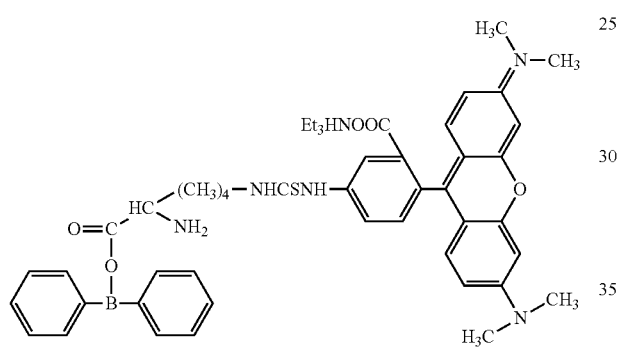

Example 177 diphenyl(FITC-2,6-diaminocapronate-O,N)borane (2036)

TG 28, x-Fold 1.00

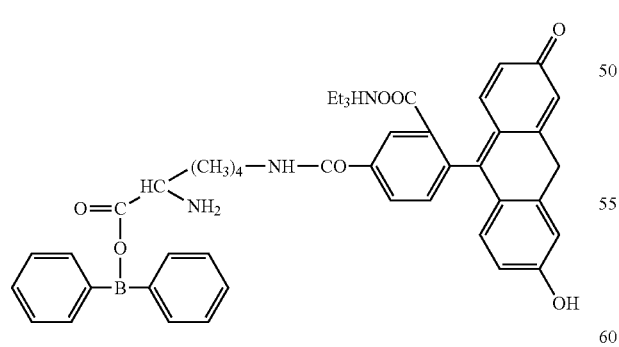

Example 178 diphenyl(2,3-diaminobutyrate-O,N)borane (2039)

TG 142, x-Fold 0.89

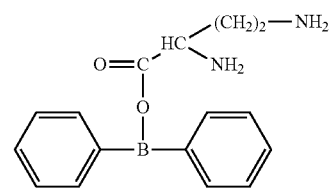

Example 179 diphenyl(2,5-diaminopentanate-O,N)borane (2044)

TG 127, x-Fold 0.99

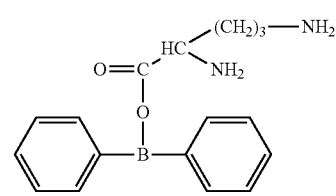

Example 180 di(3-chloro-4-methylphenyl)(anthranate-O,N)borane (4124)

TG 35, x-Fold 0.98

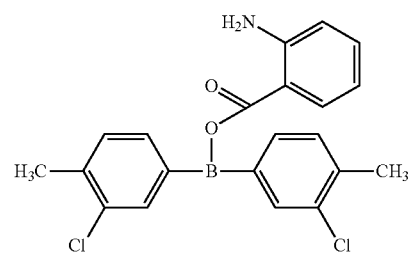

Example 181 di(trifluoromethylphenyl) 2-aminoethylborinate (424)

TG 54, x-Fold 0.69

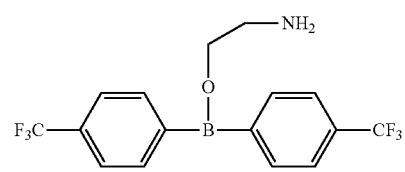 [SMILES: NCCOB(c1ccc(C(F)(F)F)cc1)c1ccc(C(F)(F)F)cc1]

Example 182 di(3-chloro-4-methylphenyl)(glutaminate-O,N)borane (4105)

TG 137, x-Fold 1.01

Di(3-chloro-4-methylphenyl)borinic acid (32 mg) and glutamine (15 mg) were reacted in ethanol (0.6 mL) at 90° C. for 2 hr to give the title compound (34 mg).

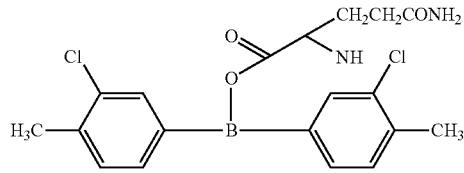

Example 183 dibutyl(asparagine-O,N)borane (925)

TG 91, x-Fold 1.02

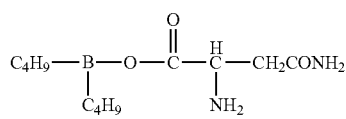

Example 184 di(4-(phenyl-2-pyridylmethoxyboryl)benzyl)ether (2049)

TG 94, x-Fold 0.95

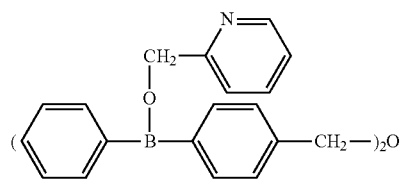

Example 185 bis(4,4'-(p-trifluoromethylphenyl-asparagineboryl)benzyl)ether (2064)

TG 130, x-Fold 0.94, SOC IC50 >20 μM

Aminoethyldiphenylborinate (112 mg) and piperazinecarboxylic acid (102 mg) were reacted in ethanol (0.6 mL) and acetic acid (30 mL) at 80° C. for 5 hr to give the title compound (36 mg).

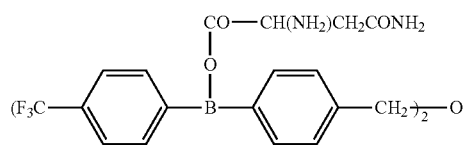

Example 186

Di(1-(pyridin-2-yl)-1-(4-methoxyphenyl)methyl-phenyl-borylbenzyl)ether (601)

TG 81, x-Fold 0.98

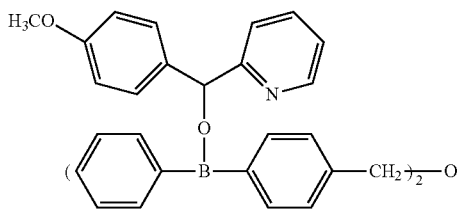

Example 187 bis((4,4'-phenylhydroxyboryl)benzyloxybenzyl)hydroxyborane (2086)

TG 106, x-Fold 0.97

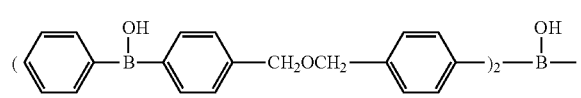

Example 188 di(trifluoromethylphenyl) 2-propylaminoethylborinate (428)

TG 91, x-Fold 0.98

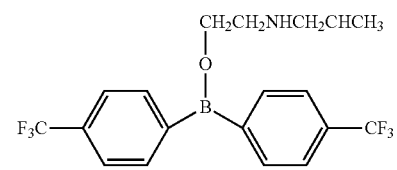

Example 189 bis((4,4'-phenylaminoethoxyboryl)benzyloxybenzyl) aminoethoxyborane (2088)

TG 119, x-Fold 0.94

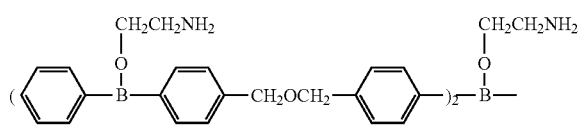

Example 190 bis((4,4'-phenyl methylaminoethoxyboryl)benzyloxybenzyl)methylaminoethoxyborane (2089)

TG 99, x-Fold 1.05

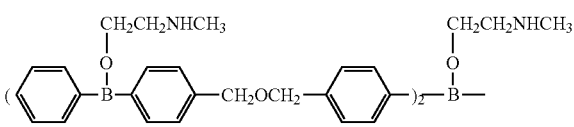

Example 191 bis((4,4'-phenyldimethylaminoethoxyboryl)benzyloxybenzyl)dimethylamino-ethoxyborane (2090)

TG 85, x-Fold 1.04

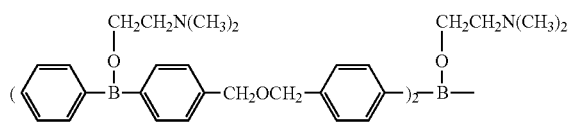

Example 192 bis((4,4'-phenyl 2-pyridyl-4-trifluoromethylphenylmethoxyboryl)benzyloxybenzyl) 2-pyridyl-4-trifluoromethyl phenylmethoxyborane (2091)

TG 102, x-Fold 0.95

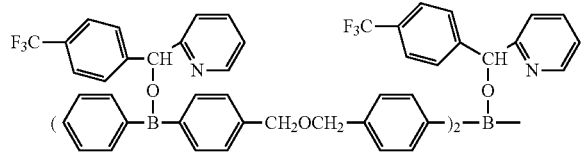

Example 193 diphenyl(2-piperazine-3-carboxyamide-carboxy) borane (899)

TG 92, x-Fold 1.03

Aminoethyldiphenylborinate (112 mg) and pyrazine 2,3-dicarboxylic acid monoamide (83 mg) were reacted in ethanol (0.5 mL) and acetic acid (30 mg) to give the title compound (40 mg).

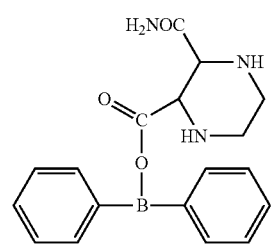 [SMILES: NC(=O)C1NCCNC1C(=O)OB(c1ccccc1)c1ccccc1]

Example 194 diphenyl(methionate-O,N)borane (901)

TG 106, x-Fold 1.03

The title compound (35 mg) was obtained from diphenylborinic acid (61 mg) and methionine (50 mg).

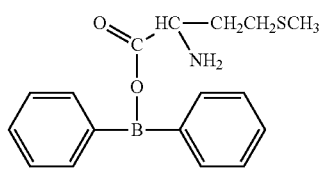

Example 195 di(phenyl 3-piperidinooxyboryl phenyl)ether (2108)

TG 115, x-Fold 0.77

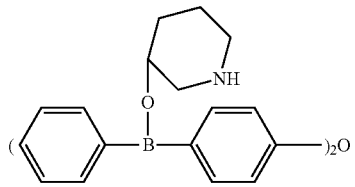

Example 196

4,4'-(phenyl piperazino-O,O-ethoxyboryl)phenylether (2109)

TG 117, x-Fold 0.90

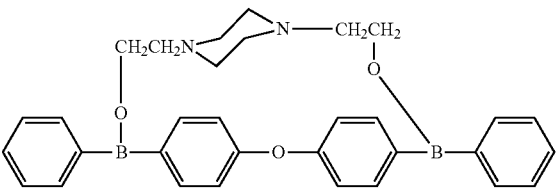

Example 197

4,4'-(phenyl piperazino-O,O-ethoxyboryl)benzylether (3001)

TG 99, x-Fold 1.02

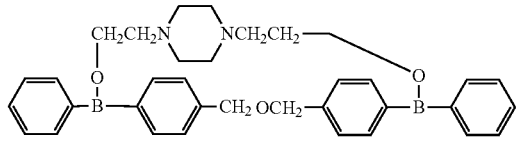

Example 198 bis(4,4'-(phenyldimethylaminoethoxyboryl)benzyl) ether (3003)

TG 28, x-Fold 0.8

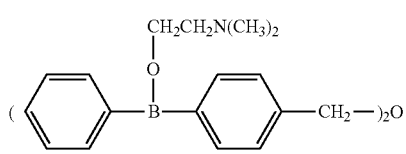

Example 199 bis(3,3'-(phenylbenzylaminoethoxyboryl)benzyl) ether (3017)

TG 3, x-Fold 0.90

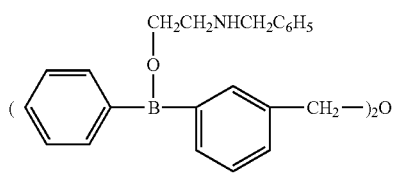

Example 200 di(3-chloro-2-methylphenyl)borinic acid (442)

TG 100, x-Fold 0.92

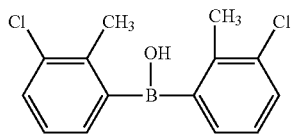

Example 201

4,4'-di((3-chloro-4-methylphenyl 2-hydroxyboryl) phenyl)ether (431)

TG 99, x-Fold 0.57

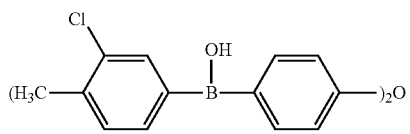

Example 202 phenyl naphthyl 2-pyridylmethylborinate (3041)

TG 91, x-Fold 0.94

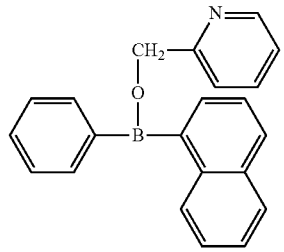 [SMILES: c1ccc(B(OCc2ccccn2)c2cccc3ccccc23)cc1]

Example 203 phenyl naphthyl dimethylaminoethylborinate (3044)

TG 97, x-Fold 0.97

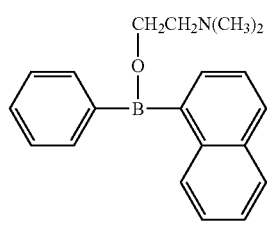

Example 204 phenyl naphthyl benzylaminoethylborinate (3045)

TG 61, x-Fold 0.79

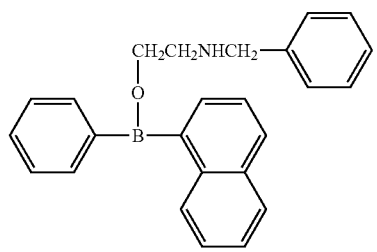

Example 205 bis(4,4'-(phenyl 2-amino-2-benzylethoxyboryl)benzyl)ether (3087)

TG 47, x-Fold 0.80

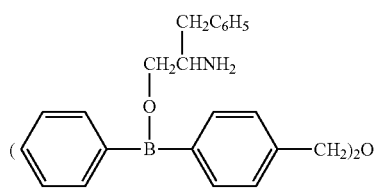

Example 206 bis(3,3'-(phenyldimethylaminoethoxyboryl)benzyl) ether (3107)

TG 34, x-Fold 1.14

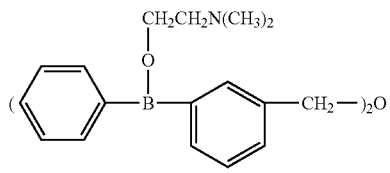

Example 207 di(3-chloro-4-methylphenyl)dimethylaminoethyl-borinate (3108)

TG 83, x-Fold 0.91

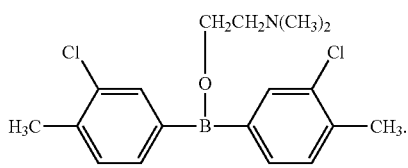

Example 208 di(3-chloro-4-methylphenyl)-2-benzyl-2-aminoethyl-borinate (3109)

TG −7, x-Fold 0.67

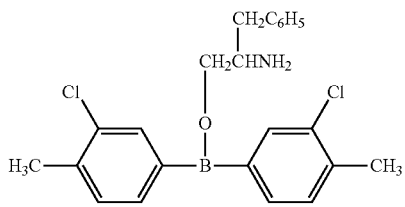

Example 209 di(3-chloro-4-methylphenyl)1-phenyl 2-aminoethylborinate (3111)

TG 1, x-Fold 0.98

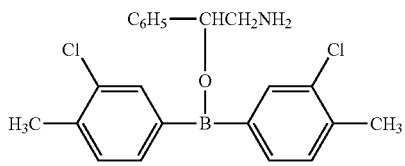

Example 210 di(3-chloro-4-methylphenyl)butylaminoethyl borinate (3112)

TG 27, x-Fold 0.98, SOC IC50 2 µM

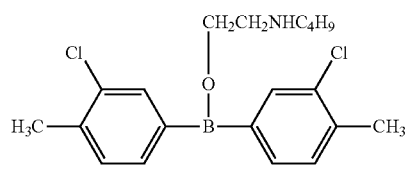

Example 211 di(3-chloro-4-methylphenyl)benzylaminoethyl borinate (3113)

TG 86, x-Fold 0.99, SOC IC50 1 µM

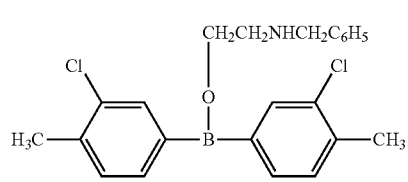

Example 212 diphenyl(R) 2-benzyl-2-aminoethyl borinate (3073)

TG 115, x-Fold 0.75

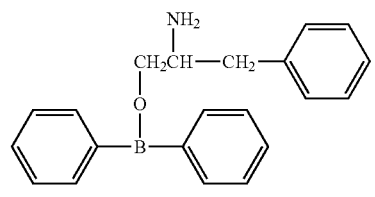

Example 213 diphenyl(S) 2-benzyl-2-aminoethyl borinate (3075)

TG 117, x-Fold 1.00

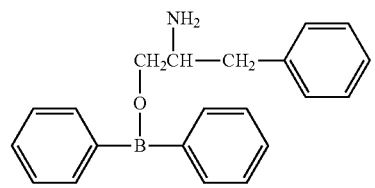

Example 214 di(3-chloro-4-methylphenyl) 1-phenylaminoethylborinate (3114)

TG −7, x-Fold 0.90, SOC IC50 2 μM

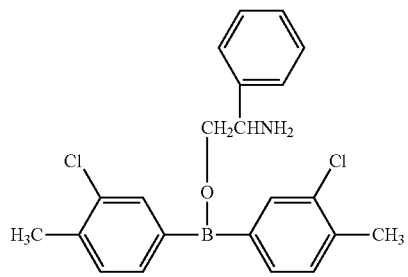

Example 215 di(3-chloro-4-methylphenyl)pyridylmethylborinate (3116)

TG 69, x-Fold 1.03, SOC IC50 2 μM

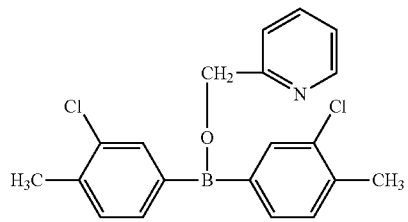

Example 216 di(3-chloro-4-methylphenyl)borinic acid anhydride (4139)

TG 17, x-Fold 1.03, SOC IC50 0.6 μM

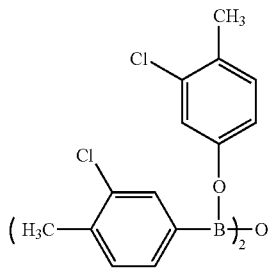

Example 217 diphenylborinic acid anhydride (4111)

TG 118, x-Fold 0.94

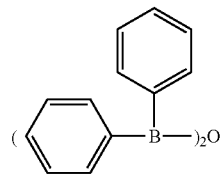

Example 218 diphenyl(picolinate-O,N)borane (4118)

TG 90, x-Fold 0.97

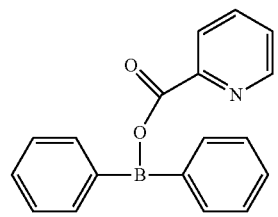 [SMILES: O=C(OB(c1ccccc1)c1ccccc1)c1ccccn1]

Example 219 diphenyl(2-aminophenyl carboxylate-O,N)borane (4119)

TG 91, x-Fold 0.88

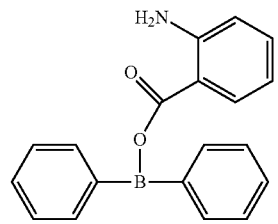 [SMILES: Nc1ccccc1C(=O)OB(c1ccccc1)c1ccccc1]

Example 220 di(3-chloro-4-methylphenyl) 2-aminophenylborinate (4121)

TG 26, x-Fold 0.50, SOC IC50 0.5 μM

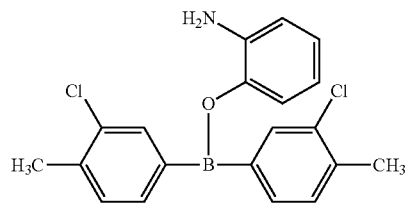

Example 221 di(3-chloro-4-methylphenyl)(2-pyridine carboxylate-O,N)borane (4123)

TG 73, x-Fold 0.94

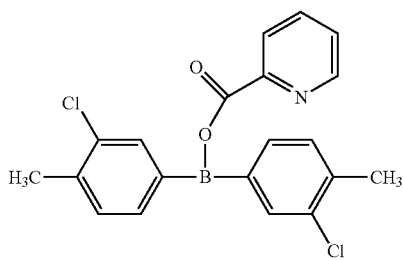

Example 222 poly(4,4'-diphenylether glutamine-O,N borane) (8003)

TG 122, x-Fold 0.86
Compound 7142 (Example 478) (53.3 mg) and glutamine (44 mg) were reacted in ethanol (2 ml) at 80° C. for 24 hr to give the title compound (14 mg).
NMR (DMSO) 1.95 (m, 2H), 2.0 (m, m, 2H), 2.23 (m, 2H), 3.35 (m, 4H), 7.4-8.1 (m, 8H)

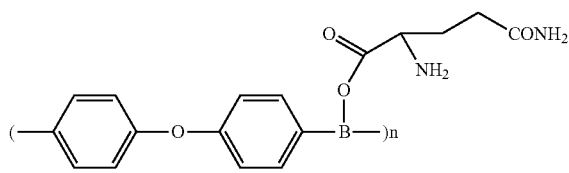

Example 223 poly(4,4'-diphenyl glutamine-O,N borane) (8006)

TG 116, x-Fold 1.02
Compound 4144 (Example 235) (41.3 mg) and glutamine (36 mg) were reacted in ethanol (2 ml) at 80° C. for 24 hr to give the title compound (75 mg).
NMR (DMSO) 1.95 (m, 2H), 2.05 (m, 2H), 2.25 (m, 2H), 3.40 (m, 4H), 6.8-7.7 (m, 8H)

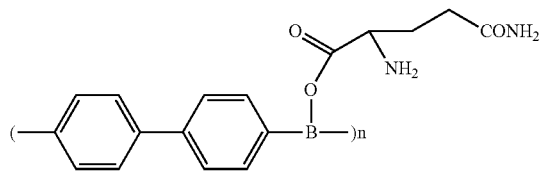

Example 224 diphenyl 1-(2-aminobenzyl) 1-phenylmethylborinate (4127)

TG 112, x-Fold 0.89

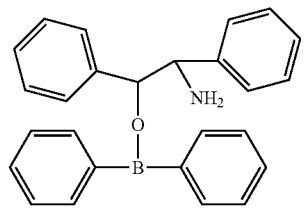 [SMILES: NC(c1ccccc1)C(OB(c1ccccc1)c1ccccc1)c1ccccc1]

Example 225 di(3-chloro-4-methylphenyl) 1-(2-aminobenzyl) 1-phenylmethylborinate (4128)

TG 109, x-Fold 1.03, SOC IC50 0.5 µM

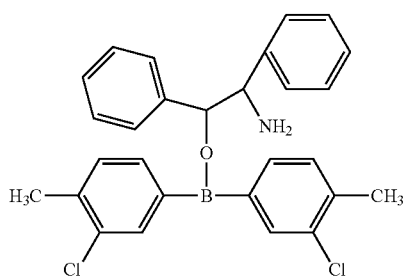

Example 226 diphenyl(2-aminohexanecarboxylate-O,N)borane (4129)

TG 97, x-Fold 0.94

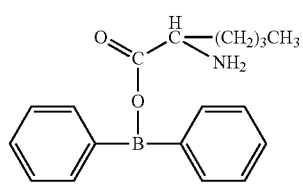

Example 227 di(3-chloro-4-methylphenyl)(norloysinate-O,N)borane (4130)

TG 110, x-Fold 0.99

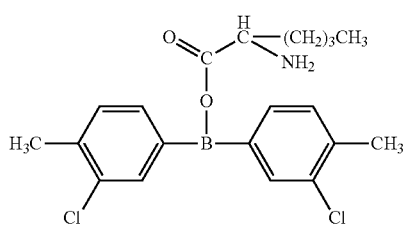

Example 228 diphenyl 2-aminobutylborinate (4131)

TG 99, x-Fold 0.98

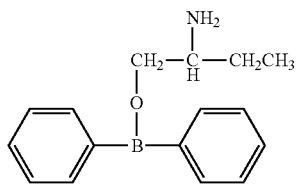 [SMILES: CCC(N)COB(c1ccccc1)c1ccccc1]

Example 229 di(3-chloro-4-methylphenyl) 2-aminobutylborinate (4132)

TG 40, x-Fold 1.09, SOC IC50 0.5 μM

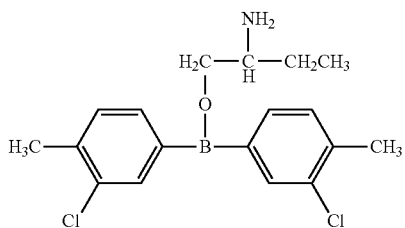

Example 230 di(trifluoromethylphenyl)borinic acid (4138)

TG 108, x-Fold 1.03

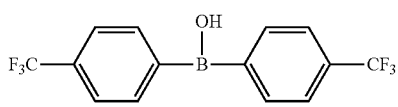

Example 231 di(3-fluoro-4-chlorophenyl)borinic acid (4140)

TG 94, x-Fold 1.01

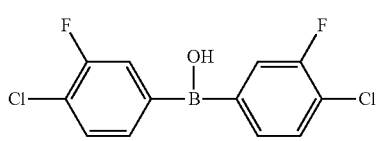 [SMILES: OB(c1ccc(Cl)c(F)c1)c1ccc(Cl)c(F)c1]

Example 232 di(trifluoromethylphenyl) 2-aminoethylborinate (4141)

TG 108, x-Fold 1.10

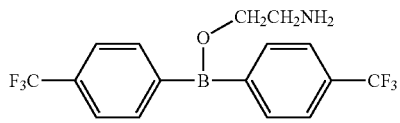

Example 233 di(trifluoromethylphenyl) 2-dimethylaminoethylborinate (4142)

TG 112, x-Fold 1.12

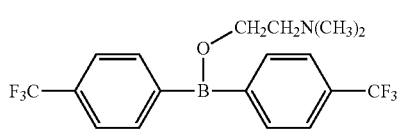

Example 234 di(4-chloro-3-fluoro-phenyl) 2-aminoethylborinate (4143)

TG 98, x-Fold 1.07, SOC IC50 0.5 μM

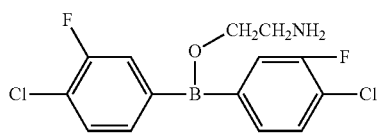

Example 235 di(4-chloro-3-fluorophenyl) 2,3-diamino-2-propyl-borinate (4144)

TG 80, x-Fold 1.03

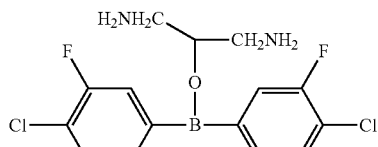

Example 236 di(4-chloro-3-fluorophenyl) 2-amino-2-methyl-propyl-borinate (4145)

TG 87, x-Fold 1.10

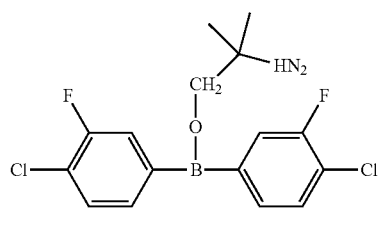

Example 237 di(4-chloro-3-fluorophenyl) 2-phenylaminoethyl borinate (4146)

TG 88, x-Fold 1.15

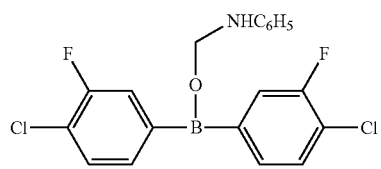

Example 238 di(4-chloro-3-fluorophenyl) 2-amino-3-hydroxybutyl borinate (4147)

TG 87, x-Fold 1.07

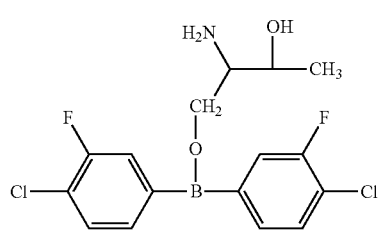 [SMILES: CC(O)C(N)COB(c1ccc(Cl)c(F)c1)c1ccc(Cl)c(F)c1]

Example 239 bis(diphenyl piperazino-O,O-ethoxyborane) (356)

TG 126, x-Fold 0.94

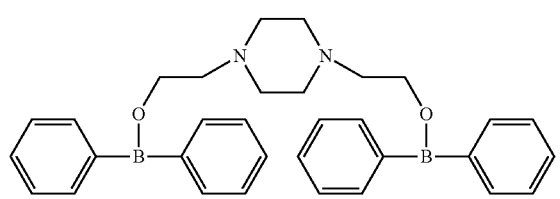 [SMILES: c1ccc(B(OCCN2CCN(CCOB(c3ccccc3)c3ccccc3)CC2)c2ccccc2)cc1]

Example 240

4-((2-aminoethoxy)phenylboryl)benzyl-4'-((2-aminoethoxy)phenylboryl)phenethylether (7117)

TG 25, x-Fold 0.99, SOC IC50 0.08 µM

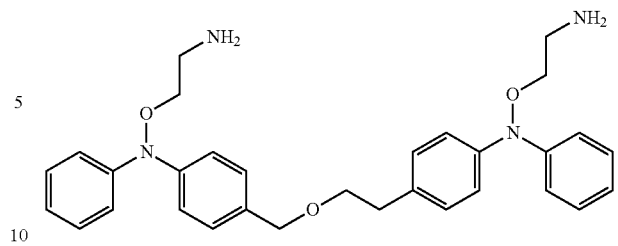

Example 241 di(3-chlorophenyl)borinic acid (244)

TG 67, x-Fold 1.10

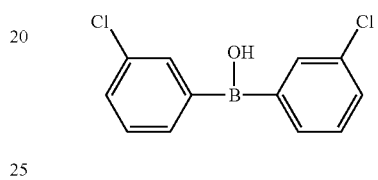

Example 242 di(5-chloro-2-methylphenyl) 2-piperidinomethylborinate (371)

TG 98, x-Fold 1.17

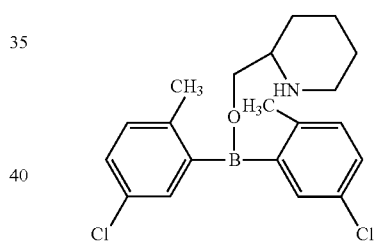

Example 243 di((5-chloro-2-methylphenyl)hydroxyborylphenyl) ether (436)

TG 106, x-Fold 0.73

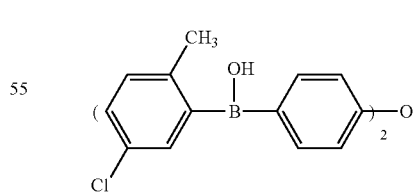

Example 244 di(5-chloro-2-methylphenyl) 2-aminoethylborinate (372)

TG 74, x-Fold 0.76, SOC IC50 1 µM

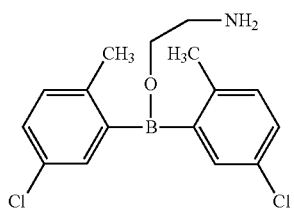 [SMILES: Cc1ccc(Cl)cc1B(OCCN)c1cc(Cl)ccc1C]

Example 245 diphenyl(ornithine-O,N)borane (921)

TG 94, x-Fold 0.91

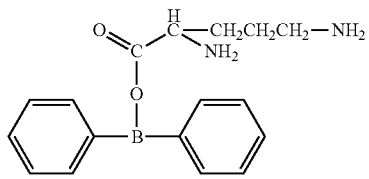

Example 246 di(5-chloro-2-methylphenyl)
2-butylaminoethylborinate (376)

TG 94, x-Fold 0.67

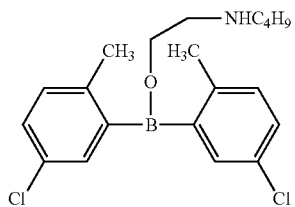

Example 247 di(3-chloro-4-methylphenyl)
2-piperidinomethylborinate (422)

TG 99, x-Fold 0.91, SOC IC50 0.7 μM

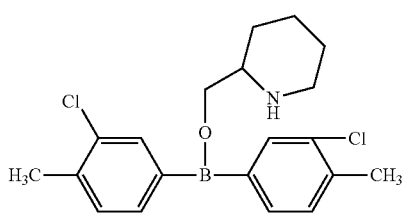

Example 248 di(3-chloro-4-methylphenyl)
2-piperidinoethylborinate (421)

TG 103, x-Fold 0.87

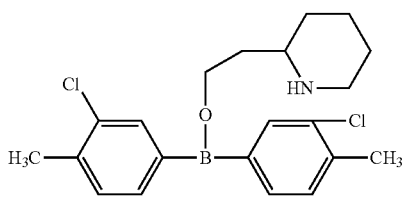

Example 249

4,4'-((2-aminoethoxy)(3-chloro-4-methylphenyl)
boryl)diphenylether (7118)

TG 25, x-Fold 0.74, SOC IC50 0.3 μM

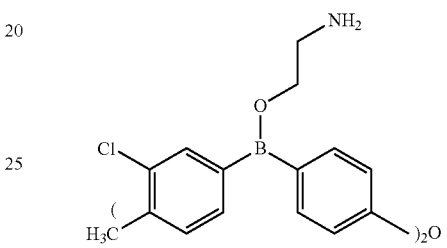

Example 250 bis(4,4'-(phenyldimethylaminoethoxyboryl)phenyl)
ether (1007)

TG 125, x-Fold 0.86

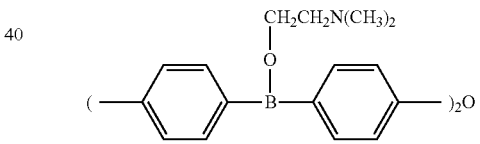

Example 251 bis(3-chloro-4-methylphenyl
hydroxyborylphenyl)ether (488)

TG 121, x-Fold 0.83

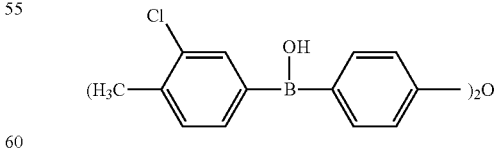

Example 252

1,4-bis(phenylhydroxyboryl)benzene (542)

TG 93, x-Fold 0.95, SOC IC50 0.5 μM

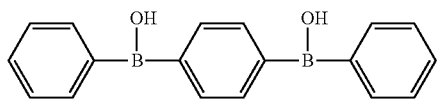

Example 253 di(2-thiophene)borinic acid (283)

TG 92, x-Fold 1.11

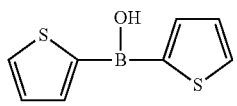 [SMILES: OB(c1cccs1)c1cccs1]

Example 254 diphenyl(glycinate-O,N)borane (827)

TG 101, x-Fold 0.95

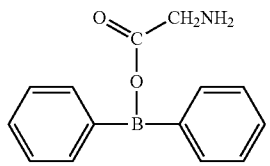

Example 255 diphenyl(serinate-O,N)borane (828)

TG 113, x-Fold 0.94, SOC IC50 0.5 μM

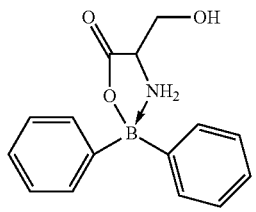 [SMILES: O=C1O[B-](c2ccccc2)(c2ccccc2)[NH2+]C1CO]

Example 256 diphenyl(glutaminate-O,N)borane (829)

TG 112, x-Fold 0.67, SOC IC50 1.5 μM

Diphenylborinic acid (78 mg) and sodium glutamate (73 mg) were stirred with heating in ethanol, water 1:1 mixture (1 mL) at 70° C. for 1 hr to give the title compound (120 mg).

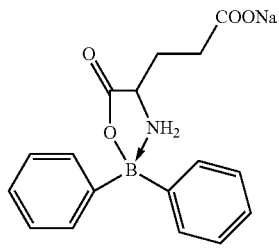

Example 257 diphenyl(asparaginate-O,N)borane (830)

TG 103, x-Fold 0.98

Diphenylborinic acid (50 mg) and aspartic acid (25 mg) were stirred with heating in ethanol, water 1:1 mixture (1 mL) at 70° C. for 1 hr to give the title compound (6 mg).

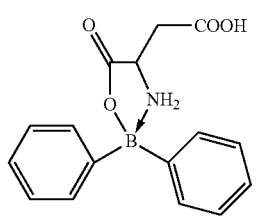 [SMILES: O=C(O)CC1[NH2+][B-](c2ccccc2)(c2ccccc2)OC1=O]

Example 258 diphenyl(alaninate-O,N)borane (833)

TG 110, SOC IC50 5 μM

Diphenylborinic acid (50 mg) and L-alanine (25 mg) were stirred with heating in ethanol, water 1:1 mixture (1 mL) at 70° C. for 1 hr to give the title compound (6 mg).

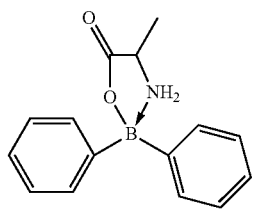 [SMILES: CC1[NH2+][B-](c2ccccc2)(c2ccccc2)OC1=O]

Example 259 diphenyl(phenylalaninate-O,N)borane (841)

TG 67, x-Fold 0.97, SOC IC50 2.5 μM

Diphenylborinic acid (47 mg) and phenylalanine (43 mg) were stirred with heating in ethanol, water 1:1 mixture (1 mL) at 70° C. for 16 hr to give the title compound (10 mg).

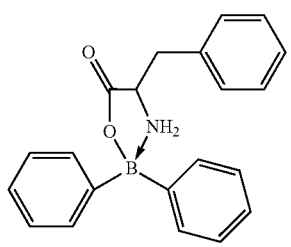 [SMILES: O=C1O[B-](c2ccccc2)(c2ccccc2)[NH2+]C1Cc1ccccc1]

Example 260 diphenyl(tryptophanate-O,N)borane (836)

TG 106, x-Fold 0.89

Diphenylborinic acid (46 mg) and tryptophan (52 mg) were stirred with heating in ethanol, water 1:1 mixture (1 mL) at 70° C. for 1 hr to give the title compound (15 mg).

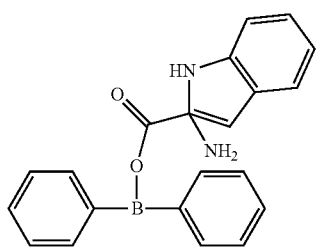

Example 261 diphenyl(leucinate-O,N)borane (837)

TG 109, x-Fold 0.89

Diphenylborinic acid (46 mg) and leucine (33 mg) were stirred with heating in ethanol, water 1:1 mixture (1 ml) at 70° C. for 1 hr to give the title compound (10 mg).

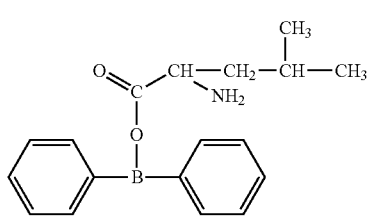 [SMILES: CC(C)CC(N)C(=O)OB(c1ccccc1)c1ccccc1]

Example 262 diphenyl(isoleucinate-O,N)borane (838)

TG 115, x-Fold 0.97

Diphenylborinic acid (52 mg) and isoleucine (37 mg) were stirred with heating in ethanol, water 1:1 mixture (1 mL) at 70° C. for 1 hr to give the title compound (10 mg).

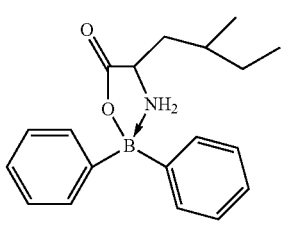 [SMILES: CCC(C)CC1[NH2+][B-](c2ccccc2)(c2ccccc2)OC1=O]

Example 263 diphenyl(2,4-diaminolactonate-O,N)borane (2045)

TG 146, x-Fold 0.89, SOC IC50 3 μM

Sodium tetraphenylborate (342 mg) and 2,4-diaminobutyric acid-hydrochloride (191 mg) were stirred with heating in water (7 ml) at 80° C. for 1 hr to give the title compound (160 mg).

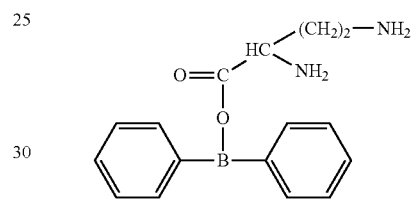

Example 264 diphenyl(tyrosinate-O,N)borane (842)

TG 109, x-Fold 1.00, SOC IC50 5 μM

Diphenylborinic acid (57 mg) and tyrosine (57 mg) were stirred with heating in ethanol, water 1:1 mixture (1 ml) at 70° C. for 1 hr to give the title compound (24 mg).

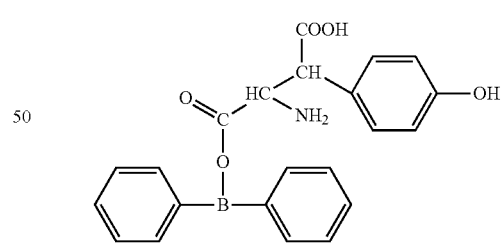

Example 265 diphenyl(threoninate-O,N)borane (851)

TG 112, x-Fold 0.94

Diphenylborinic acid (42 mg) and threonine (28 mg) were stirred with heating in ethanol, water 1:1 mixture (0.5 mL) at 70° C. for 1 hr to give the title compound (20 mg).

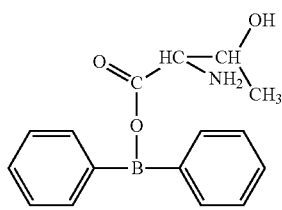 [SMILES: CC(O)C(N)C(=O)OB(c1ccccc1)c1ccccc1]

Example 266 diphenyl(cysteinate-O,N)borane (847)

TG 84, x-Fold 0.87, SOC IC50 3 μM

Diphenylborinic acid (31 mg) and cysteine (21 mg) were stirred with heating in ethanol, water 1:1 mixture (0.5 mL) at 70° C. for 1 hr to give the title compound (20 mg).

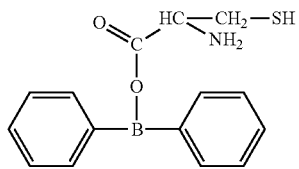 [SMILES: NC(CS)C(=O)OB(c1ccccc1)c1ccccc1]

Example 267 diphenyl(histidinate-O,N)borane (848)

TG 82, x-Fold 0.60, SOC IC50 3 μM

Diphenylborinic acid (32 mg) and histidine hydrochloride (36 mg) were stirred with heating in ethanol, water 1:1 mixture (0.5 mL) at 70° C. for 1 hr to give the title compound (6 mg).

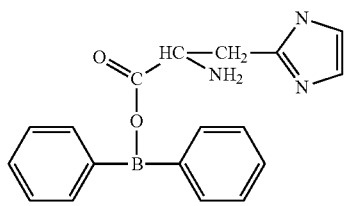 [SMILES: NC(Cc1ncc[nH]1)C(=O)OB(c1ccccc1)c1ccccc1]

Example 268 diphenyl(hydroxyprolinate-O,N)borane (852)

TG 103, x-Fold 0.96, SOC IC50 5 μM

Diphenylborinic acid (41 mg) and hydroxyproline (30 mg) were stirred with heating in ethanol, water 1:1 mixture (0.5 ml) at 70° C. for 1 hr to give the title compound (5 mg).

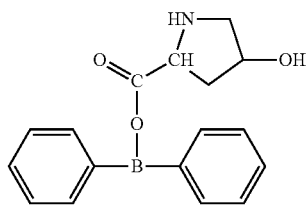 [SMILES: O=C(OB(c1ccccc1)c1ccccc1)C1CC(O)CN1]

Example 269 diphenyl(glutaminate-O,N)borane (879)

TG 95, x-Fold 1.01, SOC IC50 3 μM

Diphenyl 2-aminoethylborinate (112 mg) and glutamine (74 mg) were stirred with heating in a mixture of ethanol (0.4 mL), water (1.5 ml) and acetic acid (0.03 ml) at 100° C. for 10 min to give the title compound (21 mg).

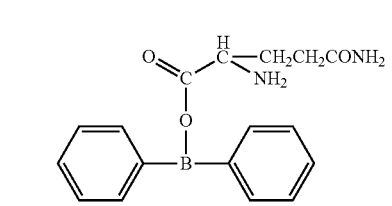

Example 270 diphenyl(asparaginate-O,N)borane (855)

TG 111, x-Fold 0.54, SOC IC50 0.7 μM

Diphenylborinic acid (182 mg) and asparagine (32 mg) were stirred with heating in ethanol, water 3:1 mixture (1 mL) at 70° C. for 1 hr to give the title compound (14 mg).

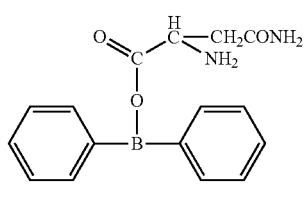

Example 271 diphenyl(lysinate-O,N)borane (906)

TG 109, x-Fold 1.07, SOC IC50 0.5 μM

Diphenylborinic acid (49 mg) and lysine hydrochloride (49 mg) were stirred with heating in a mixture of ethanol (1.5 ml) and water (0.5 mL) at 80° C. for 1 hr to give the title compound (44 mg).

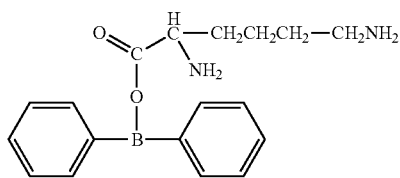

Example 272 diphenyl(2,3-diaminopropionate-O,N)borane (2043)

TG 83, x-Fold 0.09, SOC IC50 0.3 μM

Sodium tetraphenylborate (342 mg) and 2,4-diaminopropionic acid•hydrochloride (141 mg) were stirred with heating in water (5.5 ml) at 80° C. for 2 hr to give the title compound (203 mg).

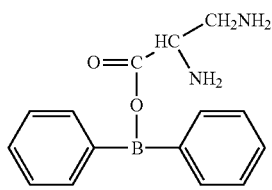

Example 273 bis(4,4'-(phenyl-glutamineboryl)phenyl)ether (1024)

TG 83, x-Fold 0.56, SOC IC50 0.25 μM

Bis(4,4'-(phenylhydroxyboryl)phenyl)ether (22 mg) and glutamine (19 mg) were heated in ethanol (2 mL) at 60° C. for 1 hr to give the title compound (8 mg).

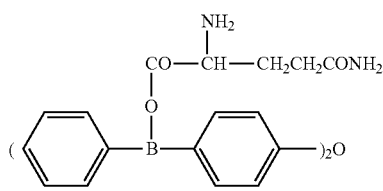

Example 274 bis(4,4'-(phenylasparagineboryl)phenyl)ether (1023)

TG 56, x-Fold 0.59, SOC IC50 0.3 μM

Bis(4,4'-(phenylhydroxyboryl)phenyl)ether (20 mg) and asparagine (14 mg) were stirred with heating in ethanol (3 mL) at 60° C. for 1 hr to give the title compound (7 mg).

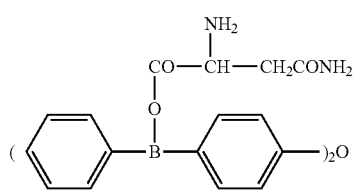

Example 275

(4-(phenyl-glutamic acid boryl)phenyl)-(4'-(hydroxymethylphenyl-glutamic acid boryl)phenyl)ether (1036)

TG 117, x-Fold 0.67, SOC IC50 0.3 μM 4-(Phenyl-hydroxyboryl)phenyl)-4'-(hydroxymethylphenyl-hydroxyboryl)phenyl)ether (27 mg) and sodium glutamate (22.3 mg) were reacted in ethanol (0.5 mL) to give the title compound (23 mg).

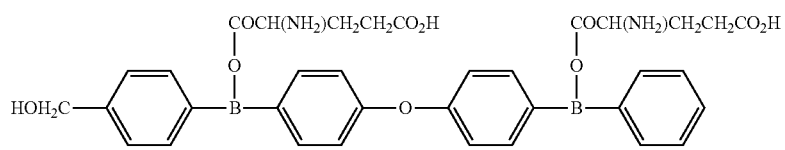

Example 276 diphenyl(glutaminate-O,N)borane (854)

TG 105, x-Fold 0.8

Diphenylborinic acid (39 mg) and glutamine (3.7 mg) were reacted in ethanol (0.6 mL) at 60° C. for 1 hr to give the title compound (10 mg).

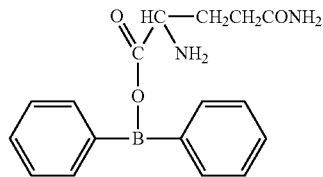

Example 277 diphenyl(prolinate-O,N)borane (843)

TG 105, x-Fold 0.98, SOC IC50 0.3 μM

Diphenylborinic acid (47 mg) and proline (2.7 mg) were reacted in ethanol (0.6 ml) at 60° C. for 1 hr to give the title compound (10 mg).

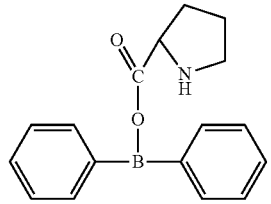 [SMILES: O=C(OB(c1ccccc1)c1ccccc1)C1CCCN1]

Example 278

(3-phenoxybenzyl)-(3'-(phenyl-2-aminoethoxyboryl)benzyl)ether (7119)

TG 2, x-Fold 1.08, SOC IC50 0.3 μM

Using 3-bromobenzyl-3'-phenoxybenzylether (1173 mg), bromobenzene (400 mg) and triisopropoxyborane (560 mg) as main starting materials, hydroxybromo compound was synthesized, and reacted with ethanolamine at room temperature to give the title compound (700 mg).

NMR (CDCl$_3$), 2.73 (m, 2H), 3.72 (t, 2H), 4.14 (m, 4H), 4.49 (s, 2H), 6.8-7.3 (m, 18H)

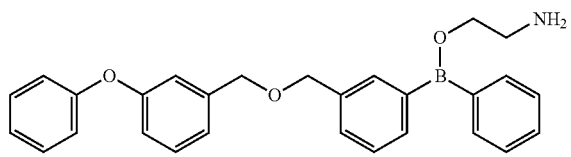 [SMILES: NCCOB(c1ccccc1)c1cccc(COCc2cccc(Oc3ccccc3)c2)c1]

Example 279 diphenyl(2-piperazinecarboxy)borane (894)

TG 103, x-Fold 0.98

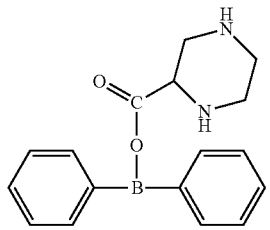 [SMILES: O=C(OB(c1ccccc1)c1ccccc1)C1CNCCN1]

Example 280 diphenyl(2,4-diaminolacetic acid)borane (897)

TG 98, x-Fold 0.88

Aminoethyldiphenylborinate (112 mg) and 2,4-diaminobutyric acid•hydrochloride (35 mg) were reacted in ethanol (0.5 ml) and acetic acid (30 mg) to give the title compound (139 mg).

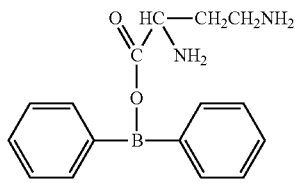

Example 281 di(3-chloro-4-methylphenyl)-(picolinate-O,N)borane (4123)

TG 77, x-Fold 0.94

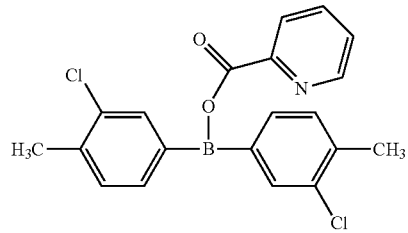

Example 282 di(3-chloro-4-methylphenyl)(asparaginate-O,N)borane (4103)

TG 112, x-Fold 0.95, SOC IC50 0.3 μM

Di(3-chloro-4-methyl)phenylborinic acid (82 mg) and asparagine (81 mg) were reacted in ethanol (0.6 mL) to give the title compound (37 mg).

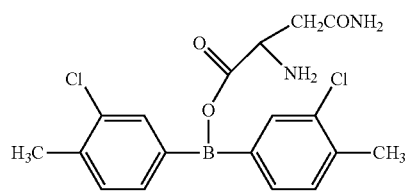

Example 283 di(3-chloro-4-methylphenyl) 2-aminophenylthioborane (4125)

TG 12, x-Fold 0.83, SOC IC50 0.9 μM

Di(3-chloro-4-methyl)phenylborinic acid (47 mg) and dimethylaminoethanethiol (17 mg) were stirred in ether (1 ml) overnight, ether (2 ml) was added to give the title compound (17 mg) as a white precipitate.

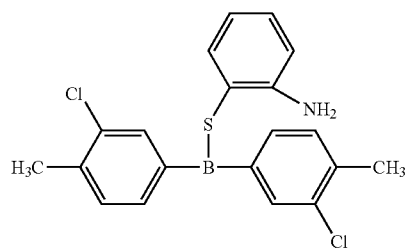

Example 284 di(4-trifluoromethylphenyl) (picolinate-O,N)borane (5003)

TG 89, x-Fold 1.03

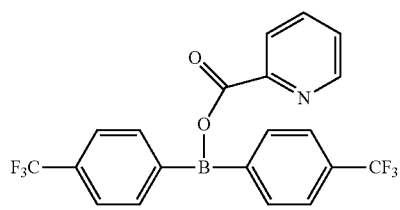 [SMILES: O=C(OB(c1ccc(C(F)(F)F)cc1)c1ccc(C(F)(F)F)cc1)c1ccccn1]

Example 285 di(4-trifluoromethylphenyl) 2-aminoethylthioborane (5004)

TG 51, x-Fold 0.99, SOC IC50 2 μM

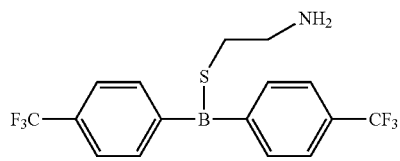 [SMILES: NCCSB(c1ccc(C(F)(F)F)cc1)c1ccc(C(F)(F)F)cc1]

Example 286 di(3-chloro-4-methylphenyl)(2,6-diaminopimelinate-O,N)borane (5012)

TG 104, x-Fold 0.93

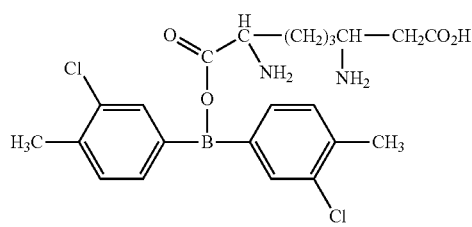

Example 287 di(3-chloro-4-methylphenyl)(citrullinate-O,N)borane (5013)

TG 146, x-Fold 1.00

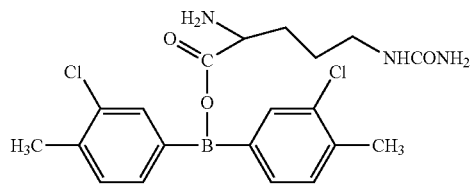

Example 288 di(3-chloro-4-methylphenyl)(glycylglutaminate-O,N)borane (5014)

TG 106, x-Fold 1.02

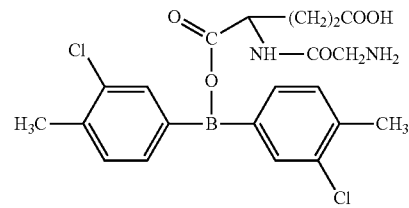

Example 289 di(4-trifluoromethylphenyl)(1,3-propylenediaminediacetate-O,N)borane (5015)

TG 94, x-Fold 1.08, SOC IC50 0.3 μM

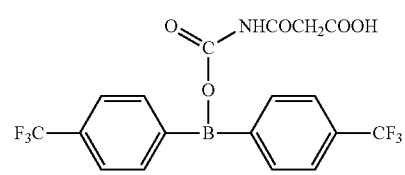

Example 290 di(4-trifluoromethylphenyl)(glycylglycinate-O,N)borane (5018)

TG 113, x-Fold 1.05

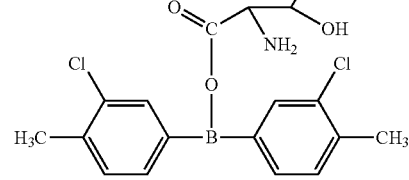

Example 291 di(3-chloro-4-methylphenyl)(allothreoninate-O,N)borane (5019)

TG 50, x-Fold 1.02, SOC IC50 0.5 μM

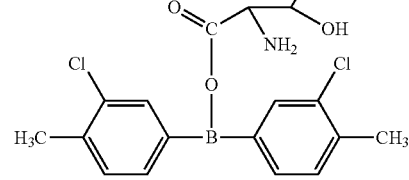

Example 292 di(3-chloro-4-methylphenyl)(norloysinate-O,N)borane (5020)

TG 146, x-Fold 1.00, SOC IC50 1 μM

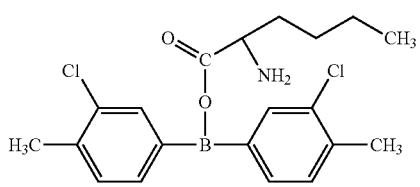 [SMILES: CCCCC(N)C(=O)OB(c1ccc(C)c(Cl)c1)c1ccc(C)c(Cl)c1]

Example 293 di(3-chloro-4-methylphenyl)(2,4-diaminobutyrate-O,N)borane (5021)

TG 116, x-Fold 0.91

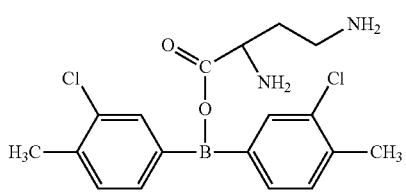

Example 294 diphenyl dimethylaminoethylthioborane (4106)

TG 114, x-Fold 0.96, SOC IC50 2 μM

1N Sodium hydroxide (0.28 mL) was added to dimethylaminoethylthiol hydrochloride (40 mg) and the mixture was extracted with ether. Diphenylborinic acid (44 mg) was added and the mixture was dried to solidness, ethanol (1 mL) was added and the mixture was stirred for 15 hr, dried to solidness and washed with ether to give the title compound (2 mg).

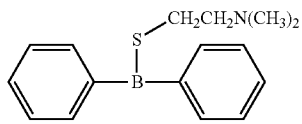

Example 295 di(3-chloro-4-methylphenyl)dimethylaminoethylthioborane (4107)

TG 107, x-Fold 0.92, SOC IC50 0.8 μM

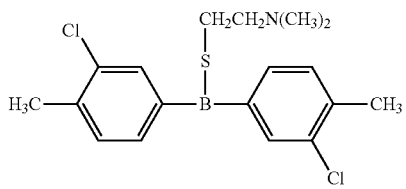

Example 296

(4-(2-thiophenehydroxyboryl)phenoxyethyl)(4'-(2-thiophenehydroxyboryl)benzyl)ether (795)

TG 97, x-Fold 0.74

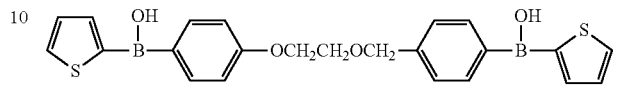

Example 297

1,2-di(phenylhydroxyboryl)benzene (806)

TG 89, x-Fold 0.69

1,2-Dibromobenzene (236 mg) was reacted with 1N sec-BuLi (2.1 mL) at −98° C. (SOLUTION A). Bromobenzene was reacted with sec-BuLi and triisopropoxyborane (460 μL) (SOLUTION B). SOLUTION A and SOLUTION B were reacted to give the title compound (95 mg) as a candy-like substance.

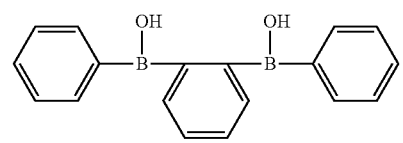 [SMILES: OB(c1ccccc1)c1ccccc1B(O)c1ccccc1]

Example 298

1,2-di(phenylaminoethoxyboryl)benzene (810)

TG 101, x-Fold 1.01

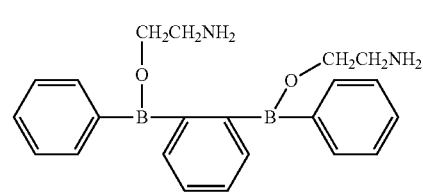

Example 299 poly(2,5-dimethylphenyl asparagine-O,N borane) (8007)

TG 118, x-Fold 1.13

Poly(2,5-dimethylphenyl hydroxyborane) (34 mg) and glutamine (40 mg) were stirred in ethanol at 80° C. for 12 hr to give the title compound (7 mg).

NMR (DMSO) 1.95 (m, 2H), 2.0 (m, 2H), 2.1 (m, 6H), 3.2 (m, 4H), 7.2-8.0 (m, 2H)

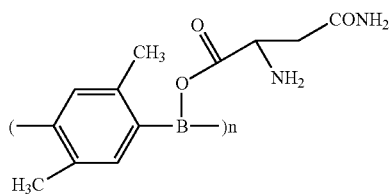

Example 300 poly(phenylene 2-aminoethylaminoethoxy borane) (1085)

TG 95, x-Fold 0.80, SOC IC50 5 μM

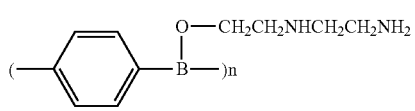

Example 301 poly(phenylene 2-pyridylmethoxy borane) (1083)

TG 108, x-Fold 0.84

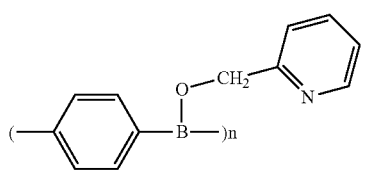

Example 302 poly(1,4-phenylenehydroxyboryl-1,3-phenyleneborinic acid) (6062)

TG 103, x-Fold 0.94

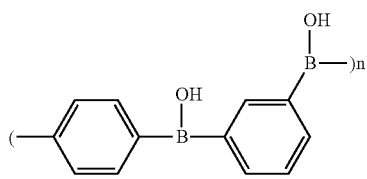

Example 303 poly(1,4-phenylene aminoethoxyboryl-1,3-phenyleneaminoethoxyborane) (6082)

TG 103, x-Fold 0.91

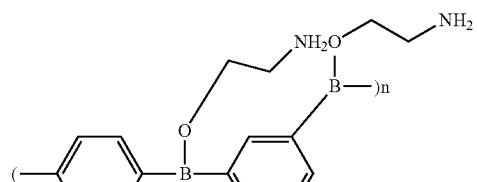

Example 304

2,8-di(3-thiophenylglutamine-O,N boryl)dibenzothiophene (8020)

TG 47, x-Fold 0.90

Compound 8013 (Example 406) (24 mg) and glutamine (19 mg) were stirred in ethanol at 80° C. for 12 hr to give the title compound (16 mg).

NMR (DMSO) 1.90 (m, 2H), 1.95 (m, 2H), 2.10 (m, 4H), 2.30 (m, 4H), 7.0-8.0 (m, 12H)

Example 305

4,4'-di(cyano-phenyl)borinic acid (6095)

TG 94, x-Fold 0.98

Example 306

3,3'-di(cyano-phenyl)borinic acid (6096)

TG 90, x-Fold 0.98

Example 307 diphenyl(citrullinate-O,N)borane (7021)

TG 54, x-Fold 1.06, SOC IC50 0.5 μM

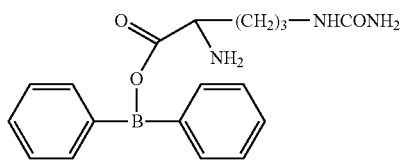

Example 308 diphenyl(ornithinate-O,N)borane (7020)

TG 27, x-Fold 1.05, SOC IC50 0.5 μM

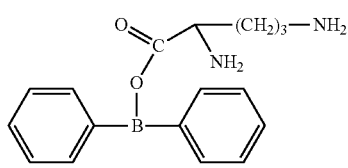

Example 309 poly(1,2-phenylene-hydroxyborane) (7047)

TG 109, x-Fold 0.93

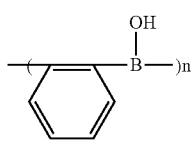

Example 310 poly(2,5-dimethyl-1,4-phenylene-hydroxyborane) (7051)

TG 114, x-Fold 1.02

2,5-Dimethyl-1,5-dibromobenzene (263 mg) was dissolved in ether (10 mL) at −78° C., sec-butyllithium (2 ml) was added and the mixture was stirred for 1 hr. Triisopropoxyborane (220 μL) was added and the mixture was gradually warmed to room temperature and treated with hydrochloric acid to give the title compound (74.5 mg).

NMR (CDCl$_3$) 2.38 (s, 6H), 7.4 (m, 2H)

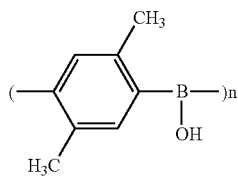

Example 311 poly(2-methyl-1,3-phenylene-hydroxyborane) (7052)

TG 111, x-Fold 1.00

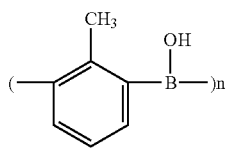

Example 312 poly(2,8-dibenzothiophenylene-hydroxyborane) (7053)

TG 98, x-Fold 1.00

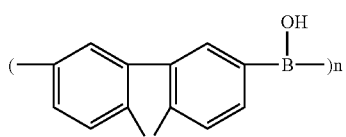

Example 313 poly(2,2'-biphenylene-hydroxyborane) (7056)

TG 107, x-Fold 0.98

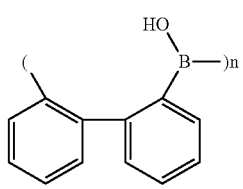

Example 314 poly(1,4-naphthalene-hydroxyborane) (7057)

TG 104, x-Fold 0.93

4,4'-parabrombenzylether (90 mg) was dissolved in ether (4 mL), and 1N sec-butyllithium (0.75 mL) cooled to −78° C. was added and the mixture was stirred for 60 min (SOLUTION A). 4,4'-parabromophenylether (90 mg) was dissolved in ether (4 mL) and the mixture was cooled to −78° C. 1N sec-Butyllithium (0.7 mL) was added and the mixture was stirred for 30 min. Triisopropoxyborane (188 mg) was added and the mixture was stirred to −65° C. (SOLUTION B). SOLUTION A and SOLUTION B were mixed and the mixture was gradually warmed and stirred at room temperature for 15 hr. The mixture was acidified with 1N hydrochloric acid, and the organic layer was washed with water, dried, and concentrated to give the title compound (154 mg).

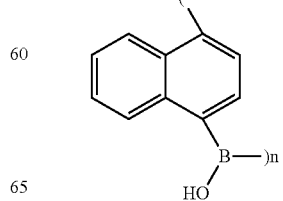

Example 315 poly(9,10-anthracene-hydroxyborane) (7058)

TG 102, x-Fold 0.92

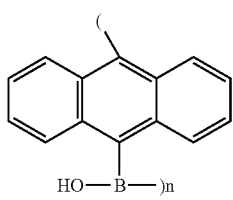

Example 316 poly(3,6-carbazole-hydroxyborane) (7059)

TG 72, x-Fold 1.11

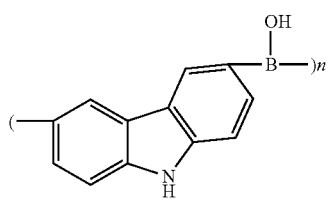

Example 317 poly(5-methyl-1,3-phenylene-hydroxyborane) (7063)

TG 107, x-Fold 0.99

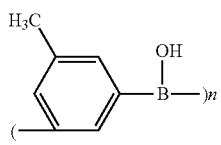

Example 318 poly(5,5'-bithiophene-hydroxyborane) (7064)

TG 81, x-Fold 1.02

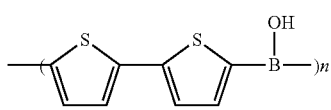

Example 319 poly(2,2'-binaphthyl-hydroxyborane) (7065)

TG 108, x-Fold 1.04

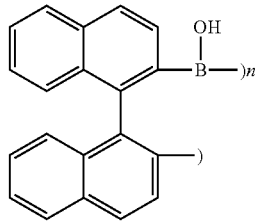

Example 320 poly(4,4'-biphenylene aminoethoxyborane) (1128)

TG 100, x-Fold 0.78, SOC IC50 5 μM

Poly(4,4'-biphenylborinic acid) (38 mg) was dissolved in ether (0.5 mL), ethanolamine (13 mg) was added and the mixture was stirred for 10 hr. Ether (1 mL) was added to give the title compound (12 mg) as a precipitate.

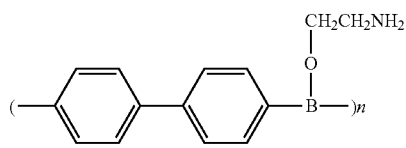

Example 321 poly(4,4'-biphenylene N-hydroxyethylaminoethoxyborane) (1129)

TG 116, x-Fold 0.78

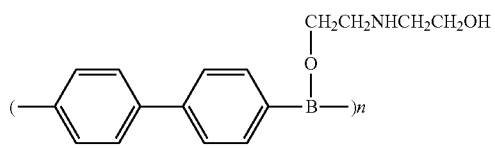

Example 322 bis(4,4'-(3-chloro-4-methylphenylhydroxyboryl)benzyl)ether (612)

TG 98, x-Fold 0.32, SOC IC50 0.2 μM

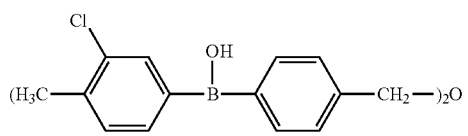

Example 323 poly(4-phenylborinic acid) (502)

TG 111, x-Fold 0.82

Paradibromobenzene (148 mg) was dissolved in ether (10 ml), sec-butyllithium (1.5 mL) was added at −95° C. and the mixture was stirred for 30 min. Triisoproxyborane (276 μL) was added at −78° C. and the mixture was stirred for 1 hr (SOLUTION A). Paradibromobenzene (148 mg) was dissolved in ether (10 mL), sec-butyllithium (1.5 ml) was added at −95° C. and the mixture was stirred for 30 min (SOLUTION B). SOLUTION A and SOLUTION B were mixed at −78° C., and the mixture was gradually warmed to room temperature and stirred overnight. Hydrochloric acid solution was added, and the mixture was applied to column chromatography to give the title compound (110 mg).

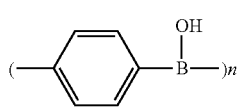

Example 324 naphthaleneboronic acid (7126)

x-Fold 0.76

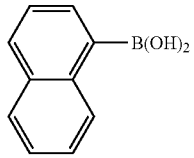 [SMILES: OB(O)c1cccc2ccccc12]

Example 325 bis(4-(4-trifluoromethylphenylhydroxyboryl)phenyl) ether (2054)

TG 92, x-Fold 0.99, SOC IC50 4 μM

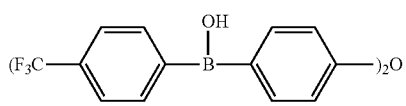

Example 326 poly(2,5-dimethylphenyl aminopropoxyborane) (8009)

TG 103, x-Fold 1.09

Compound 7051 (Example 310) (34 mg) and ethanolamine (17 mg) were reacted at room temperature for 4 hr to give the title compound (8.7 mg).

NMR (CDCl$_3$) 2.34 (s, 6H), 2.62 (m, 2H), 2.95 (m, 2H), 3.65 (m, 2H), 7.2-7.8 (m, 2H)

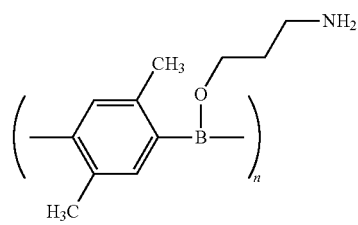

Example 327 poly(2,5-dimethylphenyl aminopropylthioborane) (8010)

TG 14, x-Fold 1.07

Compound 7051 (Example 310) (32 mg) and aminoethanethiol (20 mg) were reacted at room temperature for 4 hr to give the title compound (28 mg).

NMR (CDCl$_3$) 1.8-2.0 (br, 2H), 2.31 (m, 6H), 2.76 (m, 2H), 3.01 (m, 2H)

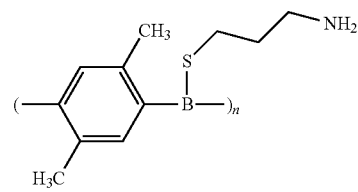

Example 328 bis(3-(4-methoxyphenylhydroxyboryl)benzyl)ether (2072)

TG 100, x-Fold 1.04

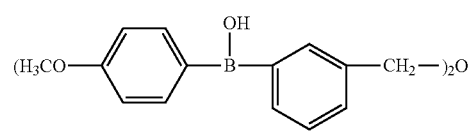

Example 329

(3-(phenylhydroxyboryl)benzyl)(4-(phenylhydroxyboryl)benzyl)ether (672)

TG 81, SOC IC50 0.2 μM

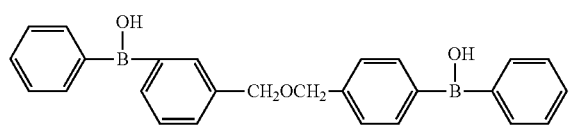

Example 330

(2-(phenylhydroxyboryl)benzyl)(3-(phenylhydroxyboryl)benzyl)ether (655)

TG 89, x-Fold 0.90

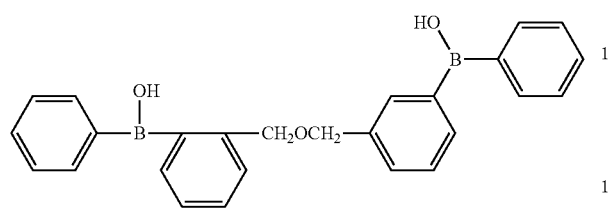

Example 331

(2-(phenylhydroxyboryl)benzyl)(4-(phenylhydroxyboryl)benzyl)ether (682)

TG 101, x-Fold 0.98, SOC IC50 1 μM

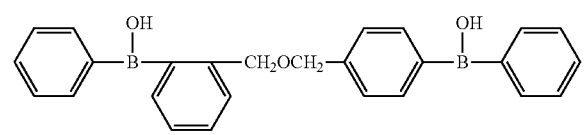

Example 332

(3-(phenylaminoethoxyboryl)benzyl)(4-(phenylaminoethoxyboryl)benzyl)ether (674)

TG 21, x-Fold 0.98, SOC IC50 0.2 μM

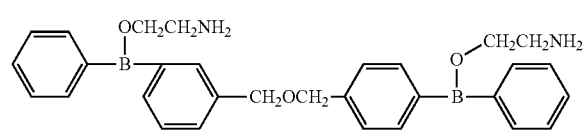

Example 333 bis(3-(3-chloro-4-methylphenylhydroxyboryl)benzyl)ether (701)

TG 107, x-Fold 1.09

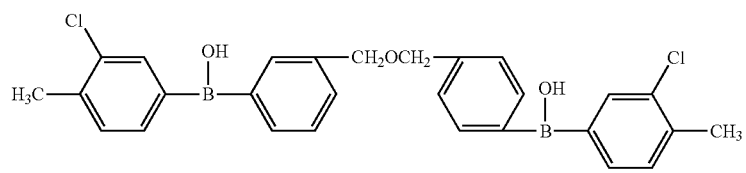

Example 334

(2-(phenylaminoethoxyboryl)benzyl)(3-(phenylaminoethoxyboryl)benzyl)ether (687)

TG 21, x-Fold 1.02, SOC IC50 0.3 μM

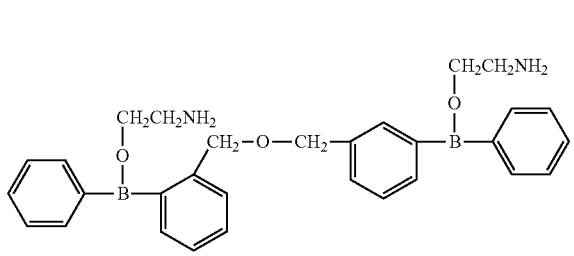

Example 335

(2-(phenylaminoethoxyboryl)benzyl) (4-(phenylaminoethoxyboryl)benzyl)ether (686)

TG 91, x-Fold 1.02

Example 336 bis(3-(4-fluorophenylhydroxyboryl)benzyl)ether (688)

TG 101, x-Fold 1.02

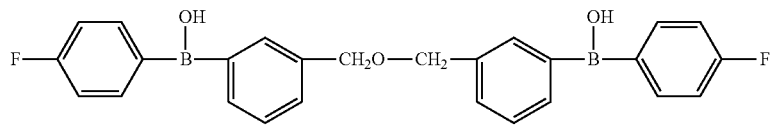

Example 337 bis(3-(4-fluorophenylaminoethoxyboryl)benzyl)ether (689)

TG 102, x-Fold 0.98

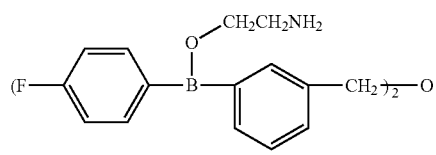

Example 338 bis(4-(4-chloro-3-methyl-phenyl)hydroxyborylbenzyl)ether (693)

TG 110, x-Fold 0.83

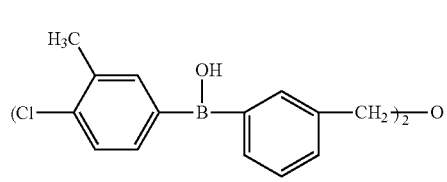

Example 339 bis(4-(4-chloro-3-methyl-phenylaminoethoxyborylbenzyl)ether (696)

TG 115, x-Fold 0.91

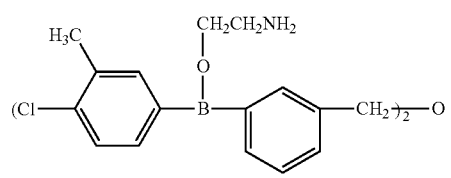

Example 340 bis(3-(3',4'-methylenedioxy-phenylhydroxyboryl)benzyl)ether (700)

TG 63, x-Fold 1.01

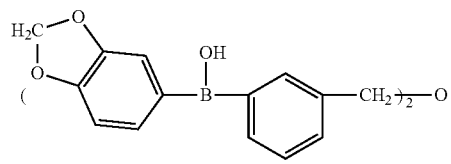

Example 341

(3-(3-chloro-4-methylphenylhydroxyboryl)benzyl) (4-(3-chloro-4-methylphenylhydroxyboryl)benzyl) ether (701)

TG 107, x-Fold 1.04

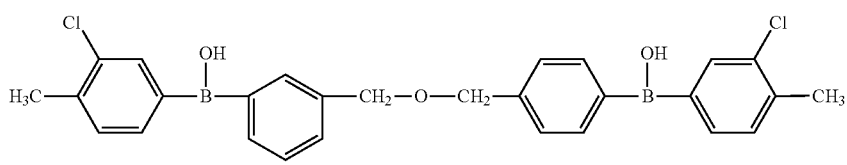

Example 342

(3-(3',4',5'-trifluorophenylhydroxyboryl)benzyl)(4-(3',4',5'-trifluorophenylhydroxyboryl)benzyl)ether (702)

TG 114, x-Fold 1.02

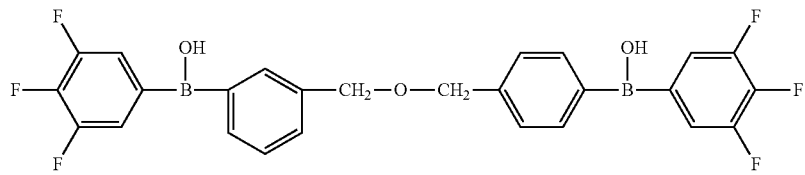 [SMILES: OB(c1ccc(COCc2cccc(B(O)c3cc(F)c(F)c(F)c3)c2)cc1)c1cc(F)c(F)c(F)c1]

Example 343 bis(3-(4-methoxyphenylaminoethoxyboryl)benzyl)ether (704)

TG 55, x-Fold 1.02

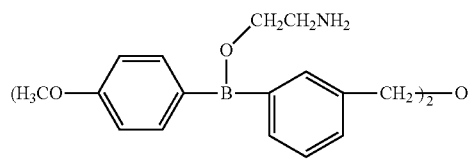

Example 344

(3-(4-chloro-3-methylphenylhydroxyboryl)benzyl)(2-(4-chloro-3-methylphenylhydroxyboryl)benzyl)ether (705)

TG 91, x-Fold 0.93

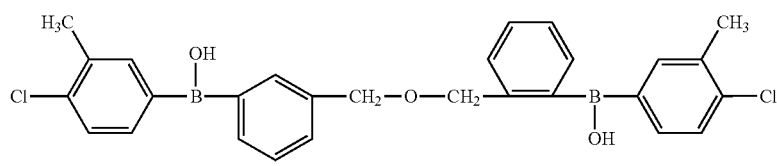 [SMILES: Cc1cc(B(O)c2cccc(COCc3ccccc3B(O)c3ccc(Cl)c(C)c3)c2)ccc1Cl]

Example 345 bis(3-(4-cyanophenylhydroxyboryl)benzyl)ether (706)

TG 95, x-Fold 0.92

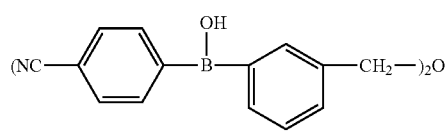

Example 346 bis(3-(2'-thiophenylhydroxyboryl)benzyl)ether (707)

TG 101, x-Fold 0.81

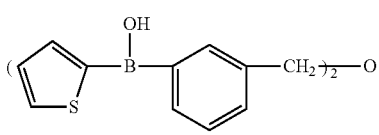

Example 347 bis(3-(1'-naphthylhydroxyboryl)benzyl)ether (708)

TG 104, x-Fold 0.90

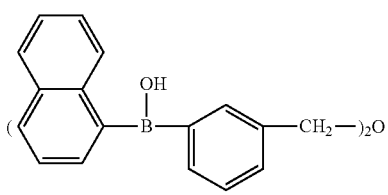

Example 349 bis(4-(2-methoxy-5-fluorophenylhydroxyboryl)benzyl)ether (710)

TG 104, x-Fold 0.80

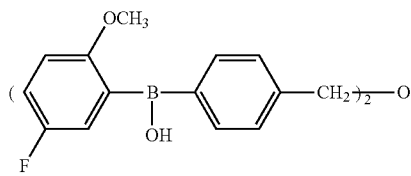

Example 350 bis(4-(2-methoxy-5-fluorophenylaminoethoxyboryl)
benzyl)ether (717)

TG 105, x-Fold 0.92

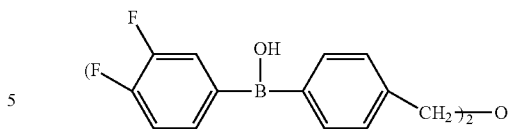

Example 353 bis(4-(3,4-difluorophenylaminoethoxyboryl)benzyl)
ether (712)

TG 115, x-Fold 0.85

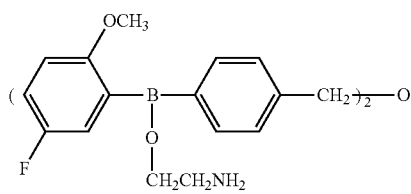

Example 351

(3-(4-chloro-3-methyl-phenylaminoethoxyboryl)
benzyl)(2-(4-chloro-3-methyl-phenylaminoethoxy-
boryl)benzyl)ether (711)

TG 103, x-Fold 1.00

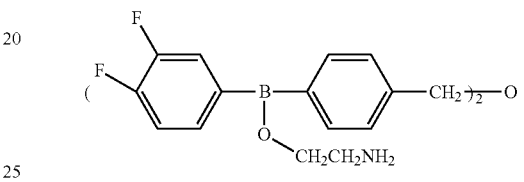

Example 354

(3-(3',4',5'-trifluorophenylaminoethoxyboryl)benzyl)
(4-(3',4',5'-trifluorophenylaminoethoxyboryl)benzyl)
ether (719)

TG 113, x-Fold 1.09

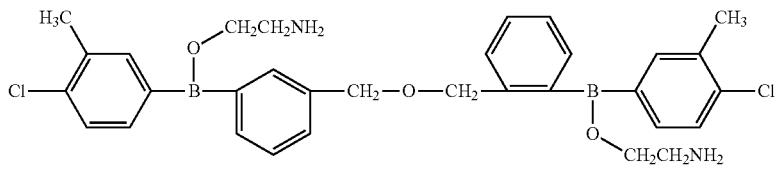

Example 352 bis(4-(3,4-difluorophenylhydroxyboryl)benzyl)ether
(718)

TG 97, x-Fold 1.02

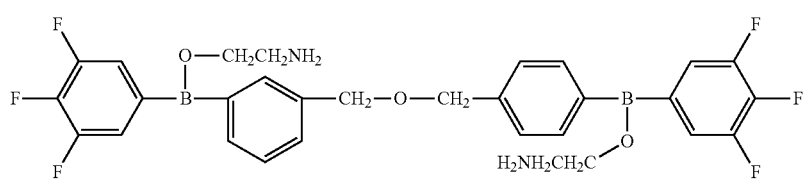

Example 355

5,5'-(phenylhydroxyboryl)-2,2'-dithiophene (731)

TG 91, x-Fold 1.09

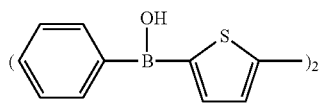

Example 356

5,5'-(phenylaminoethoxyboryl)-2,2'-dithiophene (735)

TG 51, x-Fold 1.06

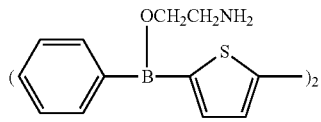

Example 357

3,5-di(phenylaminoethoxyboryl)toluene (736)

TG 89, x-Fold 1.03

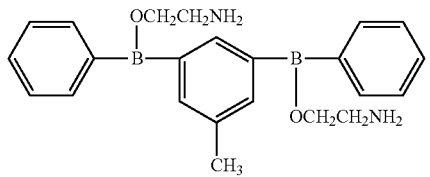

Example 358

2,5-di(phenylhydroxyboryl)toluene (739)

TG 112, x-Fold 0.91

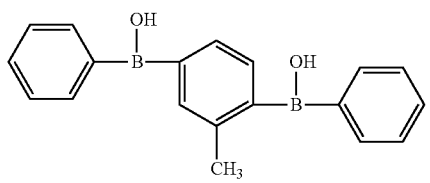 [SMILES: Cc1cc(B(O)c2ccccc2)ccc1B(O)c1ccccc1]

Example 359

2,2'-di(phenylhydroxyboryl)-1,1'-binaphthyl (744)

TG 139, x-Fold 0.96

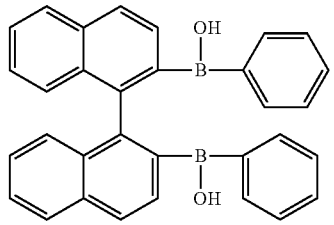 [SMILES: OB(c1ccccc1)c1ccc2ccccc2c1-c1c(B(O)c2ccccc2)ccc2ccccc12]

Example 360

2,2'-di(phenylaminoethoxyboryl)-1,1'-binaphthyl (745)

TG 88, x-Fold 1.05

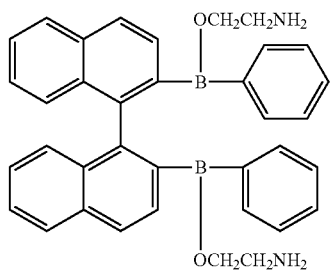

Example 361 bis(4-(4-methylphenylhydroxyboryl)benzyl)ether (709)

TG 100, x-Fold 0.88, SOC IC50 >20 μM

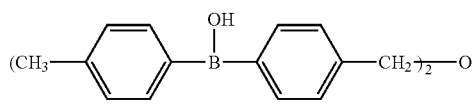

Example 362 bis(4-(4-methylphenylaminoethoxyboryl)benzyl)ether (729)

TG 108, x-Fold 1.08

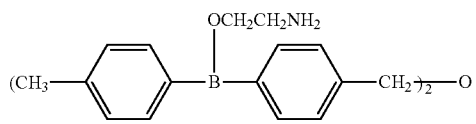

Example 363

4,4'-(4-methylphenylhydroxyboryl)diphenyl (752)

TG 97, x-Fold 0.92

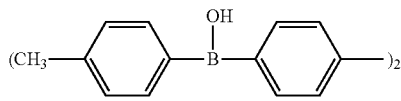

Example 364

4,4'-(4-methylphenylaminoethoxyboryl)diphenyl (754)

TG 44, x-Fold 0.82

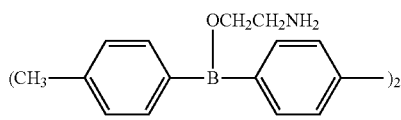

Example 365

4,4'-(4-methylphenylhydroxyboryl)diphenylether (753)

TG 118, x-Fold 0.91

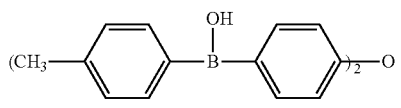

Example 366 poly(2,5-dimethylphenyl 2-pyridylmethoxyborane) (8011)

TG 108, x-Fold 0.93

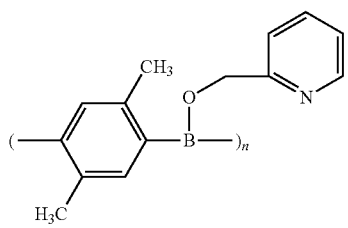

Compound 7051 (Example 310) (7.2 mg) and 2-pyridylmethanol (6 mg) were reacted in ethanol at room temperature for 4 hr to give the title compound (4 mg).
NMR (CDCl$_3$) 3.45 (m, 6H), 4.72 (m, 2H), 7.2-8.5 (m, 6H)

Example 367

4,4'-bis(3-chloro-4-methyl-phenylhydroxyboryl)diphenylether (513)

TG 113, x-Fold 0.73

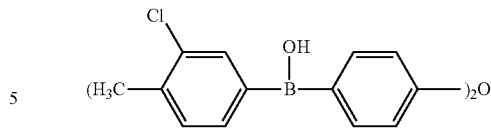

Example 368

(2-(phenylhydroxyboryl)phenethyl)((2-phenylhydroxyboryl)benzyl)ether (6055)

TG 52, x-Fold 1.03

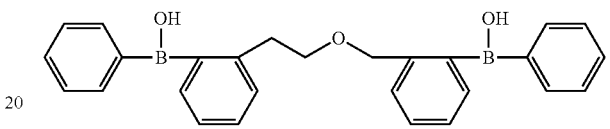

Example 369

(2-(phenylaminoethoxyboryl)phenethyl)((2-phenylaminoethoxyboryl)benzyl)ether (7133)

TG 105, x-Fold 1.10

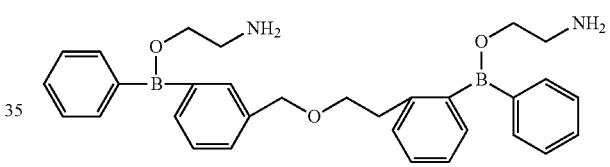

Example 370

(4-phenylhydroxyborylphenyl)(4'-phenylhydroxyborylbenzyl)ether (775)

TG 39, x-Fold 0.76, SOC IC50 2 μM

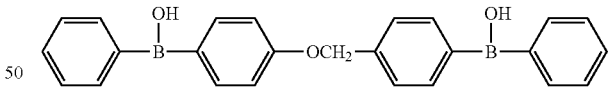

Example 371

(4-phenylaminoethoxyborylphenyl)(4'-phenylaminoethoxyborylbenzyl)ether (778)

TG 16, x-Fold 0.85, SOC IC50 2 μM

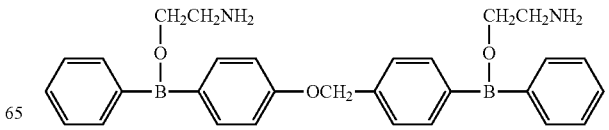

Example 372

(4-trifluoromethylphenylhydroxyborylphenyl)(4'-trifluoromethylphenylhydroxyborylbenzyl)ether (784)

TG −18, x-Fold 0.86, SOC IC50 1 μM

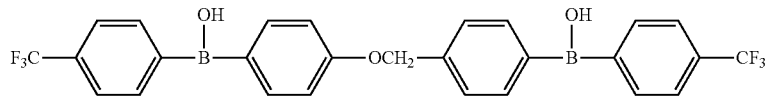

Example 373

(4-trifluoromethylphenylaminoethoxyborylphenyl) (4'-trifluoromethylphenylaminoethoxyborylbenzyl) ether (785)

TG 1, x-Fold 0.84, SOC IC50 2 μM

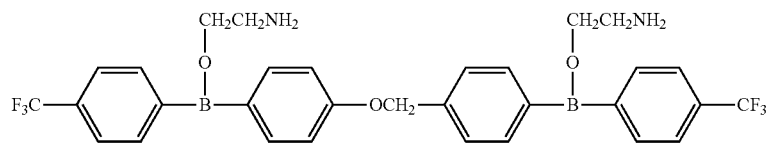

Example 374

9,10-bis-(trifluoromethylphenylhydroxyboryl)anthracene (764)

TG 17, x-Fold 1.14

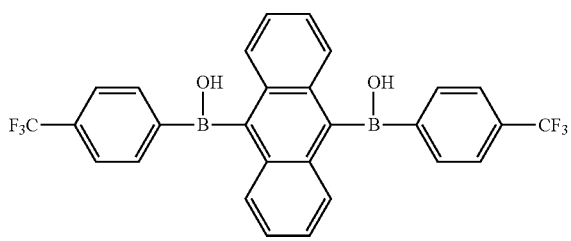 [SMILES: OB(c1ccc(C(F)(F)F)cc1)c1c2ccccc2c(B(O)c2ccc(C(F)(F)F)cc2)c2ccccc12]

Example 375

9,10-bis-(trifluoromethylphenylaminoethoxyboryl) anthracene (787)

TG 44, x-Fold 1.05

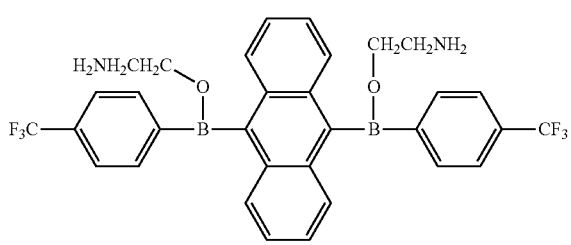

Example 376 bis(3-(1-naphthylaminoethoxyboryl)benzyl)ether (788)

TG 75, x-Fold 0.93

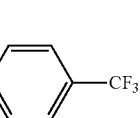

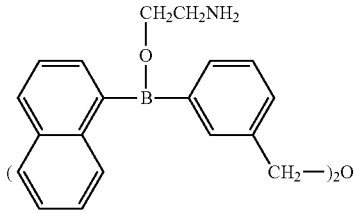

Example 377

4,5-di(phenylhydrixyboryl)-2,7-di-tert-butyl-9,9-dimethylxanthrene (763)

TG 70, x-Fold 0.75, SOC IC50 >20 μM

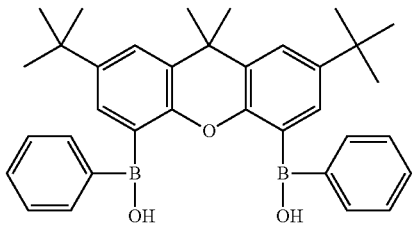 [SMILES: CC(C)(C)c1cc(B(O)c2ccccc2)c2c(c1)C(C)(C)c1cc(C(C)(C)C)cc(B(O)c3ccccc3)c1O2]

Example 378

4,5-di(phenylaminoethoxyboryl)-2,7-di-tert-butyl-9,9-dimethylxanthrene (765)

TG 88, x-Fold 0.79

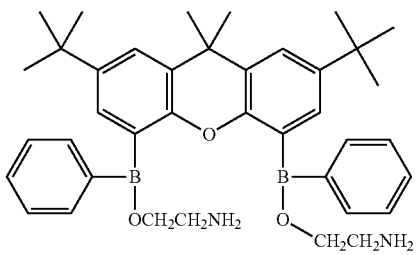

Example 379

(4-(phenylhydroxyboryl)phenoxyethyl)(4-(phenylhydroxyboryl)benzyl)ether (818)

TG 92, x-Fold 0.74

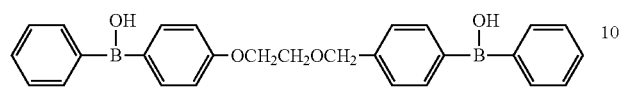

Example 380

(4-(phenylaminoethoxyboryl)phenoxyethyl)(4-(phenylaminoethoxyboryl)benzyl)ether (820)

TG 92, x-Fold 0.67

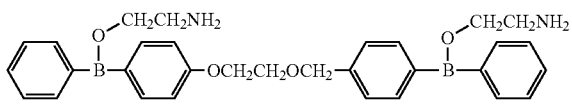

Example 381

6,6'-(phenylhydroxyboryl)-2,2'-dipyridyl (813)

TG 55, x-Fold 0.80

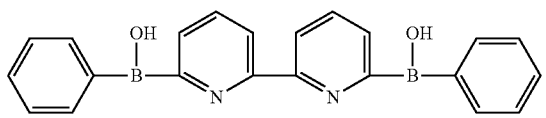 [SMILES: OB(c1ccccc1)c1cccc(-c2cccc(B(O)c3ccccc3)n2)n1]

Example 382

6,6'-(phenylaminoethoxyboryl)-2,2'-dipyridyl (814)

TG 76, x-Fold 0.80

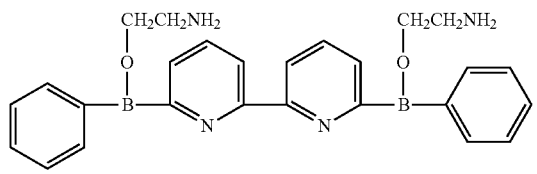

Example 383 bis(2,5-(phenylhydroxyboryl))furan (914)

TG 103, x-Fold 0.92

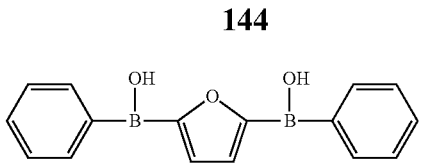

Example 384 bis(2,5-(phenylaminoethoxyboryl))furan (915)

TG 60, x-Fold 1.05

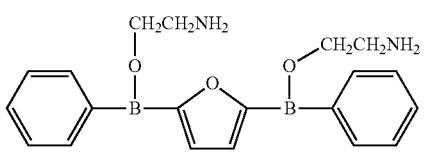

Example 385 bis(4,4'-(phenyl-N,N-dimethylaminoethoxyboryl)phenyl)ether (1007)

TG 116, x-Fold 0.78

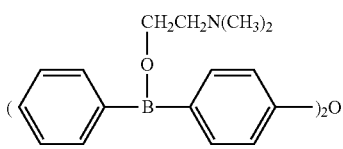

Example 386 bis(4,4'-(phenyl-N-methylaminoethoxyboryl)phenyl)ether (1014)

TG 10, x-Fold 0.98, SOC IC50 0.5 μM

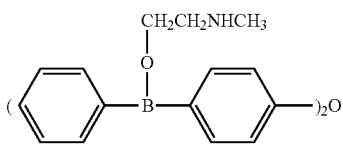

Example 387

2,8-di(phenylhydroxyboryl)dibenzothiophene (8012)

TG 96, x-Fold 0.73

2,8-Dibromodibenzothiophene (242 mg) was dissolved in ether (7 mL), and the mixture was cooled to −78° C. Secondary butyllithium (2 mL) was added and the mixture was stirred for 1 hr. Further, isopropoxyborane (460 μL) was added and the mixture was stirred for 1 hr (SOLUTION A). In a separate flask, bromobenzene (211 mg) was dissolved in ether (10 ml), secondary butyllithium (2 mL) was added and the mixture was stirred for 1 hr (SOLUTION B). SOLUTION A and SOLUTION B were mixed, and the mixture was gradually warmed to room temperature. The mixture was treated with hydrochloric acid the next morning to give the title compound (150 mg).

NMR (CDCl$_3$) 4.3 (s, 2H), 6.8-8.2 (m, 16H)

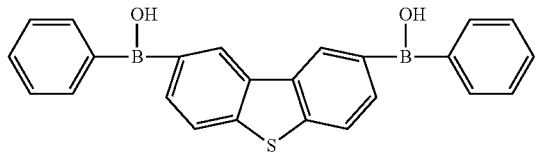 [SMILES: OB(c1ccccc1)c1ccc2sc3ccc(B(O)c4ccccc4)cc3c2c1]

Example 388 bis(4,4'-(phenyl-glutamineboryl)phenyl)ether (7085)

TG 41, x-Fold 0.67, SOC IC50 0.5 µM

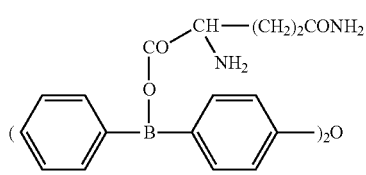

Example 389

2,8-di(3-thiophenyl-2-pyrrolidinomethoxyboryl) dibenzothiophene (8019)

TG 81, x-Fold 0.83

Compound 8012 (Example 387) (25 mg) and 2-pyrrolidinemethanol (18 mg) were stirred in ethanol at room temperature for 5 hr to give the title compound (4.9 mg).

NMR (CDCl$_3$) 1.6-1.8 (m, 8H), 3.42-4 (m, 4H), 4.64 (m, 4H), 7.0-7.8 (m, 12H)

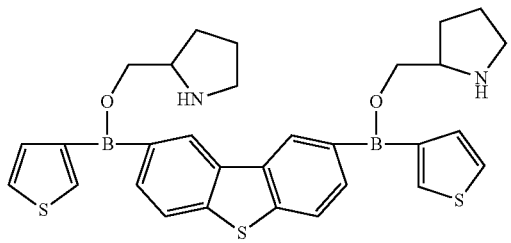 [SMILES: c1cc(B(OCC2CCCN2)c2ccc3sc4ccc(B(OCC5CCCN5)c5ccsc5)cc4c3c2)cs1]

Example 390 bis(4,4'-(phenyl-asparagineboryl)phenyl)ether (1023)

TG 56, x-Fold 0.59

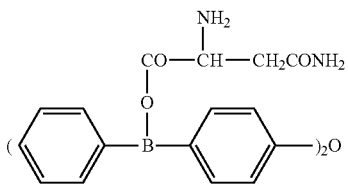

Example 391

(4-(phenyl-N-methylaminoethoxyboryl)phenyl)(4'-(hydroxymethylphenyl-N-methylaminoethoxyboryl) phenyl)ether (1028)

TG 15, x-Fold 0.32, SOC IC50 0.5 µM

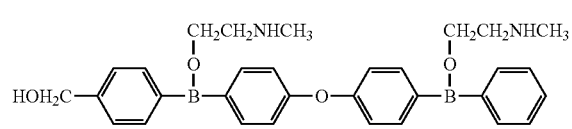

Example 392

(4-(phenyl-N,N-dimethylaminoethoxyboryl)phenyl) (4'-(hydroxymethylphenyl-N,N-dimethylaminoethoxyboryl)phenyl)ether (1030)

TG 83, x-Fold 0.91

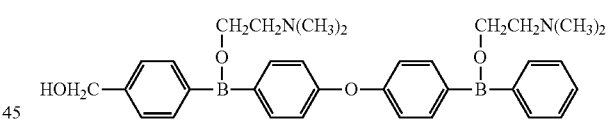

Example 393

(4-(phenyl-glutamic acid boryl)phenyl)(4'-(hydroxymethylphenyl-glutamic acid boryl)phenyl)ether (1036)

TG 117, x-Fold 0.56

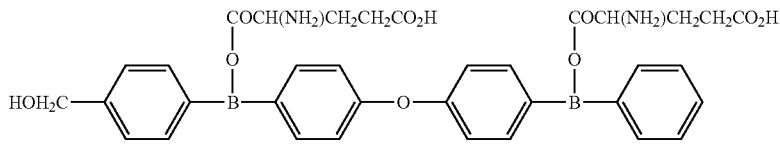

Example 394

(4-(phenyl-glutamineboryl)phenyl)(4'-(hydroxymethylphenyl-glutamineboryl)phenyl)ether (1037)

TG 41, x-Fold 0.44, SOC IC50 1.5 µM

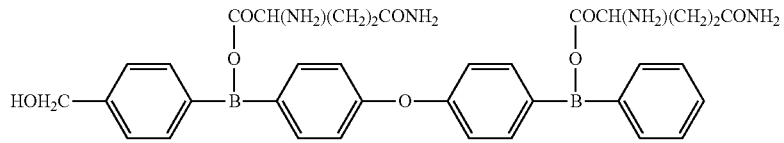

Example 395 bis(4,4'-(phenyl-N,N-dimethylaminoethoxyboryl)phenyl)ether (1007)

TG 116, x-Fold 0.86

Example 396 bis(4,4'-(phenyl-N-aminoethyl-aminoethoxyboryl)phenyl)ether (1040)

TG 3, x-Fold 0.58, SOC IC50 1.2 µM

Example 397

(4-(phenyl-cysteineboryl)phenyl)(4'-(hydroxymethylphenyl-cysteineboryl)phenyl)ether (1038)

TG 70, x-Fold 0.59

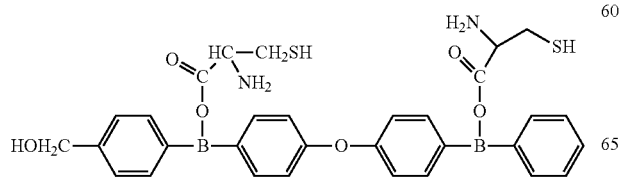

Example 398 bis(4,4'-(phenoxyphenyl-aminoethoxyboryl)phenyl)ether (1042)

TG −17, x-Fold 0.88

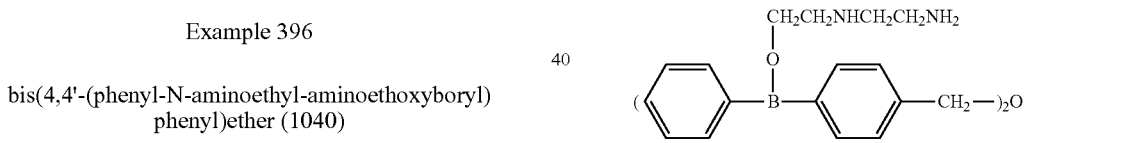

Example 399 bis(4,4'-(phenyl-N-aminoethyl-aminoethoxyboryl)benzyl)ether (1084)

TG 53, x-Fold 0.96

Example 400 bis(4,4'-(phenyl-N-methylaminoethoxyboryl)benzyl)ether (2047)

TG 52, x-Fold 1.01

Example 401

(4'-trifluoromethylphenyl-N,N-dimethylaminoethoxyboryl)-4-phenyl (4'-trifluoromethylphenyl-N,N-dimethylaminoethoxyborylbenzyl)ether (1139)

TG 121, x-Fold 0.95

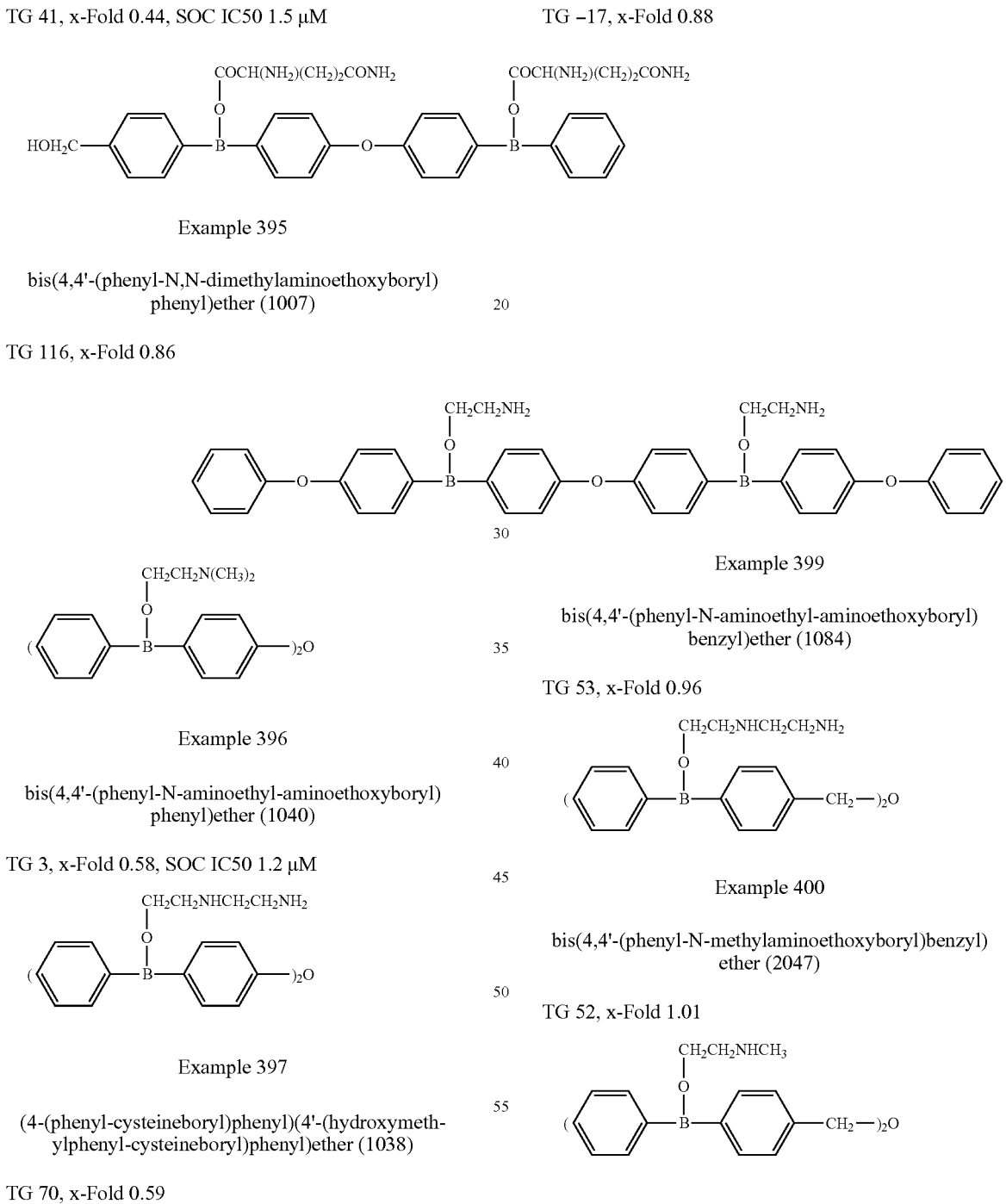

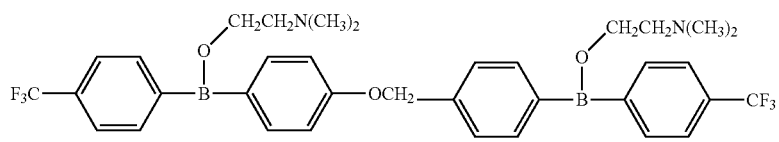

Example 402

(4'-trifluoromethylphenyl-N-methylaminoethoxyboryl)-4-phenyl(4'-trifluoromethylphenyl-N-methylaminoethoxyboryl-4-benzyl)ether (1140)

TG −12, x-Fold 0.57

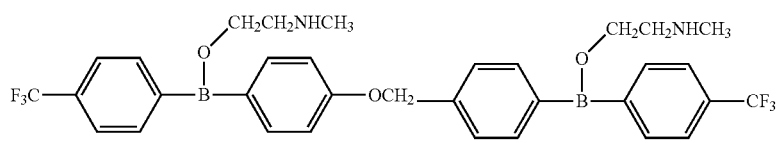

Example 403 bis(3,3'-(phenyl-N,N-dimethylaminoethoxyboryl)benzyl)ether (2022)

TG 67, x-Fold 1.14, SOC IC50 2 μM

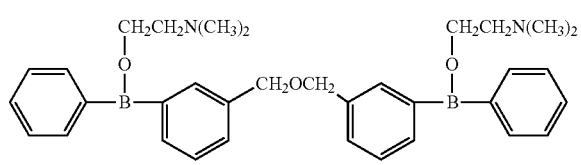

Example 404 bis(3,3'-(phenyl-asparagineboryl)benzyl)ether (2023)

TG 105, x-Fold 1.07, SOC IC50 4 μM

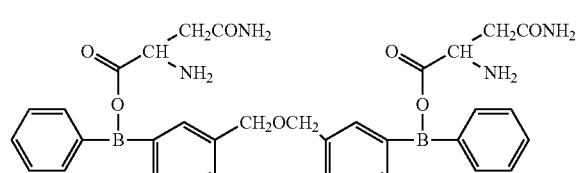

Example 405 bis(3,3'-(phenyl-aminoethylthioboryl)benzyl)ether (3014)

TG −3, x-Fold 0.86, SOC IC50 0.5 μM

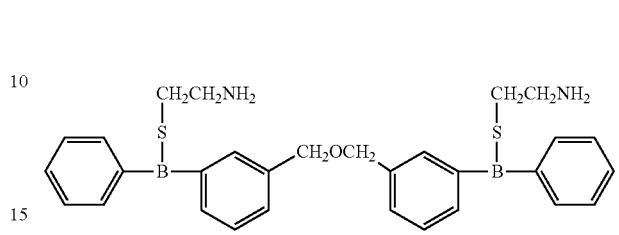

Example 406

2,8-di(3-thiophenylhydroxyboryl)dibenzothiophene (8013)

TG 61, x-Fold 0.85

2,8-Dibromodibenzothiophene (242 mg) was lithiated, and reacted with triisopropoxyborane (499 mg) (SOLUTION A). Bromothiophene (326 mg) was lithiated (SOLUTION B). SOLUTION A and SOLUTION B were mixed at −78° C., and the mixture was gradually warmed to room temperature to synthesize the title compound (230 mg).

NMR (DMSO) 3.45 (m, 2H), 7.5-8.1 (m, 12H)

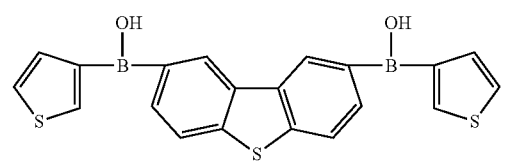 [SMILES: OB(c1ccsc1)c1ccc2sc3ccc(B(O)c4ccsc4)cc3c2c1]

Example 407 bis(4,4'-(p-trifluoromethylphenyl-hydroxyboryl)benzyl)ether (2052)

TG 77, x-Fold 1.02

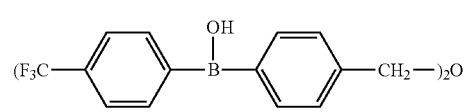

Example 408

2,8-di(phenylaminoethoxyboryl)dibenzothiophene (8014)

TG 108, x-Fold 0.92

Compound 8012 (Example 387) (30 mg) and 2-aminoethanol (7.4 mg) were synthesized by stirring at room temperature for 5 hr to give the title compound (6.3 mg).

NMR (CDCl$_3$), 2.60 (m, 4H), 3.50 (m, 4H), 3.98 (m, 4H) 7.2-8.0 (m, 16H)

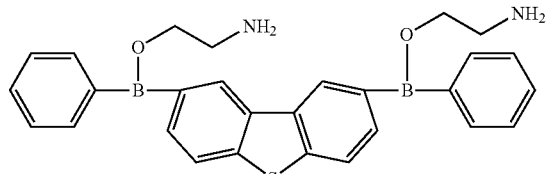

Example 409 bis(4,4'-(phenyl-lysineboryl)benzyl)ether (2051)

TG 29, x-Fold 0.86, SOC IC50 1.5 μM

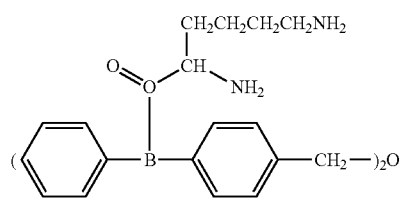

Example 410 bis(4,4'-(p-methoxy-phenyl-hydroxyboryl)benzyl) ether (2072)

TG 130, x-Fold 0.90, SOC IC50 2 μM

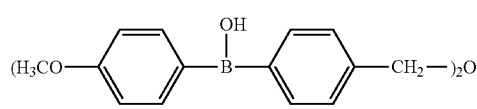

Example 411 bis(4,4'-(3,4-difluorophenyl-hydroxyboryl)benzyl) ether (2073)

TG 138, x-Fold 0.90

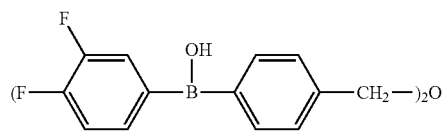

Example 412 bis(4,4'-(p-methoxyphenyl-aminoethoxyboryl)benzyl)ether (2074)

TG 65, x-Fold 0.89, SOC IC50 2 μM

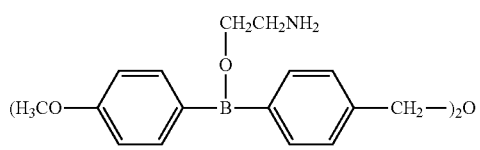

Example 413 bis(4,4'-(p-methoxyphenyl-N-methylaminoethoxyboryl)benzyl)ether (2075)

TG 28, x-Fold 0.81, SOC IC50 0.8 μM

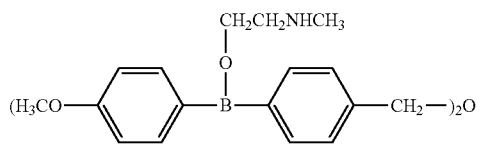

Example 414 bis(4,4'-(p-methoxyphenyl-N,N-dimethylaminoethoxyboryl)benzyl)ether (2076)

TG 128, x-Fold 0.90

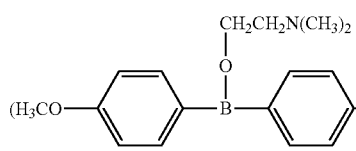

Example 415 bis(4,4'-(p-methoxyphenyl-2,4-diaminobutyric acid boryl)benzyl)ether (2077)

TG 130, x-Fold 0.90

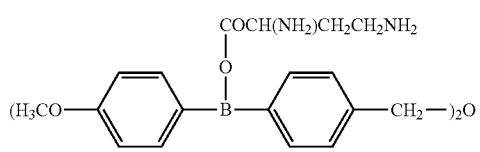

Example 416 bis(4,4'-(3,4-difluorophenyl-aminoethoxyboryl)benzyl)ether (2078)

TG 114, x-Fold 0.92

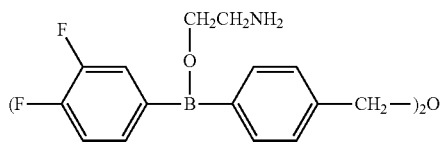

Example 417 bis(4,4'-(3,4-difluorophenyl-N-methylaminoethoxy-
boryl)benzyl)ether (2079)

TG 91, x-Fold 1.01

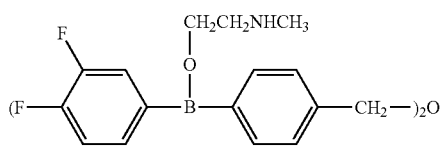

Example 418 bis(4,4'-(3,4-difluorophenyl-N,N-dimethylaminoet-
hoxyboryl)benzyl)ether (2080)

TG 45, x-Fold 1.02

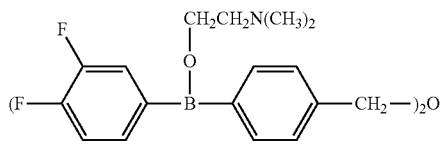

Example 419 bis(4,4'-(3,4-difluorophenyl-N-aminoethylaminoet-
hoxyboryl)benzyl)ether (2081)

TG 140, x-Fold 0.90

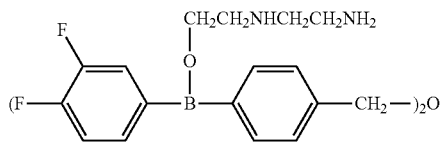

Example 420 bis(4,4'-(3-chloro-4-methylphenyl-aminoethoxybo-
ryl)benzyl)ether (2056)

TG −3, x-Fold 0.81, SOC IC50 1.2 μM

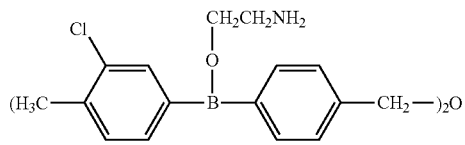

Example 421 bis(4,4'-(3-chloro-4-methylphenyl-N-methylamino-
ethoxyboryl)benzyl)ether (2057)

TG −1, x-Fold 1.03, SOC IC50 1.2 μM

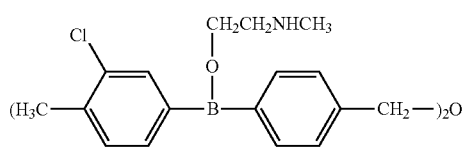

Example 422 bis(4,4'-(3-chloro-4-methylphenyl-N,N-dimethy-
laminoethoxyboryl)benzyl)ether (2058)

TG 13, x-Fold 0.95, SOC IC50 1.2 μM

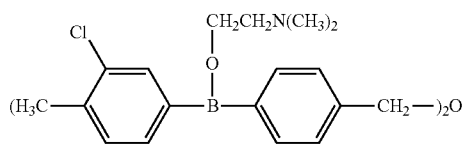

Example 423 bis(4,4'-(3-chloro-4-methylphenyl-2-piperidyl-
methoxyboryl)benzyl)ether (2059)

TG 27, x-Fold 0.76, SOC IC50 1.2 μM

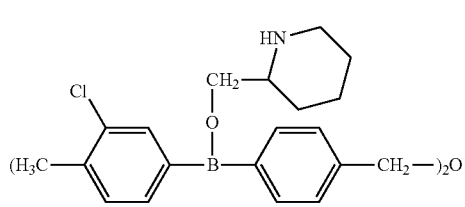

Example 424 bis(4,4'-(p-trifluoromethylphenyl-N,N-dimethylami-
noethoxyboryl)benzyl)ether (2063)

TG 22, x-Fold 1.03, SOC IC50 1.2 μM

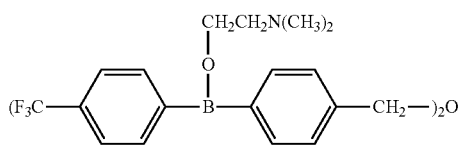

Example 425 bis(4,4'-(p-trifluoromethylphenyl-asparagineboryl)benzyl)ether (2064)

TG 130, x-Fold 0.9, SOC IC50 0.5 μM
Bis(4,4'-(p-trifluoromethylphenyl-hydroxyboryl)benzyl)ether (85 mg) and asparagine (48 mg) were reacted in ethanol (0.7 mL) to give the title compound (8 mg).

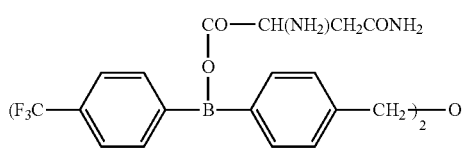

Example 426 bis(4,4'-(p-trifluoromethylphenyl-aminoethoxyboryl)benzyl)ether (2068)

TG 19, x-Fold 0.93, SOC IC50 1.2 μM

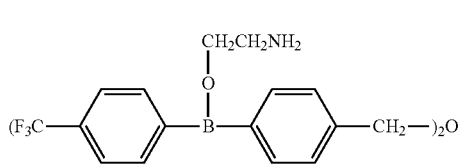

Example 427

(4-phenyl-N-methylaminoethoxyborylphenyl) (4'-phenyl-N-methylaminoethoxyborylbenzyl)ether (2093)

TG 20, x-Fold 0.73, SOC IC50 0.8 μM

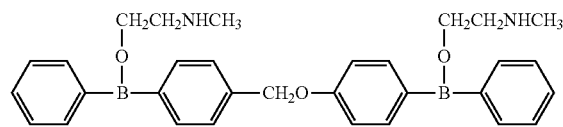

Example 428

(4-phenyl-N,N-dimethylaminoethoxyborylphenyl)(4'-phenyl-N,N-dimethylaminoethoxyborylbenzyl)ether (2094)

TG 53, x-Fold 0.82, SOC IC50 1.5 μM

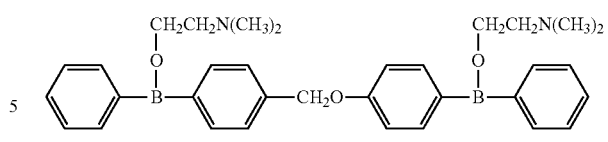

Example 429

(4-phenyl-2-pyridylmethoxyborylphenyl)(4'-phenyl-2-pyridylmethoxyborylbenzyl)ether (2095)

TG 102, x-Fold 0.81, SOC IC50 0.7 μM

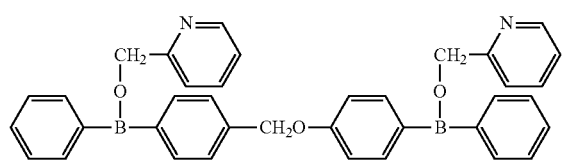

Example 430

4-(phenyl-p-methoxyphenyl-2-pyridylmethoxyboryl)-phenyl 4'-(phenyl-p-methoxyphenyl-2-pyridyl-methoxyboryl)benzylether (2096)

TG 106, x-Fold 1.03

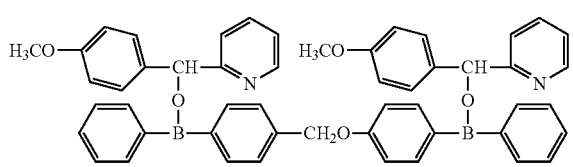

Example 431 bis(4,4'-(phenyl-3-piperidyloxyboryl)phenyl)ether (2052)

TG 118, x-Fold 1.02

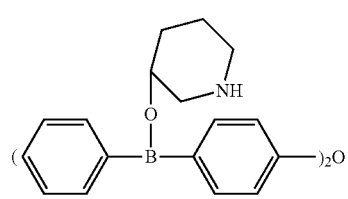

Example 432 bis(4,4'-(phenyl-2-pyridylmethoxyboryl)phenyl)ether (2111)

TG 60, x-Fold 0.71, SOC IC50 0.3 μM

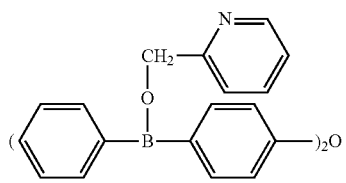

Example 433 bis(4,4'-(phenyl-aminoethylthioboryl)phenyl)ether (2112)

TG −5, x-Fold 0.71, SOC IC50 0.5 μM

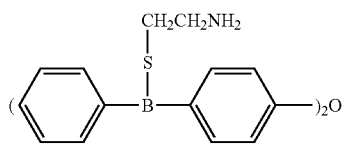

Example 434 bis(4,4'-(phenyl-2-amino-1-phenylethoxyboryl)phenyl)ether (2113)

TG 43, x-Fold 0.60, SOC IC50 0.4 μM

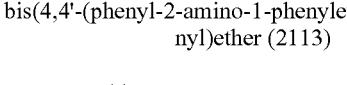

Example 435 bis(4,4'-(phenyl-ornithineboryl)phenyl)ether (2117)

TG 26, x-Fold 0.84, SOC IC50 2 μM

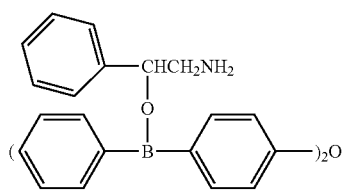

Example 436 bis(4,4'-(phenyl-2,3-diaminopropionic acid boryl)phenyl)ether (2115)

TG 104, x-Fold 0.85

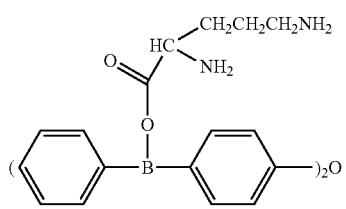

Example 437 bis(4,4'-(phenyl-lysineboryl)phenyl)ether (2116)

TG 119, x-Fold 0.85

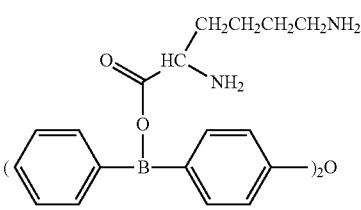

Example 438 bis(4,4'-(phenyl-2-pyrrolidinemethoxyboryl)phenyl)ether (2118)

TG 29, x-Fold 0.67, SOC IC50 2 μM

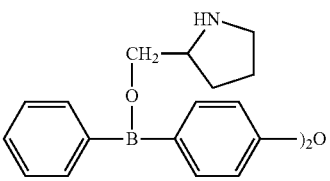

Example 439 bis(4,4'-(naphthylhydroxyboryl)phenyl)ether (2119)

TG 33, x-Fold 0.54

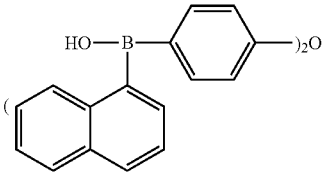

Example 440 bis(4,4'-(tolylhydroxyboryl)phenyl)ether (2120)

TG 63, x-Fold 0.69

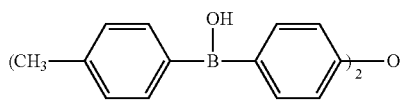

Example 441 bis(4,4'-(naphthyl-aminoethoxyboryl)phenyl)ether (2121)

TG −1, x-Fold 0.58

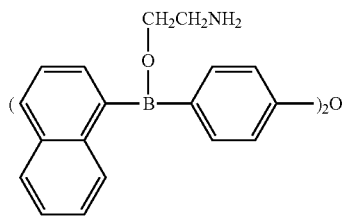

Example 442 bis(4,4'-(naphthyldimethylaminoethoxyboryl)phenyl)ether (2122)

TG 102, x-Fold 0.58

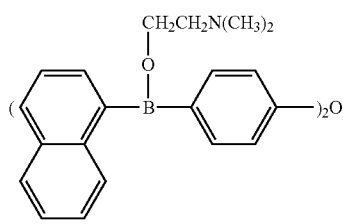

Example 443 bis(4,4'-(naphthyl-2-pyridylmethoxyboryl)phenyl)ether (2123)

TG 84, x-Fold 0.63, SOC IC50 3 μM

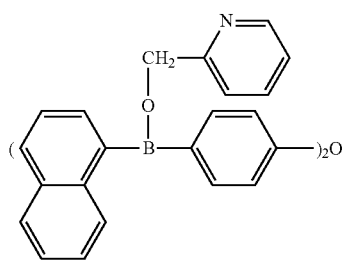

Example 444 bis(4,4'-(naphthylglutamineboryl)phenyl)ether (2124)

TG 20, x-Fold 0.65, SOC IC50 1.4 μM

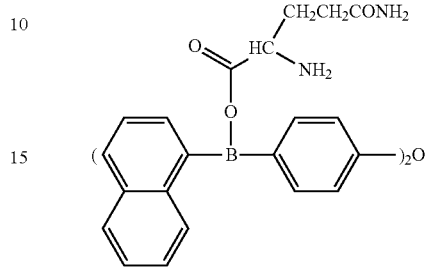

Example 445 bis(4,4'-(naphthyl 2,4-diaminopropionic acid boryl)phenyl)ether (2125)

TG 108, x-Fold 0.49

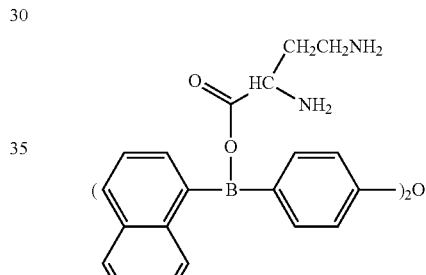

Example 446 bis(4,4'-(tolyldimethylaminoethoxyboryl)phenyl)ether (2127)

TG 73, x-Fold 0.85

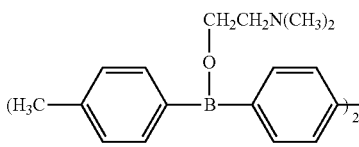

Example 447 bis(4,4'-(tolylpiperadylethoxyboryl)phenyl)ether (2128)

TG 97, x-Fold 0.49

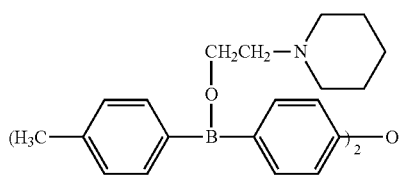

Example 448 di(3-chloro-4-methyl)phenyl(methionate-O,N)borane (4103)

TG 112, x-Fold 0.95
Di(3-chloro-4-methylphenyl)borinic acid (45.8 mg) and asparagine (19 mg) were reacted in ethanol (1 mL) at 90° C. for 1 hr to give the title compound (24 mg).

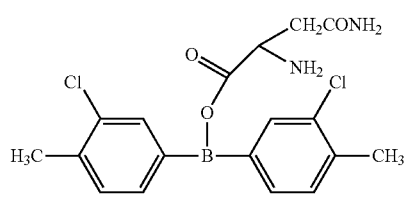

Example 449 bis(4,4'-(tolylasparagineboryl)benzyl)ether (2129)

TG 92, x-Fold 0.89

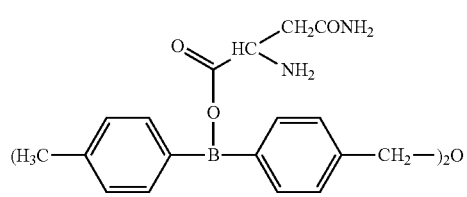

Example 450 bis(4,4'-(tolyllysineboryl)phenyl)ether (2130)

TG 53, x-Fold 0.49

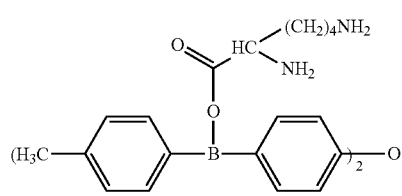

Example 451 bis(4,4'-(phenyl-aminoethylthioboryl)benzyl)ether (2135)

TG 6, x-Fold 0.91, SOC IC50 1.4 μM

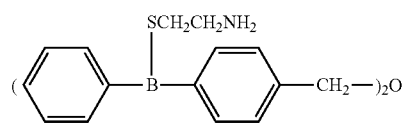

Example 452 bis(4,4'-(phenyl-2-pyrrolidinemethoxyboryl)benzyl) ether (2136)

TG 29, x-Fold 0.96, SOC IC50 0.5 μM

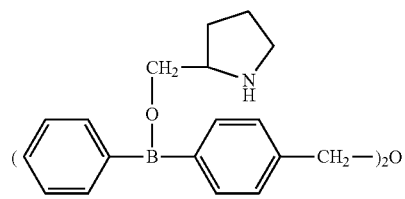

Example 453 bis(4,4'-(phenyl-2,4-diaminobutyrate boryl)benzyl)ether (2137)

TG 113, x-Fold 1.04

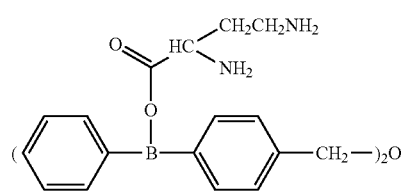

Example 454 bis(4,4'-(phenyl-butylaminoethoxyboryl)benzyl)ether (2144)

TG 15, x-Fold 0.97, SOC IC50 0.5 μM

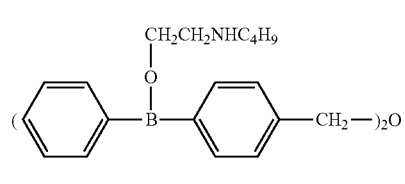

Example 455 bis(4,4'-(phenyl-phenylaminoethoxyboryl)benzyl) ether (2145)

TG 23, x-Fold 1.04, SOC IC50 0.5 μM

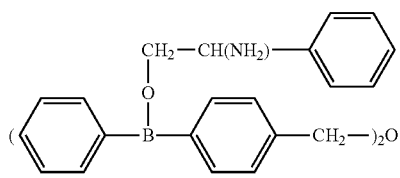

Example 456 bis(4,4'-(phenyl-benzylaminoethoxyboryl)benzyl)
ether (2146)

TG 29, x-Fold 0.87, SOC IC50 0.5 µM

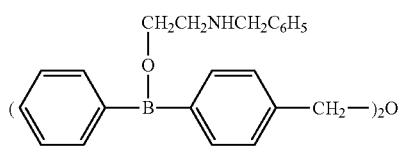

Example 457 bis(4,4'-(phenyl-N-methylpiperidine-methoxyboryl)
benzyl)ether (3002)

TG 30, x-Fold 1.10, SOC IC50 0.6 µM

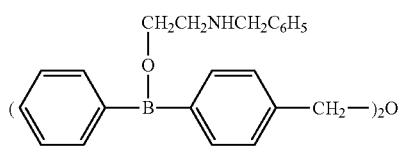

Example 458 bis(4,4'-(phenyl-1-methyl-2-aminoethoxyboryl)ben-
zyl)ether (3004)

TG 31, x-Fold 1.10, SOC IC50 0.5 µM

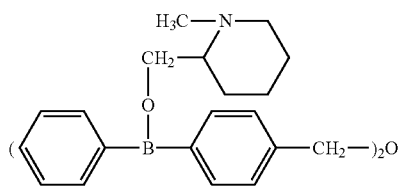

Example 459 bis(4,4'-(phenyl-1-piperidylethoxyboryl)benzyl)ether
(3005)

TG 80, x-Fold 1.03

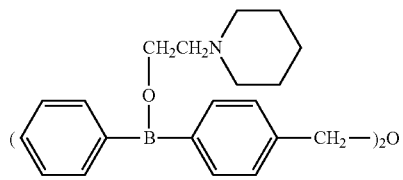

Example 460 bis(3,3'-(phenyl-2-pyrrolidinomethoxyboryl)benzyl)
ether (3015)

TG 26, x-Fold 0.95, SOC IC50 0.4 µM

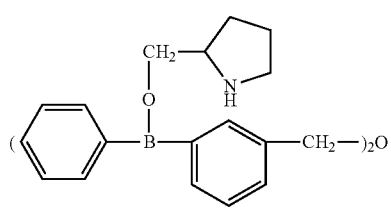

Example 461 poly(1,4-phenylene 2-pyridylmethoxyborane) (6078)

TG 30, x-Fold 0.85

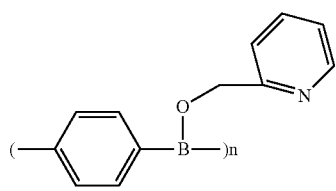

Example 462 bis(3,3'-(phenyl-2-phenyl-2-aminoethoxyboryl)ben-
zyl)ether (3018)

TG 31, x-Fold 0.92, SOC IC50 0.3 µM

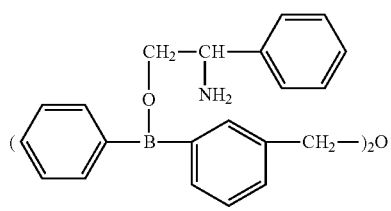

Example 463 bis(3,3'-(phenyl-2-piperidylmethoxyboryl)benzyl)
ether (3020)

TG 24, x-Fold 0.92, SOC IC50 0.3 µM

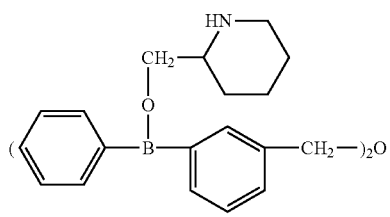

Example 464 bis(3,3'-(phenyl-dimethylaminoethoxyboryl)benzyl) ether (3021)

TG 41, x-Fold 0.76, SOC IC50 0.8

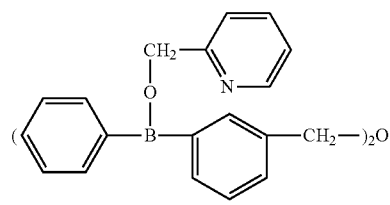

Example 468 bis(3,3'-(phenyl-2-amino-1-phenylethoxyboryl)ben-zyl)ether (3025)

TG 35, x-Fold 0.98, SOC IC50 0.3 µM

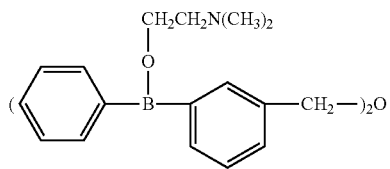

Example 465 bis(3,3'-(phenyl-1-methyl-2-aminoethoxyboryl)ben-zyl)ether (3022)

TG 18, x-Fold 1.06, SOC IC50 0.2 µM

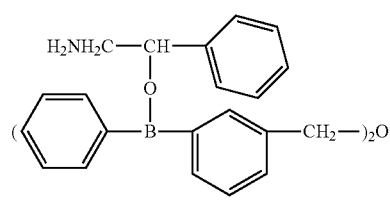

Example 469 bis(3,3'-(phenyl-N-methylaminoethoxyboryl)benzyl) ether (3026)

TG 15, x-Fold 0.94, SOC IC50 0.25 µM

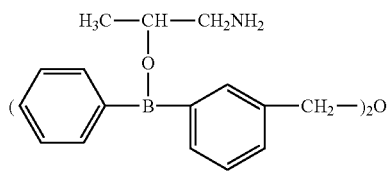

Example 466 bis(3,3'-(phenyl-1-piperidylethoxyboryl)benzyl)ether (3023)

TG 71, x-Fold 1.04

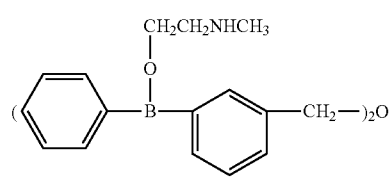

Example 470 bis(3,3'-(phenyl-N-aminoethyl-1-methyl-2-aminoet-hoxyboryl)benzyl)ether (3027)

TG 19, x-Fold 1.02, SOC IC50 0.3 µM

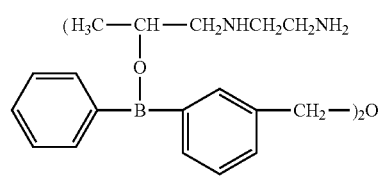

Example 471 bis(3,3'-(phenyl-glutamineboryl)benzyl)ether (3028)

TG 52, x-Fold 1.04, SOC IC50 0.6 µM

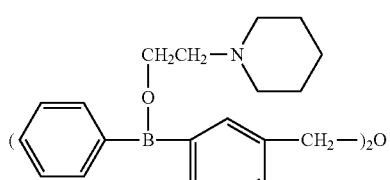

Example 467 bis(3,3'-(phenyl-2-pyridylmethoxyboryl)benzyl)ether (3024)

TG 60, x-Fold 0.98, SOC IC50 0.25 µM

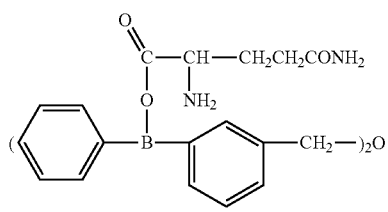

Example 472 bis(3,3'-(phenyl-2,4-diaminobutyric acid boryl)benzyl)ether (3029)

TG 47, x-Fold 0.95, SOC IC50 1 μM

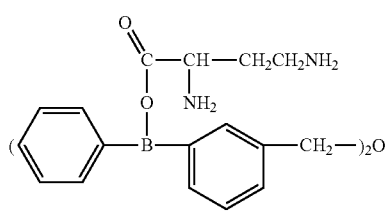

Example 473 bis(3,3'-(phenyl-N-butylaminoethoxyboryl)benzyl) ether (3030)

TG-4, x-Fold 0.96, SOC IC50 0.5 μM

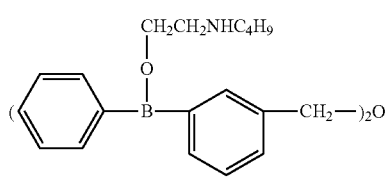

Example 474

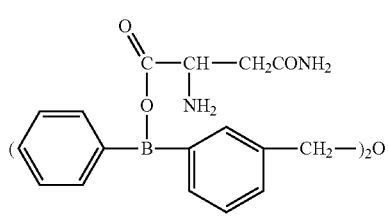

Example 475 bis(3,3'-(phenyl-lysineboryl)benzyl)ether (3032)

TG 21, x-Fold 1.01, SOC IC50 0.6 μM

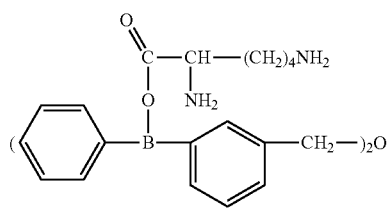

Example 476 bis(3,3'-(phenyl-ornithineboryl)benzyl)ether (3033)

TG 103, x-Fold 0.95, SOC IC50 1.5 μM

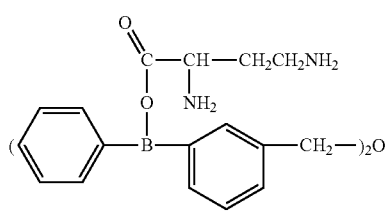

Example 477 bis(4,4'-(phenyl-2-methyl-8-quinolinooxyboryl)phenyl)ether (3037)

TG 97, x-Fold 1.02

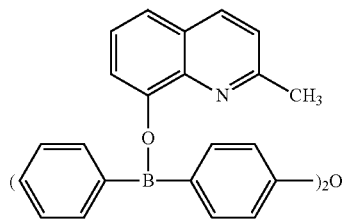

Example 478 poly(diphenyletherhydroxyborane) (7142)

TG 121

4,4'-Dibromodiphenylether (28 mg) was lithiated using isobutyllithium and reacted with triisopropoxyborane to give the title compound (150 mg).

NMR (CDCl$_3$) 3.45 (br, 1H), 6.7-8.0 (m, 8H)

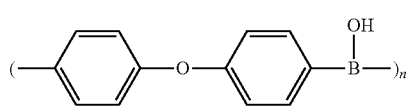

bis(3,3'-(phenyl-asparagineboryl)benzyl)ether (3031)

TG 145, x-Fold 1.04, SOC IC50 0.5 μM

Example 479 bis(4,4'-(phenyl-2-benzyl-2-amino-ethoxyboryl)benzyl)ether (3076)

TG 54, x-Fold 1.00, SOC IC50 1.5 μM

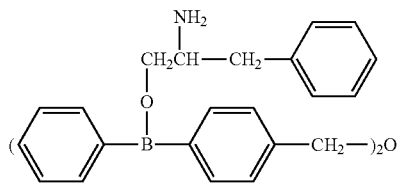

Example 480 bis(4,4'-(phenyl-2-benzyl-2-amino-ethoxyboryl)phenyl)ether (3077)

TG 59, x-Fold 0.66, SOC IC50 1.5 μM

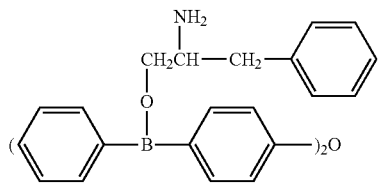

Example 481 bis(3,3'-(phenyl-2-benzyl-2-amino-ethoxyboryl)benzyl)ether (3085)

TG 48, x-Fold 0.80, SOC IC50 1.5 μM

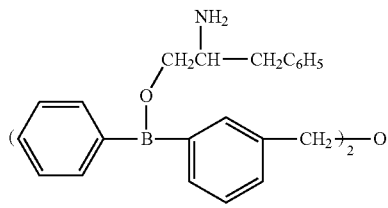

Example 482

2,8-di(phenylglutamine-O,N borane)dibenzothiophene (8015)

TG 114, x-Fold 1.08

Compound 8012 (Example 387) (40 mg) and glutamine (31 mg) were reacted at 80° C. to give the title compound (15 mg).

NMR (DMSO) 2.2 (m, 2H), 2.5 (m, 4H), 3.3 (m, 10H), 7.0-7.8 (m, 16H)

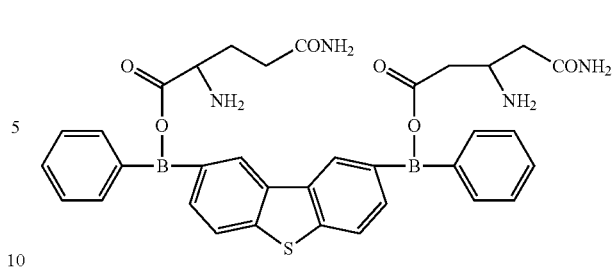

Example 483

2,8-di(phenyl 2-pyrrolidinomethoxyboryl)dibenzothiophene (8016)

TG 107, x-Fold 0.73

The title compound (37 mg) was obtained from compound 8013 (Example 406) (30 mg) and 2-pyrrolidinemethanol (16 mg).

NMR (DMSO) 1.05 (m, 4H), 1.7 (m, 4H), 3.3-3.5 (m, 4H), 7.7-8.0 (m, 16H)

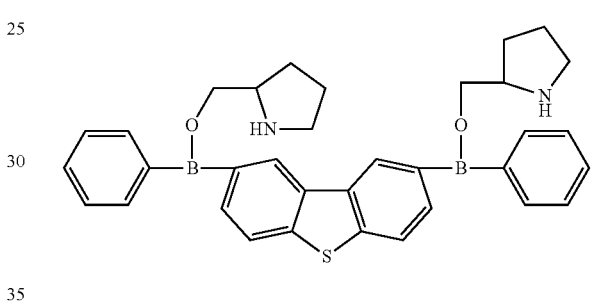

Example 484

2,8-di(phenylarginine-O,N borane)dibenzothiophene (8017)

TG 82, x-Fold 0.78

The title compound (30 mg) was obtained from compound 8012 (Example 387) (24 mg) and arginine (32 mg).

NMR (DMSO) 1.06 (m, 2H), 2.60 (m, 4H), 3.3 (m, 6H), 7.1-7.8 (m, 16H)

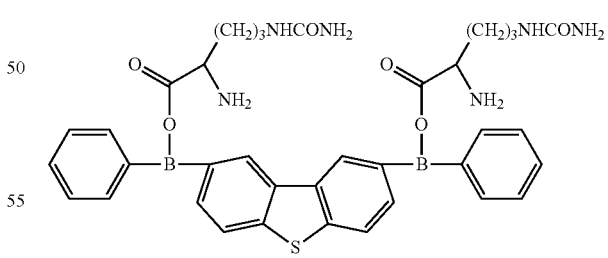

Example 485

2,8-di(3-thiophenylaminoethoxyboryl)dibenzothiophene (8018)

TG 76, x-Fold 0.98

The title compound (6.4 mg) was obtained from compound 8013 (Example 406) (42 mg) and ethanolamine (14 mg).

NMR (CDCl₃) 2.41 (4H), 2.65 (m, 4H), 3.65 (m, 4H), 7.0-7.9 (m, 12H)

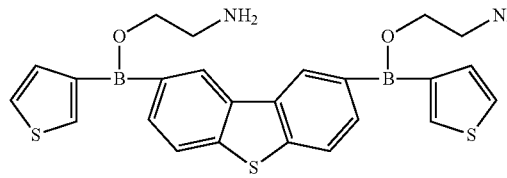

Example 486 bis(2,2'-(phenylhydroxyboryl)benzyl)ether (161OH)

TG 52, x-Fold 1.04, SOC IC50 0.5 µM

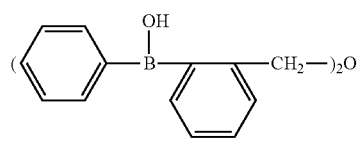

Example 487

2-aminoethyl diphenylborinate (2APB)

TG 90, x-Fold 0.64, SOC IC50 3 µM

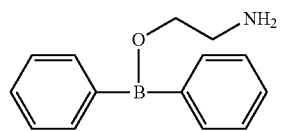 [SMILES: NCCOB(c1ccccc1)c1ccccc1]

Example 488 diphenylborinic acid (3036)

TG 108, x-Fold 1.01, SOC IC50 4 µM

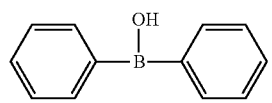

Example 489 poly(4,4'-biphenylene aminoethylthioborane) (1130)

TG 118, x-Fold 0.80

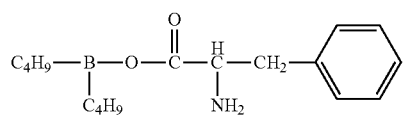

Example 490 poly(4-phenylborinic acid) (502)

TG 111, x-Fold 0.94

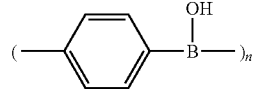

Example 491 poly(dimethylaminoethoxyphenyleneborane) (1078)

TG 106, x-Fold 0.84

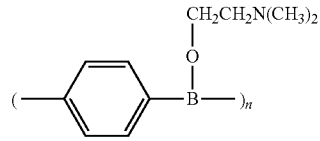

Example 492

1,3,5-tri(phenyl 2-aminoethoxyboryl)benzene (564)

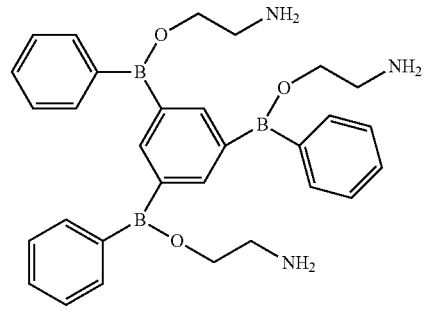 [SMILES: NCCOB(c1ccccc1)c1cc(B(OCCN)c2ccccc2)cc(B(OCCN)c2ccccc2)c1]

Example 493 dibutyl(phenylalanine-O,N)borane (929)

TG 106, x-Fold 1.03

TABLE 1

| Compound No. | Example No. | TG | x-Fold | SOC IC50 (µM) |
|---|---|---|---|---|
| 6014 | 1 | 28 | 0.95 | |
| 7111 | 2 | 28 | 0.82 | 0.2 |
| 536 | 3 | −20 | 0.49 | 0.5 |
| 1130 | 4 | 109 | 0.80 | 5 |
| 1022 | 5 | −4 | 0.60 | 0.15 |

TABLE 1-continued

| Compound No. | Example No. | TG | x-Fold | SOC IC50 (µM) |
|---|---|---|---|---|
| 7132 | 6 | 23 | 1.01 | 0.2 |
| 1620H | 7 | 14 | 1.03 | 0.2 |
| 162AE | 8 | 24 | 1.1 | 0.2 |
| 6077 | 9 | 12 | 0.87 | 0.5 |
| 6076 | 10 | 7 | 0.92 | 0.5 |
| 6047 | 11 | 36 | 0.99 | |
| 6050 | 12 | 91 | 1.04 | |
| 1122 | 13 | 100 | 1.11 | |
| 1132 | 14 | 85 | 1.03 | |
| 1133 | 15 | 91 | 0.90 | |
| 1134 | 16 | 86 | 0.95 | |
| 503 | 17 | 111 | 0.65 | |
| 1042D | 18 | −17 | 0.84 | 1.5 |
| 1042E | 19 | 47 | 0.86 | |
| 1056 | 20 | 54 | 0.63 | 4 |
| 1120 | 21 | 111 | 0.72 | |
| 1121 | 22 | 30 | 0.62 | |
| 1107 | 23 | 114 | 0.62 | |
| 1116 | 24 | 96 | 0.78 | |
| 1117 | 25 | 12 | 0.69 | |
| 1109 | 26 | 116 | 0.78 | |
| 1108-3 | 27 | 45 | 0.86 | 5 |
| 1114 | 28 | 94 | 0.72 | |
| 1115 | 29 | 52 | 0.83 | |
| 1141c | 30 | 107 | 1.02 | |
| 1146 | 31 | 127 | 0.95 | |
| 3115 | 32 | 12 | 1.02 | 1 |
| 6048 | 33 | 51 | 0.92 | |
| 6051 | 34 | 39 | 1.01 | |
| 6053 | 35 | 14 | 0.98 | |
| 1068 | 36 | 6 | 0.65 | 3 |
| 1074 | 37 | −22 | 0.73 | |
| 1077 | 38 | 79 | 0.71 | |
| 1060 | 39 | 99 | 1.04 | |
| 1062 | 40 | 26 | 0.52 | |
| 1063 | 41 | 54 | 0.63 | 2 |
| 1064 | 42 | 8 | 0.53 | 2 |
| 1065 | 43 | 13 | 0.73 | 3 |
| 1066 | 44 | 12 | 0.54 | 4 |
| 1097 | 45 | 99 | 0.52 | |
| 1102 | 46 | 93 | 0.50 | |
| 1103 | 47 | 106 | 0.58 | |
| 1104 | 48 | 102 | 0.59 | |
| 2102 | 49 | 89 | 0.96 | |
| 1105 | 50 | 112 | 0.59 | |
| 1106 | 51 | 13 | 0.43 | |
| 1069 | 52 | 73 | 0.69 | |
| 1075 | 53 | 113 | 0.74 | |
| 1080 | 54 | 112 | 0.67 | |
| 1081 | 55 | 151 | 0.71 | |
| 1082 | 56 | 74 | 0.71 | |
| 1125 | 57 | 5.98 | 0.67 | 4 |
| 1124 | 58 | 45 | 0.62 | |
| 1126 | 59 | 107 | 0.72 | |
| 1127 | 60 | 24 | 0.73 | |
| 1123 | 61 | 100 | 0.99 | |
| 1135 | 62 | 94 | 0.95 | |
| 1136 | 63 | 63 | 1.04 | |
| 1137 | 64 | 11 | 0.95 | |
| 1142 | 65 | 115 | 1.02 | 7 |
| 1144 | 66 | 120 | 1.18 | >20 |
| 1145 | 67 | 122 | 0.87 | |
| 6060 | 68 | 119 | 1.04 | |
| 5034 | 69 | 76 | 1.02 | |
| 5141 | 70 | 13 | 0.73 | 0.3 |
| 5142 | 71 | 51 | 0.97 | 1 |
| 5143 | 72 | 41 | 1.02 | 0.5 |
| 5144 | 73 | 35 | 0.85 | 1.2 |
| 5145 | 74 | 41 | 0.95 | 1 |
| 6001 | 75 | 97 | 0.88 | |
| 6004 | 76 | 117 | 0.78 | |
| 6006 | 77 | 98 | 0.91 | |
| 6007 | 78 | 104 | 1.02 | |
| 6008 | 79 | 97 | 0.88 | |
| 6009 | 80 | 93 | 0.90 | |
| 6010 | 81 | 97 | 0.92 | |
| 6011 | 82 | 103 | 0.95 | |
| 6012 | 83 | 101 | 0.92 | |
| 6013 | 84 | 91 | 0.92 | |
| 504 | 85 | 128 | 0.79 | |
| 6015 | 86 | 103 | 0.99 | |
| 6016 | 87 | 91 | 1.02 | |
| 6017 | 88 | 82 | 0.83 | |
| 6018 | 89 | 80 | 0.94 | |
| 6019 | 90 | 93 | 0.81 | |
| 6020 | 91 | 107 | 0.99 | |
| 6021 | 92 | 106 | 1.00 | |
| 6023 | 93 | 117 | 0.93 | |
| 6024 | 94 | 114 | 0.95 | |
| 6025 | 95 | 114 | 0.88 | |
| 6026 | 96 | 124 | 0.86 | |
| 6027 | 97 | 122 | 0.72 | |
| 6029 | 98 | 111 | 0.95 | |
| 6030 | 99 | 109 | 0.73 | |
| 6032 | 100 | 119 | 0.97 | |
| 6033 | 101 | 122 | 1.02 | |
| 5009 | 102 | 72 | 1.10 | |
| 6034 | 103 | 114 | 0.89 | |
| 6037 | 104 | 94 | 1.16 | |
| 6038 | 105 | 92 | 1.05 | |
| 6039 | 106 | 23 | 0.92 | |
| 6040 | 107 | 111 | 0.98 | |
| 6041 | 108 | 111 | 1.00 | |
| 6042 | 109 | 108 | 1.02 | >10 |
| 6043 | 110 | 115 | 1.02 | >10 |
| 6044 | 111 | 121 | 1.02 | |
| 6046 | 112 | 123 | 0.99 | |
| 6059 | 113 | 112 | 0.99 | |
| 6059-9 | 114 | 120 | 0.99 | 2 |
| 385 | 115 | 101 | 1.07 | |
| 419 | 116 | 108 | 1.02 | |
| 434 | 117 | 108 | 0.06 | 1.5 |
| 544 | 118 | 93 | 0.97 | 2 |
| 554 | 119 | 101 | 0.84 | >20 |
| 805 | 120 | 88 | 1.08 | |
| 583 | 121 | 121 | 0.94 | |
| 880 | 122 | 93 | 0.98 | 7 |
| 870 | 123 | 98 | 0.84 | 1 |
| 656 | 124 | 90 | 0.96 | |
| 595 | 125 | 113 | | 10 |
| 601 | 126 | 81 | 1.04 | |
| 592 | 127 | 109 | 0.70 | |
| 573 | 128 | 143 | 0.93 | |
| 1016 | 129 | 101 | 0.78 | |
| 563 | 130 | 116 | 0.85 | |
| 163AE | 131 | 16 | 1.1 | 0.3 |
| 567 | 132 | 88 | 0.95 | |
| 566 | 133 | 106 | 1.00 | |
| 558 | 134 | 94 | 0.92 | |
| 602 | 135 | 99 | 1.03 | |
| 871 | 136 | 96 | 0.98 | |
| 1630H | 137 | 14 | 0.99 | 0.3 |
| 607 | 138 | 96 | 0.99 | |
| 611 | 139 | 122 | 0.88 | |
| 548 | 140 | −72 | 0.85 | |
| 620 | 141 | 97 | 0.92 | |
| 621 | 142 | 88 | 0.24 | |
| 618 | 143 | 118 | 0.90 | |
| 612 | 144 | 99 | 0.87 | |
| 6005 | 145 | 97 | 0.91 | |
| 803 | 146 | 91 | 1.02 | |
| 554 | 147 | 101 | 0.87 | 20 |
| 557 | 148 | 68 | 1.00 | |
| 607 | 149 | 96 | 0.99 | |
| 4122 | 150 | 2 | 0 | |
| 1031 | 151 | 33 | 0.87 | |
| 1073 | 152 | 54 | 1.07 | |
| 1079 | 153 | 65 | 0.79 | |
| 1089 | 154 | 105 | 0.96- | |
| 427 | 155 | 100 | 1.02 | |
| 7138 | 156 | 91 | 1.08 | |
| 1116 | 157 | 96 | 0.73 | |
| 1117 | 158 | 12 | 0.69 | |
| 926 | 159 | 102 | 0.96 | |

TABLE 1-continued

| Compound No. | Example No. | TG | x-Fold | SOC IC50 (μM) |
|---|---|---|---|---|
| 7139 | 160 | 88 | 1.02 | |
| 1098 | 161 | 6 | 0.99 | |
| 1099 | 162 | −2 | 0.85 | |
| 347 | 163 | 109 | 1.00 | |
| 376 | 164 | 94 | 0.67 | |
| 1143 | 165 | 120 | 0.99 | |
| 372 | 166 | 74 | 0.70 | |
| 2006 | 167 | 21 | 0.71 | |
| 2007 | 168 | 35 | 0.72 | |
| 1016 | 169 | 101 | 0.78 | |
| 907 | 170 | 96 | 0.96 | |
| 370 | 171 | 98 | 0.71 | |
| 2024 | 172 | 69 | 1.22 | |
| 2026 | 173 | 122 | 1.06 | |
| 2031-4 | 174 | 103 | 0.99 | |
| 2033 | 175 | 5 | 0.89 | |
| 2035 | 176 | 47 | 1.06 | |
| 2036 | 177 | 28 | 1.00 | |
| 2039 | 178 | 142 | 0.89 | |
| 2044 | 179 | 127 | 0.99 | |
| 4124 | 180 | 35 | 0.98 | |
| 424 | 181 | 54 | 0.69 | |
| 4105 | 182 | 137 | 1.01 | |
| 925 | 183 | 91 | 1.02 | |
| 2049 | 184 | 94 | 0.95 | |
| 2064 | 185 | 130 | 0.94 | >20 |
| 601 | 186 | 81 | 0.98 | |
| 2086 | 187 | 106 | 0.97 | |
| 428 | 188 | 91 | 0.98 | |
| 2088 | 189 | 119 | 0.94 | |
| 2089 | 190 | 99 | 1.05 | |
| 2090 | 191 | 85 | 1.04 | |
| 2091 | 192 | 102 | 0.95 | |
| 899 | 193 | 92 | 1.03 | |
| 901 | 194 | 106 | 1.03 | |
| 2108 | 195 | 115 | 0.77 | |
| 2109 | 196 | 117 | 0.90 | |
| 3001 | 197 | 99 | 1.02 | |
| 3003 | 198 | 28 | 0.8 | |
| 3017 | 199 | 3 | 0.90 | |
| 442 | 200 | 100 | 0.92 | |
| 431 | 201 | 99 | 0.57 | |
| 3041 | 202 | 91 | 0.94 | |
| 3044 | 203 | 97 | 0.97 | |
| 3045 | 204 | 61 | 0.79 | |
| 3087 | 205 | 47 | 0.80 | |
| 3107 | 206 | 34 | 1.14 | |
| 3108 | 207 | 83 | 0.91 | |
| 3109 | 208 | −7 | 0.67 | |
| 3111 | 209 | 1 | 0.98 | |
| 3112 | 210 | 27 | 0.98 | 2 |
| 3113 | 211 | 86 | 0.99 | 1 |
| 3073 | 212 | 115 | 0.75 | |
| 3075 | 213 | 117 | 1.00 | |
| 3114 | 214 | −7 | 0.90 | 2 |
| 3116 | 215 | 69 | 1.03 | 2 |
| 4139 | 216 | 17 | 1.03 | 0.6 |
| 4111 | 217 | 118 | 0.94 | |
| 4118 | 218 | 90 | 0.97 | |
| 4119 | 219 | 91 | 0.88 | |
| 4121 | 220 | 26 | 0.50 | 0.5 |
| 4123 | 221 | 73 | 0.94 | |
| 8003 | 222 | 122 | 0.86 | |
| 8006 | 223 | 116 | 1.02 | |
| 4127 | 224 | 112 | 0.89 | |
| 4128 | 225 | 109 | 1.03 | 0.5 |
| 4129 | 226 | 97 | 0.94 | |
| 4130 | 227 | 110 | 0.99 | |
| 4131 | 228 | 99 | 0.98 | |
| 4132 | 229 | 40 | 1.09 | 0.5 |
| 4138 | 230 | 108 | 1.03 | |
| 4140 | 231 | 94 | 1.01 | |
| 4141 | 232 | 108 | 1.10 | |
| 4142 | 233 | 112 | 1.12 | |
| 4143 | 234 | 98 | 1.07 | 0.5 |
| 4144 | 235 | 80 | 1.03 | |
| 4145 | 236 | 87 | 1.10 | |
| 4146 | 237 | 88 | 1.15 | |
| 4147 | 238 | 87 | 1.07 | |
| 356 | 239 | 126 | 0.94 | |
| 7117 | 240 | 25 | 0.99 | 0.08 |
| 244 | 241 | 67 | 1.10 | |
| 371 | 242 | 98 | 1.17 | |
| 436 | 243 | 106 | 0.73 | |
| 372 | 244 | 74 | 0.76 | 1 |
| 921 | 245 | 94 | 0.91 | |
| 376 | 246 | 94 | 0.67 | |
| 422 | 247 | 99 | 0.91 | 0.7 |
| 421 | 248 | 103 | 0.87 | |
| 7118 | 249 | 25 | 0.74 | 0.3 |
| 1007 | 250 | 125 | 0.86 | |
| 488 | 251 | 121 | 0.83 | |
| 542 | 252 | 93 | 0.95 | 0.5 |
| 283 | 253 | 92 | 1.11 | |
| 827 | 254 | 101 | 0.95 | |
| 828 | 255 | 113 | 0.94 | 0.5 |
| 829 | 256 | 112 | 0.67 | 1.5 |
| 830 | 257 | 103 | 0.98 | |
| 833 | 258 | 110 | | 5 |
| 841 | 259 | 67 | 0.97 | 2.5 |
| 836 | 260 | 106 | 0.89 | |
| 837 | 261 | 109 | 0.89 | |
| 838 | 262 | 115 | 0.97 | |
| 2045 | 263 | 146 | 0.89 | 3 |
| 842 | 264 | 109 | 1.00 | 5 |
| 851 | 265 | 112 | 0.94 | |
| 847 | 266 | 84 | 0.87 | 3 |
| 848 | 267 | 82 | 0.60 | 3 |
| 852 | 268 | 103 | 0.96 | 5 |
| 879 | 269 | 95 | 1.01 | 3 |
| 855 | 270 | 111 | 0.54 | 0.7 |
| 906 | 271 | 109 | 1.07 | 0.5 |
| 2043 | 272 | 83 | 0.09 | 0.3 |
| 1024 | 273 | 83 | 0.56 | 0.25 |
| 1023 | 274 | 56 | 0.59 | 0.3 |
| 1036 | 275 | 117 | 0.67 | 0.3 |
| 854 | 276 | 105 | 0.8 | |
| 843 | 277 | 105 | 0.98 | 0.3 |
| 7119 | 278 | 2 | 1.08 | 0.3 |
| 894 | 279 | 103 | 0.98 | |
| 897 | 280 | 98 | 0.88 | |
| 4123 | 281 | 77 | 0.94 | |
| 4103 | 282 | 112 | 0.95 | 0.3 |
| 4125 | 283 | 12 | 0.83 | 0.9 |
| 5003 | 284 | 89 | 1.03 | |
| 5004 | 285 | 51 | 0.99 | 2 |
| 5012 | 286 | 104 | 0.93 | |
| 5013 | 287 | 146 | 1.00 | |
| 5014 | 288 | 106 | 1.02 | |
| 5015 | 289 | 94 | 1.08 | 0.3 |
| 5018 | 290 | 113 | 1.05 | |
| 5019 | 291 | 50 | 1.02 | 0.5 |
| 5020 | 292 | 146 | 1.00 | 1 |
| 5021 | 293 | 116 | 0.91 | |
| 4106 | 294 | 114 | 0.96 | 2 |
| 4107 | 295 | 107 | 0.92 | 0.8 |
| 795 | 296 | 97 | 0.74 | |
| 806 | 297 | 89 | 0.69 | |
| 810 | 298 | 101 | 1.01 | |
| 8007 | 299 | 118 | 1.13 | |
| 1085 | 300 | 95 | 0.80 | 5 |
| 1083 | 301 | 108 | 0.84 | |
| 6062 | 302 | 103 | 0.94 | |
| 6082 | 303 | 103 | 0.91 | |
| 8020 | 304 | 47 | 0.90 | |
| 6095 | 305 | 94 | 0.98 | |
| 6096 | 306 | 90 | 0.98 | |
| 7021 | 307 | 54 | 1.06 | 0.5 |
| 7020 | 308 | 27 | 1.05 | 0.5 |
| 7047 | 309 | 109 | 0.93 | |
| 7051 | 310 | 114 | 1.02 | |
| 7052 | 311 | 111 | 1.00 | |
| 7053 | 312 | 98 | 1.00 | |
| 7056 | 313 | 107 | 0.98 | |

TABLE 1-continued

| Compound No. | Example No. | TG | x-Fold | SOC IC50 (µM) |
|---|---|---|---|---|
| 7057 | 314 | 104 | 0.93 | |
| 7058 | 315 | 102 | 0.92 | |
| 7059 | 316 | 72 | 1.11 | |
| 7063 | 317 | 107 | 0.99 | |
| 7064 | 318 | 81 | 1.02 | |
| 7065 | 319 | 108 | 1.04 | |
| 1128 | 320 | 100 | 0.78 | 5 |
| 1129 | 321 | 116 | 0.78 | |
| 612 | 322 | 98 | 0.32 | 0.2 |
| 502 | 323 | 111 | 0.82 | |
| 7126 | 324 | | 0.76 | |
| 2054 | 325 | 92 | 0.99 | 4 |
| 8009 | 326 | 103 | 1.09 | |
| 8010 | 327 | 14 | 1.07 | |
| 2072 | 328 | 100 | 1.04 | |
| 672 | 329 | 81 | | 0.2 |
| 655 | 330 | 89 | 0.90 | |
| 682 | 331 | 101 | 0.98 | 1 |
| 674 | 332 | 21 | 0.98 | 0.2 |
| 701 | 333 | 107 | 1.09 | |
| 687 | 334 | 21 | 1.02 | 0.3 |
| 686 | 335 | 91 | 1.02 | |
| 688 | 336 | 101 | 1.02 | |
| 689 | 337 | 102 | 0.98 | |
| 693 | 338 | 110 | 0.83 | |
| 696 | 339 | 115 | 0.91 | |
| 700 | 340 | 63 | 1.01 | |
| 701 | 341 | 107 | 1.04 | |
| 702 | 342 | 114 | 1.02 | |
| 704 | 343 | 55 | 1.02 | |
| 705 | 344 | 91 | 0.93 | |
| 706 | 345 | 95 | 0.92 | |
| 707 | 346 | 101 | 0.81 | |
| 708 | 347 | 104 | 0.90 | |
| 710 | 349 | 104 | 0.80 | |
| 717 | 350 | 105 | 0.92 | |
| 711 | 351 | 103 | 1.00 | |
| 718 | 352 | 97 | 1.02 | |
| 712 | 353 | 115 | 0.85 | |
| 719 | 354 | 113 | 1.09 | |
| 731 | 355 | 91 | 1.09 | |
| 735 | 356 | 51 | 1.06 | |
| 736 | 357 | 89 | 1.03 | |
| 739 | 358 | 112 | 0.91 | |
| 744 | 359 | 139 | 0.96 | |
| 745 | 360 | 88 | 1.05 | |
| 709 | 361 | 100 | 0.88 | >20 |
| 729 | 362 | 108 | 1.08 | |
| 752 | 363 | 97 | 0.92 | |
| 754 | 364 | 44 | 0.82 | |
| 753 | 365 | 118 | 0.91 | |
| 8011 | 366 | 108 | 0.93 | |
| 513 | 367 | 113 | 0.73 | |
| 6055 | 368 | 52 | 1.03 | |
| 7133 | 369 | 105 | 1.10 | |
| 775 | 370 | 39 | 0.76 | 2 |
| 778 | 371 | 16 | 0.85 | 2 |
| 784 | 372 | −18 | 0.86 | 1 |
| 785 | 373 | 1 | 0.84 | 2 |
| 764 | 374 | 17 | 1.14 | |
| 787 | 375 | 44 | 1.05 | |
| 788 | 376 | 75 | 0.93 | |
| 763 | 377 | 70 | 0.75 | >20 |
| 765 | 378 | 88 | 0.79 | |
| 818 | 379 | 92 | 0.74 | |
| 820 | 380 | 92 | 0.67 | |
| 813 | 381 | 55 | 0.80 | |
| 814 | 382 | 76 | 0.80 | |
| 914 | 383 | 103 | 0.92 | |
| 915 | 384 | 60 | 1.05 | |
| 1007 | 385 | 116 | 0.78 | |
| 1014 | 386 | 10 | 0.98 | 0.5 |
| 8012 | 387 | 96 | 0.73 | |
| 7085 | 388 | 41 | 0.67 | 0.5 |
| 8019 | 389 | 81 | 0.83 | |
| 1023 | 390 | 56 | 0.59 | |
| 1028 | 391 | 15 | 0.32 | 0.5 |
| 1030 | 392 | 83 | 0.91 | |
| 1036 | 393 | 117 | 0.56 | |
| 1037 | 394 | 41 | 0.44 | 1.5 |
| 1007 | 395 | 116 | 0.86 | |
| 1040 | 396 | 3 | 0.58 | 1.2 |
| 1038 | 397 | 70 | 0.59 | |
| 1042 | 398 | −17 | 0.88 | |
| 1084 | 399 | 53 | 0.96 | |
| 2047 | 400 | 52 | 1.01 | |
| 1139 | 401 | 121 | 0.95 | |
| 1140 | 402 | −12 | 0.57 | |
| 2022 | 403 | 67 | 1.14 | 2 |
| 2023 | 404 | 105 | 1.07 | 4 |
| 3014 | 405 | −3 | 0.86 | 0.5 |
| 8013 | 406 | 61 | 0.85 | |
| 2052 | 407 | 77 | 1.02 | |
| 8014 | 408 | 108 | 0.92 | |
| 2051 | 409 | 29 | 0.86 | 1.5 |
| 2072 | 410 | 130 | 0.90 | 2 |
| 2073 | 411 | 138 | 0.90 | |
| 2074 | 412 | 65 | 0.89 | 2 |
| 2075 | 413 | 28 | 0.81 | 0.8 |
| 2076 | 414 | 128 | 0.90 | |
| 2077 | 415 | 130 | 0.90 | |
| 2078 | 416 | 114 | 0.92 | |
| 2079 | 417 | 91 | 1.01 | |
| 2080 | 418 | 45 | 1.02 | |
| 2081 | 419 | 140 | 0.90 | |
| 2056 | 420 | −3 | 0.81 | 1.2 |
| 2057 | 421 | −1 | 1.03 | 1.2 |
| 2058 | 422 | 13 | 0.95 | 1.2 |
| 2059 | 423 | 27 | 0.76 | 1.2 |
| 2063 | 424 | 22 | 1.03 | 1.2 |
| 2064 | 425 | 130 | 0.9 | 0.5 |
| 2068 | 426 | 19 | 0.93 | 1.2 |
| 2093 | 427 | 20 | 0.73 | 0.8 |
| 2094 | 428 | 53 | 0.82 | 1.5 |
| 2095 | 429 | 102 | 0.81 | 0.7 |
| 2096 | 430 | 106 | 1.03 | |
| 2052 | 431 | 118 | 1.02 | |
| 2111 | 432 | 60 | 0.71 | 0.3 |
| 2112 | 433 | −5 | 0.71 | 0.5 |
| 2113 | 434 | 43 | 0.60 | 0.4 |
| 2117 | 435 | 26 | 0.84 | 2 |
| 2115 | 436 | 104 | 0.85 | |
| 2116 | 437 | 119 | 0.85 | |
| 2118 | 438 | 29 | 0.67 | 2 |
| 2119 | 439 | 33 | 0.54 | |
| 2120 | 440 | 63 | 0.69 | |
| 2121 | 441 | −1 | 0.58 | |
| 2122 | 442 | 102 | 0.58 | |
| 2123 | 443 | 84 | 0.63 | 3 |
| 2124 | 444 | 20 | 0.65 | 1.4 |
| 2125 | 445 | 108 | 0.49 | |
| 2127 | 446 | 73 | 0.85 | |
| 2128 | 447 | 97 | 0.49 | |
| 4103 | 448 | 112 | 0.95 | |
| 2129 | 449 | 92 | 0.89 | |
| 2130 | 450 | 53 | 0.49 | |
| 2135 | 451 | 6 | 0.91 | 1.4 |
| 2136 | 452 | 29 | 0.96 | 0.5 |
| 2137 | 453 | 113 | 1.04 | |
| 2144 | 454 | 15 | 0.97 | 0.5 |
| 2145 | 455 | 23 | 1.04 | 0.5 |
| 2146 | 456 | 29 | 0.87 | 0.5 |
| 3002 | 457 | 30 | 1.10 | 0.6 |
| 3004 | 458 | 31 | 1.10 | 0.5 |
| 3005 | 459 | 80 | 1.03 | |
| 3015 | 460 | 26 | 0.95 | 0.4 |
| 6078 | 461 | 30 | 0.85 | |
| 3018 | 462 | 31 | 0.92 | 0.3 |
| 3020 | 463 | 24 | 0.92 | 0.3 |
| 3021 | 464 | 41 | 0.76 | 0.8 |
| 3022 | 465 | 18 | 1.06 | 0.2 |
| 3023 | 466 | 71 | 1.04 | |
| 3024 | 467 | 60 | 0.98 | 0.25 |
| 3025 | 468 | 35 | 0.98 | 0.3 |

TABLE 1-continued

| Compound No. | Example No. | TG | x-Fold | SOC IC50 (μM) |
|---|---|---|---|---|
| 3026 | 469 | 15 | 0.94 | 0.25 |
| 3027 | 470 | 19 | 1.02 | 0.3 |
| 3028 | 471 | 52 | 1.04 | 0.6 |
| 3029 | 472 | 47 | 0.95 | 1 |
| 3030 | 473 | -4 | 0.96 | 0.5 |
| 3031 | 474 | 145 | 1.04 | 0.5 |
| 3032 | 475 | 21 | 1.01 | 0.6 |
| 3033 | 476 | 103 | 0.95 | 1.5 |
| 3037 | 477 | 97 | 1.02 | |
| 7142 | 478 | 121 | | |
| 3076 | 479 | 54 | 1.00 | 1.5 |
| 3077 | 480 | 59 | 0.66 | 1.5 |
| 3085 | 481 | 48 | 0.80 | 1.5 |
| 8015 | 482 | 114 | 1.08 | |
| 8016 | 483 | 107 | 0.73 | |
| 8017 | 484 | 82 | 0.78 | |
| 8018 | 485 | 76 | 0.98 | |
| 1610H | 486 | 52 | 1.04 | 0.5 |
| 2APB | 487 | 90 | 0.64 | 3 |
| 3036 | 488 | 108 | 1.01 | 4 |
| 1130 | 489 | 118 | 0.80 | |
| 502 | 490 | 111 | 0.94 | |
| 1078 | 491 | 106 | 0.84 | |
| 564 | 492 | | | |
| 929 | 493 | 106 | 1.03 | |

Experimental Example 4

The effects of 162AE (bis(3,3'-(phenylaminoethoxyboryl) benzyl)ether described in Example 8) and 163AE (bis(4,4'-(phenylaminoethoxyboryl)benzyl)ether described in Example 131) for $I_{CRAC}$, whose molecular entity as one of SOCE has been clarified, were investigated using an electrophysiological method. STIM1 and Orai1 (CRACM1) were forcibly expressed in HEK293 cells, and whole cell records were taken by the Patch clamp technique. BAPTA (20 mM), which is a calcium chelator, and $IP_3$ (20 μM) that depletes intracellular calcium store were added to a recording electrode internal solution (120 mM Cs-glutamate, 10 mM HEPES, 3 mM $MgCl_2$), 10 mM calcium was added to an extracellular solution to facilitate observation of calcium electric current, and a ramp command from −150 mV to +150 mV was input at 0.5 Hz to obtain a current-voltage curve. For quantification of SOCE, the size of the inward current at −80 mV was used as an index. After the start of the whole cell recording, time was taken to sufficiently activate SOCE ($I_{CRAC}$), and compounds 162AE and 163AE as inhibitors were administered to the cells. As a result of the experiment, these inhibitors highly strongly inhibited SOCE ($I_{CRAC}$) and the IC50 thereof was 0.086 μM, 0.17 μM (for 162AE, 163AE, respectively), thus exhibiting a strong inhibitory effect. Moreover, since SOCE ($I_{CRAC}$) reconstituted by STIM1 and Orai1 (CRACM1) is indispensible for the immune response of T cells, it is considered possible to suppress excess immune response that occurs in autoimmune diseases, by utilizing the inhibitor, and treat the disease or mitigate the symptoms.

INDUSTRIAL APPLICABILITY

According to the present invention, a drug for the prophylaxis and/or treatment of a disease based on abnormal protein cross-linking reaction, such as Alzheimer's disease, Parkinson's disease, Celiac disease, cataract, mad cow disease, congenital lamellar ichthyosis, congenital hemostatic disorder and the like can be provided.

This application is based on a patent application No. 2008-207315 filed in Japan (filing date: Aug. 11, 2008), the contents of which are incorporated in full herein by this reference.

The invention claimed is:
1. A compound of formula (8')

$$R_3'—B(ZR_1')—X'—B(ZR_2')—R_4' \quad (8')$$

wherein
B is a boron atom,
Z is O,
$R_1'$ and $R_2'$ are H, —$(CH_2)_m$—$NH_2$, —$CH_2R_{12}'$ wherein $R_{12}'$ is pyrrolidinyl, —$COCH(NH_2)$—$(CH_2)_m NH$-$CONH_2$, or —$COCH(NH_2)$—$(CH_2)_m$—$CONH_2$, and m is an integer of 1 to 5,
$R_3'$ and $R_4'$ are phenyl or thienyl, and
X' is a 2,8-dibenzothiophenyl group,
or a pharmaceutically acceptable salt thereof.
2. The compound according to claim 1, which is any of

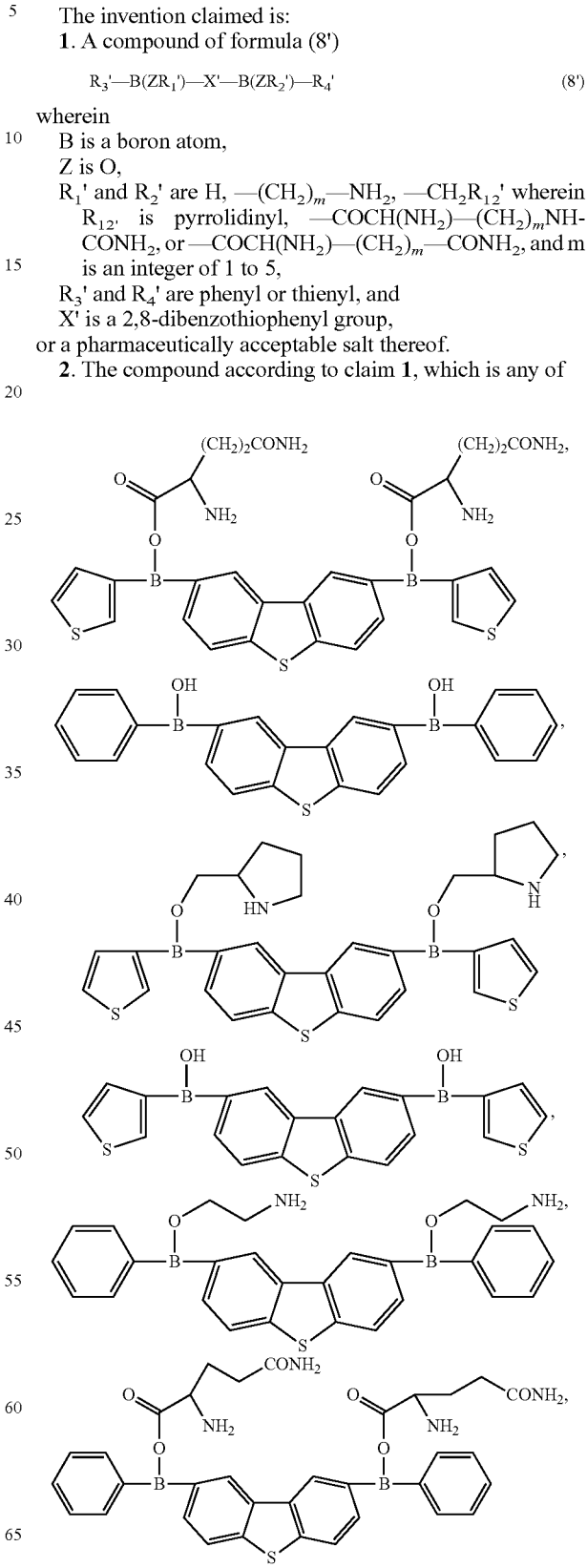

181
-continued

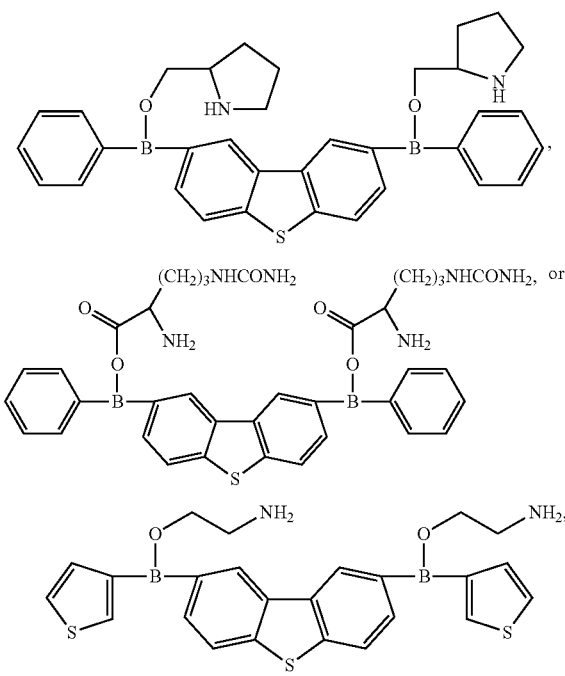

or a pharmaceutically acceptable salt thereof.

3. The compound according to claim 1 of the formula

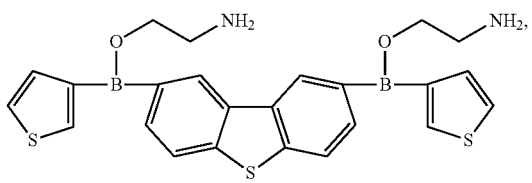 [SMILES: NCCOB(c1ccsc1)c1ccc2sc3ccc(B(OCCN)c4ccsc4)cc3c2c1]

or a pharmaceutically acceptable salt thereof.

4. A protein cross-linking inhibitor comprising the compound according to claim 1, or a pharmaceutically acceptable salt thereof.

5. The inhibitor according to claim 4, wherein the inhibition is polyglutamine aggregation inhibition.

6. A therapeutic drug for a disease caused by cross-linking of protein, comprising the compound according to claim 1, or a pharmaceutically acceptable salt thereof, wherein the disease is selected from Alzheimer's disease, Parkinson's disease, and mad cow disease.

7. A polyglutamine aggregation inhibitor comprising the compound according to claim 1, or a pharmaceutically acceptable salt thereof.

8. A therapeutic drug for a disease caused by polyglutamine aggregation, comprising the compound according to claim 1, or a pharmaceutically acceptable salt thereof, wherein the disease is Huntington's disease.

* * * * *